United States Patent [19]

Gregory

[11] Patent Number: 4,705,799

[45] Date of Patent: Nov. 10, 1987

[54] AMINOMETHYL OXOOXAZOLIDINYL BENZENES USEFUL AS ANTIBACTERIAL AGENTS

[75] Inventor: Walter A. Gregory, Wilmington, Del.

[73] Assignee: E. I. Du Pont de Nemours and Company, Wilmington, Del.

[21] Appl. No.: 803,191

[22] Filed: Dec. 2, 1985

Related U.S. Application Data

[63] Continuation-in-part of Ser. No. 676,745, Dec. 5, 1984, abandoned, which is a continuation-in-part of Ser. No. 578,332, Feb. 14, 1984, abandoned, which is a continuation-in-part of Ser. No. 501,897, Jun. 7, 1983, abandoned.

[51] Int. Cl.[4] ..................... A61K 31/42; C07D 263/22
[52] U.S. Cl. .................................... 514/376; 514/326; 546/209; 548/229; 548/232
[58] Field of Search ............... 548/229, 232; 546/209; 514/326, 376

[56] References Cited

U.S. PATENT DOCUMENTS

| Re. 29,607 | 4/1978 | Fauran et al. | 548/229 |
|---|---|---|---|
| 3,687,965 | 8/1972 | Fauran et al. | 548/229 |
| 4,128,654 | 12/1978 | Fugitt et al. | 548/229 |
| 4,250,318 | 2/1981 | Dostert et al. | 548/229 |
| 4,287,351 | 9/1981 | Bourgery | 548/232 |
| 4,340,606 | 7/1982 | Fugitt et al. | 548/229 |
| 4,461,773 | 7/1984 | Gregory | 548/232 |
| 4,476,136 | 10/1984 | Dostert et al. | 548/229 |
| 4,517,197 | 5/1985 | Ancher et al. | 548/229 |
| 4,526,786 | 7/1985 | Bourgery et al. | 548/229 |

FOREIGN PATENT DOCUMENTS

| 740092 | 10/1969 | Belgium | 548/229 |
|---|---|---|---|
| 127902 | 12/1984 | European Pat. Off. | 548/229 |
| 1222708 | 2/1971 | United Kingdom | 548/229 |
| 2076813 | 12/1981 | United Kingdom | 548/229 |
| 2094299 | 9/1982 | United Kingdom . | |

OTHER PUBLICATIONS

WHO Guidelines for the Clinical Investigation of Antibacterial Drugs.

*Primary Examiner*—Donald G. Daus
*Assistant Examiner*—Cecilia Shen

[57] ABSTRACT

Novel aminomethyl oxooxazolidinyl benzene derivatives, including the sulfides, sulfoxides, sulfones and sulfonamides, such as (l)-N-[3-[4-(methylsulfinyl)-phenyl]-2-oxooxazolidin-5-ylmethyl]acetamide, possess useful antibacterial activity.

100 Claims, No Drawings

AMINOMETHYL OXOOXAZOLIDINYL BENZENES USEFUL AS ANTIBACTERIAL AGENTS

CROSS-REFERENCE

This application is a continuation-in-part of application Ser. No. 676,745 filed Dec. 5, 1984, now abandoned, which is a continuation-in-part of application Ser. No. 578,332, filed Feb. 14, 1984, now abandoned, which is a continuation-in-part of application Ser. No. 501,897, filed June 7, 1983, now abandoned.

TECHNICAL FIELD

This invention relates to novel aminomethyl oxooxazolidinyl benzene derivatives; to pharmaceutical compositions containing them, and to methods of using them to alleviate bacterial infections.

BACKGROUND OF THE INVENTION

At the present time, no existing antibacterial product provides all features deemed advantageous. There is continual development of resistance by bacterial strains. A reduction of allergic reactions and of irritation at the site of injection, and greater biological half-life (i.e., longer in vivo activity) are currently desirable features for antibacterial products.

U.S. Pat. No. 4,128,654 issued to Fugitt et al. on Dec. 5, 1978, discloses, among others, compounds of the formula:

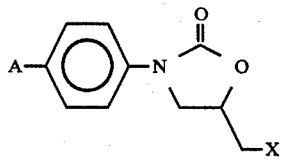

where
A=RS(O)$_n$;
X=Cl, Br or F;
R=C$_1$-C$_3$ alkyl; and
n=0, 1 or 2.

The compounds are disclosed as being useful in controlling fungal and bacterial diseases of plants.

U.S. Pat. No. Re. 29,607 reissued Apr. 11, 1978 discloses derivatives of 5-hydroxymethyl-3-substituted-2-oxazolidinones of the formula:

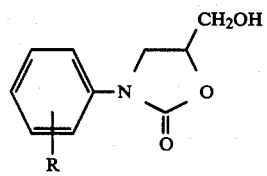

where R is H, F, CH$_3$, or CF$_3$. Such compounds are described as having antidepressive, tranquilizing, sedative, and antiinflammatory properties.

U.S. Pat. No. 4,250,318, which was issued on Feb. 10, 1981, discloses antidepressant compounds of the formula:

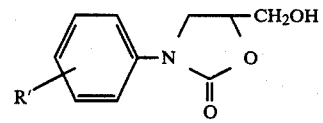

where R' can be, among others, a para-n-pentylamino group, an SR$_1$ group where R$_1$ is C$_1$-C$_5$ alkyl, or an acetylmethylthio group.

U.S. Pat. No. 4,340,606, issued to Fugitt et al. on July 20, 1982, discloses antibacterial agents of the general formula:

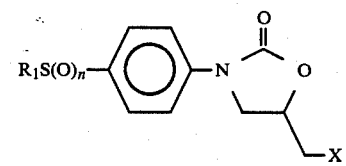

where
R$_1$=CH$_3$, C$_2$H$_5$, CF$_2$H, CF$_3$ or CF$_2$CF$_2$H; and
X=OR$_2$ (R$_2$=H or various acyl moieties).

U.S. Pat. No. 3,687,965, issued to Fauran et al. on August 29, 1972, discloses compounds of the formula:

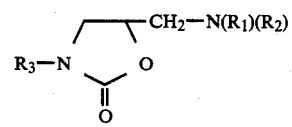

where
—N(R$_1$)(R$_2$) represents either dialkylamino radical in which the alkyl portions have one to five carbon atoms, or a heterocyclic amino radical which may be substituted by an alkyl radical having one to five carbon atoms or by a pyrrolidinocarbonylmethyl radical, and R$_3$ represents a phenyl radical which may be substituted by one or more of the following radicals:
an alkoxy radical having one to five carbon atoms;
a halogen atom;
a trifluoromethyl radical, or
a carboxyl radical which may be esterified.

The patent states that these compounds possess hypotensive, vasodilatatory, spasmolytic, sedative, myorelaxant, analgesic and antiinflammatory properties. There is no mention of antibacterial properties.

Belgian Pat. No. 892,270, published Aug. 25, 1982, discloses monoamine oxidase inhibitors of the formula

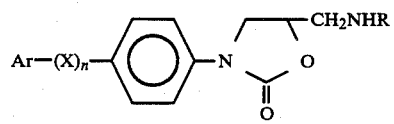

where
R is H, C$_1$-C$_4$ alkyl or propargyl;
Ar is phenyl, optionally substituted by halo or trifluoromethyl;
n is 0 or 1; and
X is —CH$_2$CH$_2$—, —CH=CH—, an acetylene group or —CH$_2$O—.

U.S. Pat. No. 4,461,773 issued to W. A. Gregory on July 24, 1984, a continuation-in-part of U.S. patent application No. 417,569 filed Sept. 15, 1982 discloses antibacterial agents of the formula

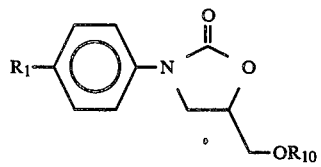

wherein, for the l, and mixtures of the d and l stereoisomers of the compound, $R_1$ is $R_2SO_2$,

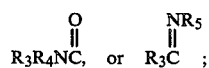

$R_2$ is $-NR_3R_4$, $-N(OR_3)R_4$, $-N_3$, $-NHNH_2$, $-NX_2$, $-NR_6X$, $-NXZ$,

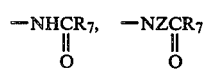

or $-N=S(O)_nR_8R_9$;

$R_3$ and $R_4$ are independently H, alkyl of 1–4 carbons or cycloalkyl of 3–8 carbons;

$R_5$ is $NR_3R_4$ or $OR_3$;

$R_6$ is alkyl of 1–4 carbons;

$R_7$ is alkyl of 1–4 carbons, optionally substituted with one or more halogens;

$R_8$ and $R_9$ are independently alkyl of 1–4 carbons or, taken together are $-(CH_2)_p-$;

$R_{10}$ is H, alkyl of 1–3 carbons,

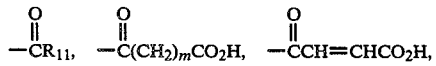

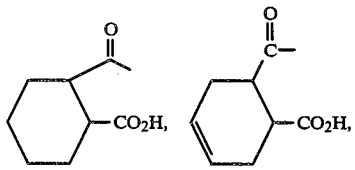

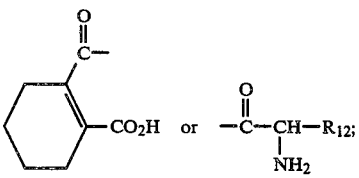

$R_{11}$ is alkyl of 1–12 carbons;

$R_{12}$ is H, alkyl of 1–5 carbons, $CH_2OH$ or $CH_2SH$;

X is Cl, Br or I;

Z is a physiologically acceptable cation;

m is 2 or 3;

n is 0 or 1; and p is 3, 4 or 5;

and when $R_{10}$ is alkyl of 1–3 carbons, $R_1$ can also be $CH_3S(O)_q$ where q is 0, 1 or 2;

or a pharmaceutically acceptable salt thereof.

None of the cited references nor any known references suggest the novel antibacterial compounds of this invention.

SUMMARY OF THE INVENTION

The novel compounds of the instant invention possess useful antibacterial activity in both in vitro and in vivo tests. Specifically, one aspect of this invention relates to compounds having the formula:

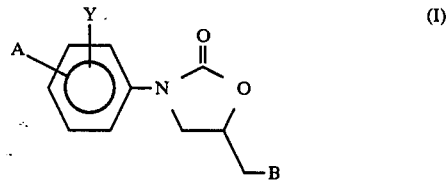

wherein, for the l, and mixtures of the d and l stereoisomers of the compound,

A is $-NO_2$, $-S(O)_nR_1$, $-S(O)_2-N=S(O)_pR_2R_3$, $-SH$,

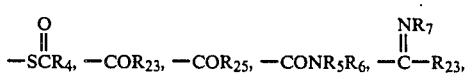

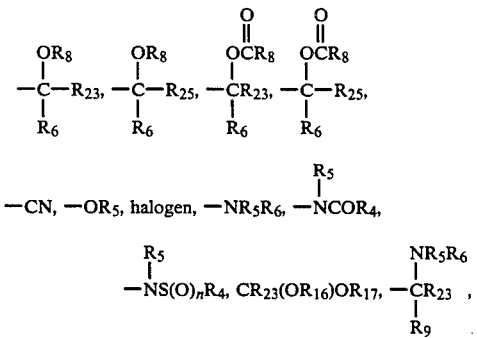

alkyl of 1 to 8 carbons, optionally substituted with one or more halogen atoms, OH, =O other than at alpha position, $S(O)_nR_{24}$, $NR_5R_6$, alkenyl of 2–5 carbons, alkynyl of 2–5 carbons or cycloalkyl of 3–8 carbons;

$R_1$ is $C_1-C_4$ alkyl, optionally substituted with one or more halogen atoms, OH, CN, $NR_5R_6$ or $CO_2R_8$; $C_2-C_4$ alkenyl; $-NR_9R_{10}$; $-N_3$;

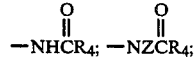

$-NX_2$; $NR_9X$ $--NXZ+$;

$R_2$ and $R_3$ are independently $C_1-C_2$ alkyl or, taken together are $-(CH_2)_9-$;

$R_4$ is alkyl of 1–4 carbons, optionally substituted with one or more halogens;

$R_5$ and $R_6$ are independently H, alkyl of 1–4 carbons or cycloalkyl of 3–8 carbons;

$R_7$ is $-NR_5R_6$, $-OR_5$ or

$R_8$ is H or alkyl of 1–4 carbons;

$R_9$ is H, $C_1-C_4$ alkyl or $C_3-C_8$ cycloalkyl;

$R_{10}$ is H, $C_1$-$C_4$ alkyl, $C_2$-$C_4$ alkenyl, $C_3$-$C_4$ cycloalkyl, —$OR_8$ or —$NR_{11}R_{11A}$;

$R_{11}$ and $R_{11A}$ are independently H or $C_1$-$C_4$ alkyl, or taken together, are —$(CH_2)_r$—;

X is Cl, Br or I;

Y is H, F, Cl, Br, alkyl of 1-3 carbons, or $NO_2$, or A and Y taken together can be —O—$(CH_2)_t$O—;

Z is a physiologically acceptable cation;

n is 0, 1 or 2;

p is 0 or 1;

q is 3, 4 or 5;

r is 4 or 5;

t is 1, 2 or 3;

B is —$NH_2$,

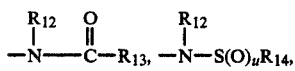

or $N_3$;

$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; —$CH_2OR_{15}$; —$CH(OR_{16})OR_{17}$; —$CH_2S(O)_vR_{14}$;

—$OR_{18}$; —$SR_{14}$; —$CH_2N_3$; the aminoalkyl groups derived from α-amino acids such as glycine, L-alanine, L-cysteine, L-proline, and D-alanine; —$NR_{19}R_{20}$; or $C(NH_2)R_{21}R_{22}$;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —$(CH_2)_m$—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —$(CH_2)_s$—;

u is 1 or 2;

v is 0, 1 or 2;

m is 2 or 3;

s is 2, 3, 4 or 5; and $R_{23}$ is H, alkyl of 1-8 carbons optionally substituted with one or more halogens, or cycloalkyl of 3-8 carbons;

$R_{24}$ is alkyl of 1-4 carbons or cycloalkyl of 3-8 carbons;

$R_{25}$ is alkyl of 1-4 carbons substituted with one or more of —$S(O)_nR_{24}$, —$OR_8$,

—$NR_5R_6$, or alkenyl of 2-5 carbons optionally substituted with CHO; or a pharmaceutically suitable salt thereof; provided that:

(1) when A is $CH_3S$—, then B is not

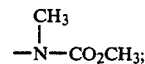

(2) when A is $CH_3SO_2$—, then B is not

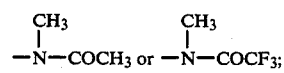

(3) when A is $H_2NSO_2$— and B is

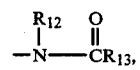

then $R_{12}$ is H;

(4) when A is —CN, B is not —$N_3$;

(5) when A is $(CH_3)_2CH$, B is not $NHCOCH_2Cl$;

(6) when A is $OR_5$, then B is not $NH_2$;

(7) when A is F, then B is not $NHCO_2CH_3$.

Preferred, for their high antibacterial activity or ease of synthesis, or both, are compounds of formula I where:

(1) Y is H;

A, substituted in the para position, is —$S(O)_nR_1$, $NO_2$,

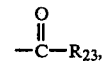

—$CH(CH_3)_2$, —$CH_2CH_3$, $CH_3CH(OH)$—, or —$COCH_2OCOCH_3$;

$R_1$ is $C_1$-$C_2$ alkyl optionally substituted with one or more halogen atoms or $NR_5R_6$;

$R_5$ is H or $CH_3$;

$R_6$ is H or $CH_3$;

$R_{23}$ is alkyl of 1-3 carbons; and n is 0, 1 or 2 when $R_1$ is alkyl or substituted alkyl; n is 2 when $R_1$ is $NR_5R_6$; or (2) B is

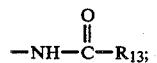

$R_{13}$ is H, $CH_3$, $OR_{18}$, $CHCl_2$, $CH_2Cl$ or $CH_2OR_{15}$;

$R_{15}$ is H or $C_1$-$C_4$ alkyl; and $R_{18}$ is $C_1$-$C_4$ alkyl.

Preferred because of high antibacterial activity are compounds of formula I having the absolute configuration depicted:

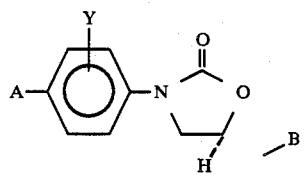

More preferred because of high antibacterial activity are compounds of formula I having the absolute configuration depicted:

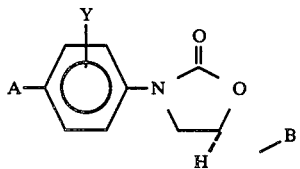

and where A is $S(O)CH_3$, $SCH_3$, $S(O)_2CH_3$, $SO_2NH_2$, $COR_{23}$ ($R_{23}$ is preferably alkyl of 1–3 carbons), $CH(CH_3)_2$, $CH_3CH_2$—, $CH_3CH(OH)$—, or —$COCH_2OCOCH_3$; and where B is —$NHCOCH_3$, —$NHCO_2CH_3$ or —$NHCOCHCl_2$.

Specifically preferred for their high antibacterial activity are the following compounds:

(l)-N-[3-[4-(methylsulfonyl)phenyl]-2-oxooxazolidin-5-ylmethyl]carbamic acid, methyl ester;

(l)-N-[3-[4-(methylthio)phenyl]-2-oxooxazolidin-5-ylmethyl]carbamic acid, methyl ester;

(l)-N-[3-[4-(methylsulfonyl)phenyl]-2-oxooxazolidin-5-ylmethyl]formamide;

(l)-N-[3-[4-(methylsulfonyl)phenyl]-2-oxooxazolidin-5-ylmethyl]acetamide;

(l)-N-[3-[4-(methylthio)phenyl]-2-oxooxazolidin-5-ylmethyl]acetamide;

(l)-N-[3-[4-(aminosulfonyl)phenyl]-2-oxooxazolidin-5-ylmethyl]acetamide;

(l)-N-[3-[4-(methylsulfinyl)phenyl]-2-oxooxazolidin-5-ylmethyl]acetamide including R,S isomer, S,S isomer and mixtures thereof);

(l)-2,2-dichloro-N-[3-[4-(methylsulfonyl)phenyl]-2-oxooxazolidin-5-ylmethyl]acetamide;

(l)-N-[3-(4-isopropylphenyl)-2-oxooxazolidin-5-ylmethyl]acetamide;

(l)-N-[3-(4-acetylphenyl)-2-oxooxazolidin-5-ylmethyl]acetamide;

(l)-N-[3-[4-(1-hydroxyethyl)phenyl]-2-oxooxazolidin-5-ylmethyl]acetamide;

l-N-[3-(4-ethylphenyl)-2-oxooxazolidin-5-ylmethyl]acetamide;

l-N-[3-[3-(4-acetyloxyacetyl)phenyl]-2-oxooxazolidinyl-5-ylmethyl]acetamide;

l-N-[2-oxo-3-[4-(1-oxobutyl)phenyl]-5-oxazolidinylmethyl]acetamide; and l-N-[2-oxo-3-[4-(1-oxopropyl)phenyl]-5-oxazolidinylmethyl]acetamide.

Another aspect of this invention relates to novel intermediates having the formula:

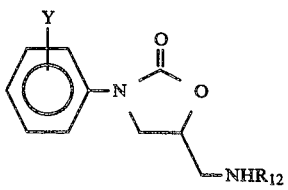

wherein, for the l, and mixtures of the d and l stereoisomers of the compound, $R_{12}$ is H, $C_1$–$C_{20}$ alkyl or $C_3$–$C_8$ cycloalkyl; and Y is H, F, Cl, Br or $NO_2$ (preferably H).

Another aspect of this invention relates to novel intermediates having the formula:

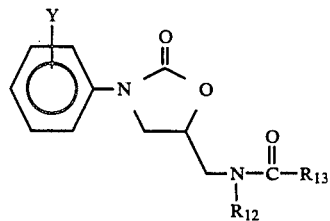

wherein, for the l, and mixtures of the d and l stereoisomers of the compound,

Y is as directly above;

$R_{12}$ is H, $C_1$–$C_{10}$ alkyl or $C_3$–$C_8$ cycloalkyl;

$R_{13}$ is H; $C_1$–$C_4$ alkyl optionally substituted with one or more halogen atoms; $C_2$–$C_4$ alkenyl; $C_3$–$C_4$ cycloalkyl; phenyl; —$CH_2OR_{15}$; —$CH(OR_{16})OR_{17}$; —$CH_2S(O)_vR_{14}$;

$$\overset{O}{\underset{}{\|}}\\CR_{15};$$

—$OR_{18}$; —$SR_{14}$; the aminoalkyl groups derived from α-amino acids such as glycine, L-alanine, L-cysteine, L-proline, and D-alanine; —$NR_{19}R_{20}$; or $C(NH_2)R_{21}R_{22}$;

$R_{14}$ is $C_1$–$C_4$ alkyl, optionally substituted with one or more halogen atoms;

$R_{15}$ is H or $C_1$–$C_4$ alkyl, optionally substituted with one or more halogen atoms;

$R_{16}$ and $R_{17}$ are independently $C_1$–$C_4$ alkyl or, taken together, are —$(CH_2)_m$—;

$R_{18}$ is $C_1$–$C_4$ alkyl or $C_7$–$C_{11}$ aralkyl;

$R_{19}$ and $R_{20}$ are independently H or $C_1$–$C_4$ alkyl;

$R_{21}$ and $R_{22}$ are independently H, $C_1$–$C_2$ alkyl, $C_3$–$C_6$ cycloalkyl, phenyl or, taken together, are —$(CH_2)_s$—;

m is 2 or 3; and v is 0, 1 or 2; and s is 2, 3, 4 or 5.

Another aspect of this invention relates to a pharmaceutical composition comprising a suitable pharmaceutical carrier and an antibacterially effective amount of a compound having the formula shown below. Yet another aspect of the invention relates to a method for alleviating bacterial infection in a mammal which comprises administering to the mammal an antibacterially effective amount of a compound having the formula:

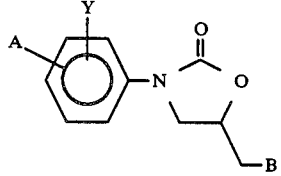

wherein, for the l, and mixtures of the d and l stereoisomers of the compound,

A is —$NO_2$, —$S(O)_nR_1$, —$S(O)_2$—$N$=$S(O)_pR_2R_3$, —SH,

A is —$NO_2$, —$S(O)_nR_1$, —$S(O)_2$—$N$=$S(O)_pR_2R_3$, —SH,

-continued

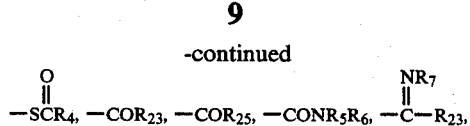

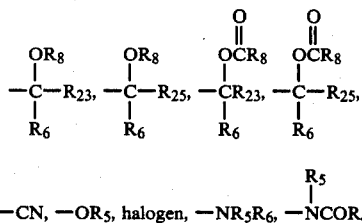

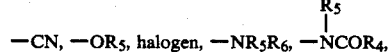

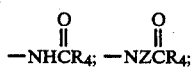

alkyl of 1 to 8 carbons, optionally substituted with one or more halogen atoms, OH, =O other than at alpha position, $S(O)_nR_{24}$, $NR_5R_6$, alkenyl of 2-5 carbons, alkynyl of 2-5 carbons or cycloalkyl of 3-8 carbons;

$R_1$ is $C_1$-$C_4$ alkyl, optionally substituted with one or more halogen atoms, OH, CN, $NR_5R_6$ or $CO_2R_8$; $C_2$-$C_4$ alkenyl; —$NR_9R_{10}$; —$N_3$;

—$NX_2$; $NR_9X$ —$NXZ^+$;

$R_2$ and $R_3$ are independently $C_1$-$C_2$ alkyl or, taken together are —$(CH_2)_q$—;

$R_4$ is alkyl of 1-4 carbons, optionally substituted with one or more halogens;

$R_5$ and $R_6$ are independently H, alkyl of 1-4 carbons or cycloalkyl of 3-8 carbons;

$R_7$ is —$NR_5R_6$, —$OR_5$ or $$\underset{NHCR_5;}{\overset{O}{\|}}$$

$R_8$ is H or alkyl of 1-4 carbons;
$R_9$ is H, $C_1$-$C_4$ alkyl or $C_3$-$C_8$ cycloalkyl;
$R_{10}$ is H, $C_1$-$C_4$ alkyl, $C_2$-$C_4$ alkenyl, $C_3$-$C_4$ cycloalkyl, —$OR_8$ or —$NR_{11}R_{11A}$;
$R_{11}$ and $R_{11A}$ are independently H or $C_1$-$C_4$ alkyl, or taken together, are —$(CH_2)_r$—;
X is Cl, Br or I;
Y is H, F, Cl, Br, alkyl of 1-3 carbons, or $NO_2$, or A and Y taken together can be —O—$(CH_2)_tO$—;
Z is a physiologically acceptable cation;
n is 0, 1 or 2;
p is 0 or 1;
q is 3, 4 or 5;
r is 4 or 5;
t is 1, 2 or 3;
B is —$NH_2$,

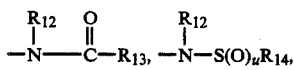

or $N_3$;
$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms;
$C_2$-$C_4$ alkenyl; $C_3$-$C_4$ cycloalkyl; phenyl;
—$CH_2OR_{15}$; —$CH(OR_{16})OR_{17}$; —$CH_2S(O)_pR_{14}$;

—$OR_{18}$; —$SR_{14}$; —$CH_2N_3$; the aminoalkyl groups derived from α-amino acids such as glycine, L-alanine, L-cysteine, L-proline, and D-alanine; —$NR_{19}R_{20}$; or $\cdot C(NH_2)R_{21}R_{22}$;

$R_{14}$ is $C_1$-$C_4$ alkyl, optionally substituted with one or more halogen atoms;
$R_{15}$ is H or $C_1$-$C_4$ alkyl, optionally substituted with one or more halogen atoms;
$R_{16}$ and $R_{17}$ are independently $C_1$-$C_4$ alkyl or, taken together, are —$(CH_2)_m$—;
$R_{18}$ is $C_1$-$C_4$ alkyl or $C_7$-$C_{11}$ aralkyl;
$R_{19}$ and $R_{20}$ are independently H or $C_1$-$C_2$ alkyl;
$R_{21}$ and $R_{22}$ are independently H, $C_1$-$C_4$ alkyl, $C_3$-$C_6$ cycloalkyl, phenyl or, taken together, are —$(CH_2)_s$—;
u is 1 or 2;
v is 0, 1 or 2;
m is 2 or 3;
s is 2, 3, 4 or 5; and
$R_{23}$ is H, alkyl of 1-8 carbons optionally substituted with one or more halogens, or cycloalkyl of 3-8 carbons;
$R_{24}$ is alkyl of 1-4 carbons or cycloalkyl of 3-8 carbons;
$R_{25}$ is alkyl of 1-4 carbons substituted with one or more of —$S(O)_nR_{24}$, —$OR_8$,

—$NR_5R_6$, or alkenyl of 2-5 carbons optionally substituted with CHO; or a pharmaceutically suitable salt thereof; provided that:

(1) when A is $CH_3S$—, then B is not

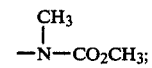

(2) when A is $CH_3SO_2$—, then B is not

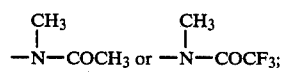

(3) when A is $H_2NSO_2$— and B is

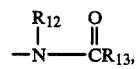

then $R_{12}$ is H;
(4) when A is —CN, B is not —$N_3$;
(5) when A is $(CH_3)_2CH$, B is not $NHCOCH_2Cl$;
(6) when A is F, then B is not $NHCO_2CH_3$.

DETAILED DESCRIPTION

The compounds of formulae I, Ia, and Ib contain at least one chiral center, and as such exist as two individual isomers or as a mixture of both. This invention relates to the levorotatory isomer (l) which for many of the compounds in this invention can be referred to as the (S) isomer, as well as mixtures containing both the d and the l isomers which can be referred to as mixtures containing both the (R) and (S) isomers. An additional chiral center is present when A is $R_1S(O)_n$ and n is 1 and this invention relates to both of the possible isomers at that center. Additional chiral centers may be present in the groups A and/or B and this invention relates to all possible stereoisomers in these groups.

For the purposes of this invention, the l-isomer of compounds of formulae I, Ia, and Ib is intended to mean compounds of the configuration depicted; when B is NHAc, and closely related groups, this isomer is described as the (S)-isomer in the Cahn-Ingold-Prelog nomenclature;

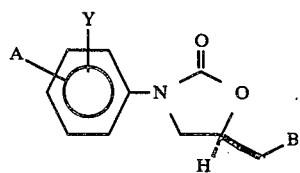

Synthesis

Compounds of Formula (I) can be prepared as follows:

Scheme 1:

Where $R_z$ may be 4-tolyl, phenyl, 4-chlorophenyl, $C_1$-$C_4$ alkyl or haloalkyl, such as trifluoromethyl.

When the synthetic path (a) is used, the group A may be —H or any of the groups previously shown except where $R_1$ is —$N_3$, —$NX_2$, —$NR_9X$, —$^-NXZ^+$. When the synthetic path (b) is used the group A may be —H or any of the groups previously shown except when A is $R_1S(O)_n$ and $R_1$ is $NR_9R_{10}$, $R_9$, $R_{10}$, $R_{11}$, and $R_{11A}$ cannot be H.

Compounds of Formula (II) may be converted to sulfonate esters (III) by reaction with the appropriate sulfonyl halide or sulfonic anhydride in a solvent plus a base or in a basic organic solvent such as pyridine. It is desirable when the A group has a sulfonamide hydrogen to use pyridine or other mildly basic solvents such as the picolines or collidines. As solvents, 1,2-dimethoxyethane, dioxane, bis-(2-methoxyethyl)ether, N,N-dimethylformamide (DMF), N,N-dimethylacetamide (DMAc), acetonitrile, or tetramethylenesulfone may be used. As a base, triethylamine, N-methylmorpholine, tributylamine or one of the heterocyclic bases can be used.

Compounds (III) may be reacted with sodium, potassium, lithium, cesium or rubidium azides in a dipolar aprotic solvent such as DMF, N-methylpyrrolidone, DMAc, sulfolane, dimethylsulfoxide, tetramethylurea, hexamethylphosphoramide (HMPA), etc. along with the appropriate catalyst such as 18-crown-6 for sodium and potassium azide and 12-crown-4 for lithium azide.

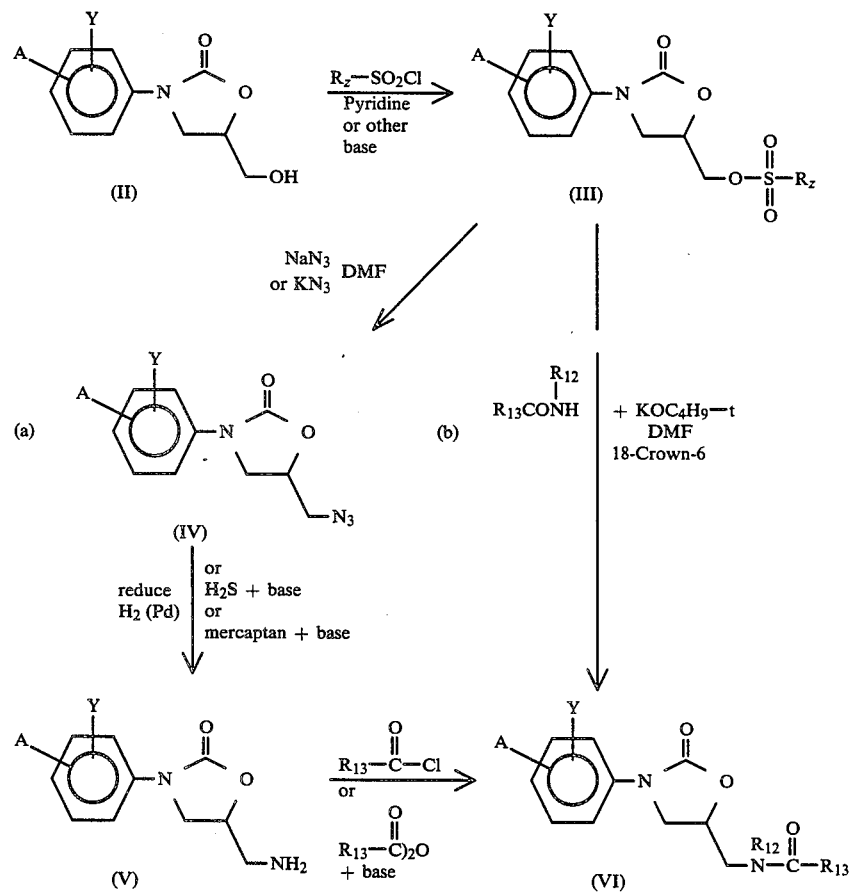

This reaction is carried out from about 60° to 125° C., with the preferred temperatures being 70° to 90° C. The products are azides of structure (IV).

Alternatively, alcohols of Formula (II) may be converted directly to the azides of Formula (IV) by reaction with diphenoxyphosphonylazide and triphenylphosphine in the presence of an equivalent of diethylazodicarboxylate in a solvent such as tetrahydrofuran, 1,2-dimethoxyethane, bis-(2-methoxyethyl)ether, toluene or benzene. The reaction is carried out under anhydrous conditions at temperatures between room temperature and 80° C.

The azides (IV) may be reduced by any of several methods, such as hydrogenation with palladium-on-charcoal or with platinum catalyst. It is also possible to reduce the azides by treating with 1,3-propanedithiol and a base such as triethylamine. Azides may also be reduced to amines by hydrogen sulfide and by trivalent phosphorous compounds such as trimethylphosphine and trimethylphosphite, and by mercaptans such as mercaptoacetic acid. Reduction with hydrogen can be used where A is a functional group resistant to hydrogenation or hydrogenolysis. The reduction is carried out using a solvent such as ethanol, methanol, 1,2-dimethoxyethane, acetic acid, trifluoroacetic acid, or isopropanol. A solution may be stirred at ambient temperature with palladium-on-charcoal catalyst or Adams catalyst present and the hydrogen introduced at atmospheric pressure through a glass frit. In some instances the reduction is exothermic.

The reduction using 1,3-propanedithiol is carried out in methanol or other alcohol solvents containing an equivalent of triethylamine, by warming until $N_2$ evolution occurs. At ambient temperatures, slow reduction occurs. Temperatures of 20° to 100° C. may be used; temperatures of 40° to 60° C. are preferred. Warming an azide (IV) with trimethylphosphite causes a rapid evolution of $N_2$. The reaction may be carried out in 1,2-dimethoxyethane or bis-(2-methoxyethyl)ether and the crude intermediate, when hydrolyzed with water or acid, gives the desired amine (V).

The aminomethyl compounds (V) are acylated by reaction of the amine with an acid chloride or anhydride in a basic solvent such as pyridine or by reaction in a water miscible solvent such as THF or 1,2-dimethoxyethane in the presence of an aqueous base such as sodium hydroxide or potassium hydroxide, sodium bicarbonate or sodium carbonate. When pyridine is used as solvent for the reaction, the acid chloride or anhydride is added to the mixture at 0° to 10° C. The reaction may be carried out between −30° and 50° C. With very reactive acid chlorides or anhydrides such as trifluoromethanesulfonyl chloride or anhydride the reaction is preferably carried out at −60° to −40° C. The acylations using aqueous bases are done by stirring the amine (V) in a water miscible solvent such as tetrahydrofuran (THF), 1,2-dimethoxyethane, or dioxane and adding 1–5N NaOH to keep the mixture basic as the acid chloride or anydride is added, while keeping the temperature between −5° and 20° C. The compounds (V) can also be acylated by any of the standard peptide synthesis methods where the free acid is reacted with the amine using N,N-dicyclohexylcarbodiimide, or where a mixed anhydride is first formed from the acid using a chloroformate ester and a tertiary base such as triethylamine, followed by reaction with the amine. In the mixed anhydride procedure, the acid to be used is allowed to react with a chloroformate such as ethyl chloroformate or isobutyl chloroformate in a solvent such as THF, DMF or 1,2-dimethoxyethane, in the presence of a tertiary base such as triethylamine or N-methylmorpholine at −30° to 10° C. To this mixture the amine (V) is added and the mixture stirred at −10° C. for 1-5 hours. When N,N-dicyclohexylcarbodiimide is used as the condensing agent, the conditions and solvents may be the same but it is often advantageous to add N-hydroxyphthalimide or N-hydroxysuccinimide.

Further, these amines may be acylated by reaction with esters such as methyl dichloroacetate, ethyl trifluoroacetate or n-butyl formate. In this method, the amine (V) is combined with the ester and a solvent such as 1,2-dimethoxyethane, bis-(2-methoxyethyl)ether, or toluene (in some cases the ester may be used as the solvent) and the mixture is heated at reflux until the reaction is shown to be complete by an assay such as thin-layer chromatography. More reactive esters such as p-nitrophenyl esters, pentafluorophenyl esters, thio esters, enol esters, N-hydroxyphthalimide esters, N-hydroxysuccinimide esters, 1-hydroxybenzotriazole esters, 2,4,5-trichlorophenyl esters, and pentachlorophenyl esters, may be used. Further, other acylating agents such as acyl azides, acyl imidazoles and acyl phosphates, may be used.

When synthetic path (b) is used, the sulfonate ester (III) is allowed to react with an amide in the form of its sodium or potassium salt, generated using NaH, KH or $KOC_4H_9$—t in a dipolar aprotic solvent such as DMF, DMAc, HMPA, N-methylpyrrolidinone, or tetramethylenesulfone. To the salt preparation is added the sulfonate ester (III) and the mixture is heated to 30° to 150° C. A catalyst such as 18-crown-6 may be used. Heating is continued for 3–50 hours.

In Scheme 1, the starting compound (II) may be dl-(the racemate) or the l-isomer. The l-isomer is a precursor for the preferred l-amides (VI).

When the acylating group is derived from an α-amino acid and $R_{13}$ contains an amino function it is necessary to protect that amino function with one of the commonly used protective groups such as benzyloxycarbonyl, t-butyloxycarbonyl, 9-fluorenylmethyloxycarbonyl, or phthaloyl. Following the acylation, the protective group is removed by one of the standard methods to which the oxazolidinone ring is inert. The benzyloxycarbonyl group may be removed by hydrogenation in a solvent such as methanol, DMF, acetic acid, or mixtures of these solvents, using a catalyst such as 10% palladium-on-carbon or palladium black (100 to 500 mg of catalyst per mmole of compound). Alternatively the benzyloxycarbonyl group may be removed by dissolving the compound in acetic acid, adding an equal volume of 4N HBr in acetic acid, and keeping the solution at room temperature for 1 to 5 hours. The $N^{\alpha}$-t- butyloxycarbonyl groups are removed by hydrolysis with trifluoroacetic acid at room temperature.

Scheme 2:

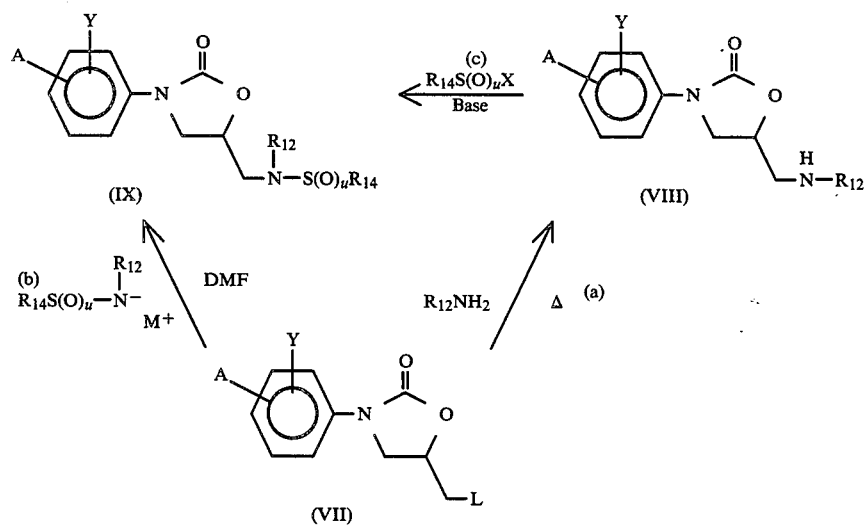

Compounds of formula (I) which may be made using the procedures of Scheme 1 are those where A is H or any of the groups previously shown except that when A is $R_1S(O)_n$ and $R_1$ is $NR_9R_{10}$, $R_9$, $R_{10}$, $R_{11}$ and $R_{12}$ cannot be H. L may be any suitable leaving group such as I, Br, Cl, benzenesulfonyloxy, 4-toluenesulfonyloxy, methanesulfonyloxy or trifluoromethanesulfonyloxy. In route (a) the compound (VII) is allowed to react with ammonia or an amine in a solvent such as ethanol at temperatures of 50° to 150° C. Where the amine or solvent is low-boiling, the reaction is carried out in a sealed vessel to allow the desired temperature to be reached. The solvent may be ethanol, DMF, DMAc, N-methylpyrrolidinone, tetramethylenesulfone, tetrahydrofuran, acetonitrile, or HMPA. The reaction time may be 1 to 24 hours. When A or Y contains a halogen, carbonyl, ester, or nitro group, route (a) may give undesired side reactions so the azide route described in Scheme 1 is used. Where (VII) is optically active (i.e., the l-isomer) the product is optically active. The acylation of product VIII is carried out as described for Scheme 1, Path (a).

The reaction of (VII) with the anion of a sulfonamide shown in Scheme 2, Path (b) is carried out in a polar solvent such as DMF, DMAc, N-methylpyrrolidinone, tetramethylenesulfone, or HMPA. In some cases the use of a catalyst such as 18-crown-6 may improve the reaction. Temperatures of 50° to 150° C. are employed; the time for the reaction can vary between 2 to 48 hours.

Alternatively, the sulfonamides (IX) can be prepared by reaction of the amine (VIII) with a sulfonyl halide in the presence of a base such as triethylamine or basic solvent such as pyridine [Path (c)].

Scheme 3:

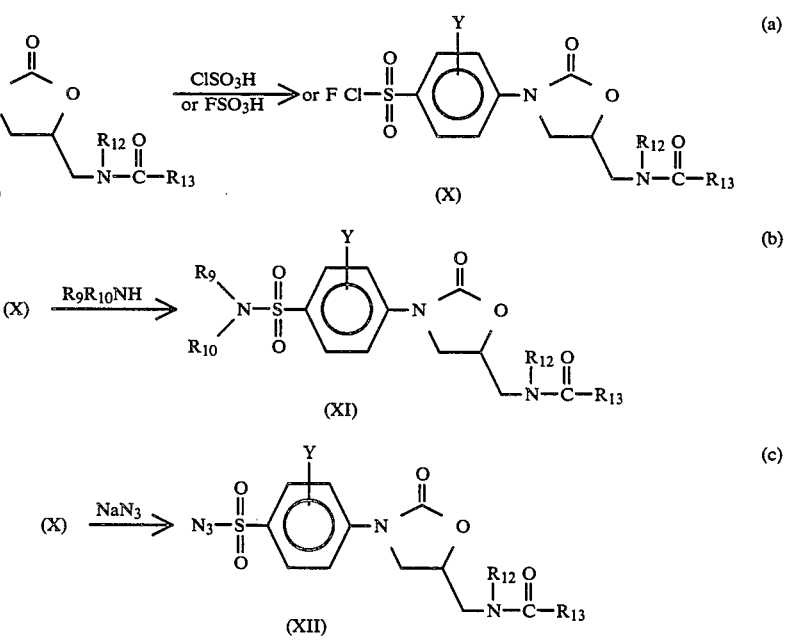

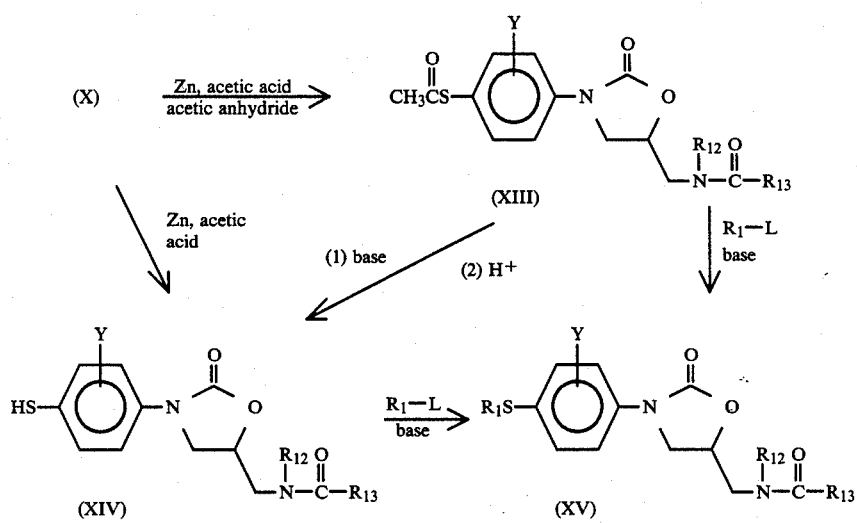

Compounds of Formula I, where B is

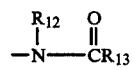

wherein $R_{13}$ is not $CH(OR_{16})OR_{17}$ or $CH_2N_3$ can be prepared as shown in Scheme 3. The halosulfonation (particularly, chlorosulfonation) shown in Scheme 3, Path (a), can be carried out by adding the compound of formula VI where A is H to chlorosulfonic acid or fluorosulfonic acid at room temperature in the absence of solvent. The temperature may be $-10°$ to $100°$ C.; preferred temperatures are $15°$ to $35°$ C. A solvent inert to chlorosulfonic acid or fluorosulfonic acid may be employed (examples include carbon tetrachloride, nitrobenzene, or a fluorocarbon) but using neat chlorosulfonic acid or fluorosulfonic acid is preferred.

The sulfonyl chloride or fluoride (X) may then be reacted by the procedure of Scheme 3, Path (b), with ammonia, a mono- or disubstituted amine, a hydroxylamine or a hydrazine in a solvent such as THF, 1,2-dimethoxyethane, dioxane, bis-(2-methoxyethyl)ether or DMF. The reaction may be run at temperatures of $-20°$ to $40°$ C.; temperatures of $-10°$ to $10°$ C. are preferred.

The sulfonyl chloride or fluoride (X), may be reacted with sodium azide or potassium azide in a mixture of acetone and water to give the sulfonyl azide (XII) as shown in Scheme 3, Path (c). Other water-miscible solvents such as acetonitrile, DMF, 1,2-dimethoxyethane, THF, or dimethylsulfoxide may be used in place of acetone. An aqueous solution of sodium azide is added to acetone, the mixture is cooled in an ice-bath, the sulfonyl halide (X) is added, and the mixture is allowed to come to room temperature. The reaction may be carried out at $-10°$ to $20°$ C. Preferred temperatures are $-5°$ to $10°$ C.

The sulfonyl chlorides (X), except when Y is nitro, may be reduced by several methods, as shown in Scheme 3, path (d). The use of zinc metal added to a hot mixture of acetic acid, acetic anhydride and sodium acetate gives the S-acetates (XIII) in good yield. This is carried out at reflux temperature of the mixture, but may be carried out between $50°$ C. to reflux. Alternatively, the sulfonyl halides may be reduced by using zinc in acetic acid to give the mercaptans (XIV). The reduction may also be carried out using an iodide such as trimethylsilyl iodide or mixtures of trimethylsilyl chloride and sodium iodide in an inert solvent such as dichloromethane, benzene or toluene; stirring in the temperature range of $0°$ C. to $50°$ C. with the preferred temperature $20°-30°$ C. This reduction gives the disulfide which is then reduced by sodium borohydride in an alcohol solvent such as methanol. The disulfide may also be reduced by dithiothreitol or by zinc and acid. The product is the mercaptans (XIV). If desired the mercaptans may be alkylated with the halides $R_1$—L to give the sulfides (XV). Preferred, is to alkylate the S-acetates (XIII) directly with $R_1$—L to give the sulfides (XV). This reaction may be carried out using base such as potassium carbonate, sodium methoxide, sodium ethoxide or potassium t-butoxide in an alcohol solvent. The alkylation can be done using sodium hydroxide in dimethylsulfoxide.

The reactions of Scheme 3 may be carried out starting with the l-isomer of (VI) where A is H and Y is H, 3—F, 3—CH$_3$, or 3—CH$_3$CH$_2$— to give products of the preferred l-form (the preferred configuration shown above).

Scheme 4:

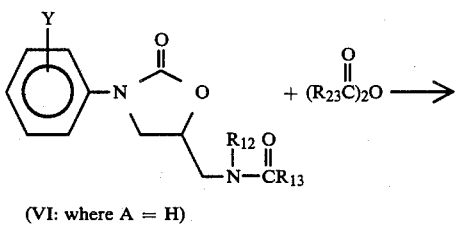

(VI: where A = H)

-continued

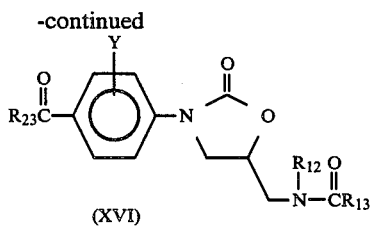
(XVI)

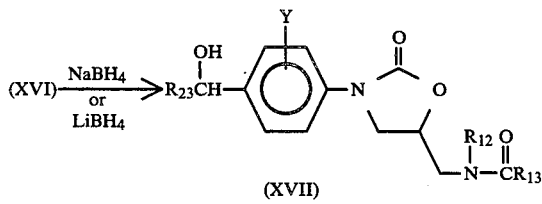
(XVII)

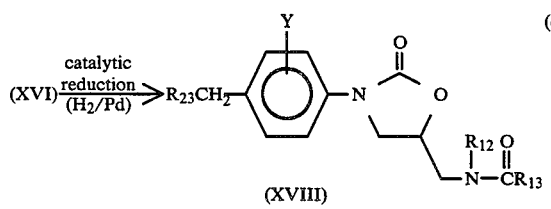
(XVIII)

The acylation of Scheme 4, Path a) is carried out by reacting the compounds of formula (VI)(A=H) with an excess of an acid anhydride in methanesulfonic acid. This acylation may be carried out at a temperature from room temperature to 70° C., over time periods of 2–10 hours. Alternatively, the acylation can be carried out with an appropriate carboxylic acid in the presence of a mixture of phosphorous pentoxide or methanesulfonic anhydride in methanesulfonic acid. The reaction may also be carried out using polyphosphoric acid or liquid hydrogen fluoride at temperatures of 40° to 100° C. During the reaction, the amide nitrogen may be simultaneously substituted with a second acyl group which is removed in the aqueous work-up or by treatment with an alcohol such as methanol.

Alternatively, the acylated compounds (VI) where $R_{12}$=H can be prepared from the azides (IV) where A=H by reaction with one or more equivalents of an appropriate anhydride in anhydrous methanesulfonic acid at temperatures ranging from 20° to 40° C. The acylation may also be carried out with an appropriate carboxylic acid in methanesulfonic anhydride. The azides (IV, A=$R_{23}$CO) may be reduced to amines (V) by reaction with a trivalent phosphorous compound such as trimethylphosphite, trimethylphosphine, triphenylphosphine, tributylphosphine or the like in a solvent such as 1,2-dimethoxyethane, tetrahydrofuran, isopropanol, or diglyme ® with warming to 40° to 100° C. Warming under the above conditions results in evolution of nitrogen. The intermediate phosphazine when hydrolyzed with aqueous acid gives the desired amine (V, where A=$R_{23}$CO). The amine can by acylated by reaction with an acid chloride or anhydride in a water miscible solvent such as THF or 1,2-dimethoxyethane in the presence of an aqueous base as previously shown in Scheme 1, path a).

The acylated compounds (XVI) may be reduced to the corresponding alcohol (XVII) as shown in Scheme 4, Path b). The reduction can be carried out using sodium borohydride in an alcohol solvent such as ethanol, or via other mild metal borohydride reagents such as lithium borohydride, lithium tri-t-butoxyaluminum hydride, tetramethylammonium borohydride or the like. Catalytic reduction of (XVI), as shown in Scheme 4, Path c) can be run in a Parr shaker employing a solvent such as ethanol, acetic acid or a mixture of these solvents, using a catalyst such as 10% palladium-on-carbon.

The reaction of Scheme 4 may be carried out starting with the l-isomer of (XVI) where A=H to give products of the preferred l-form.

Scheme 5:

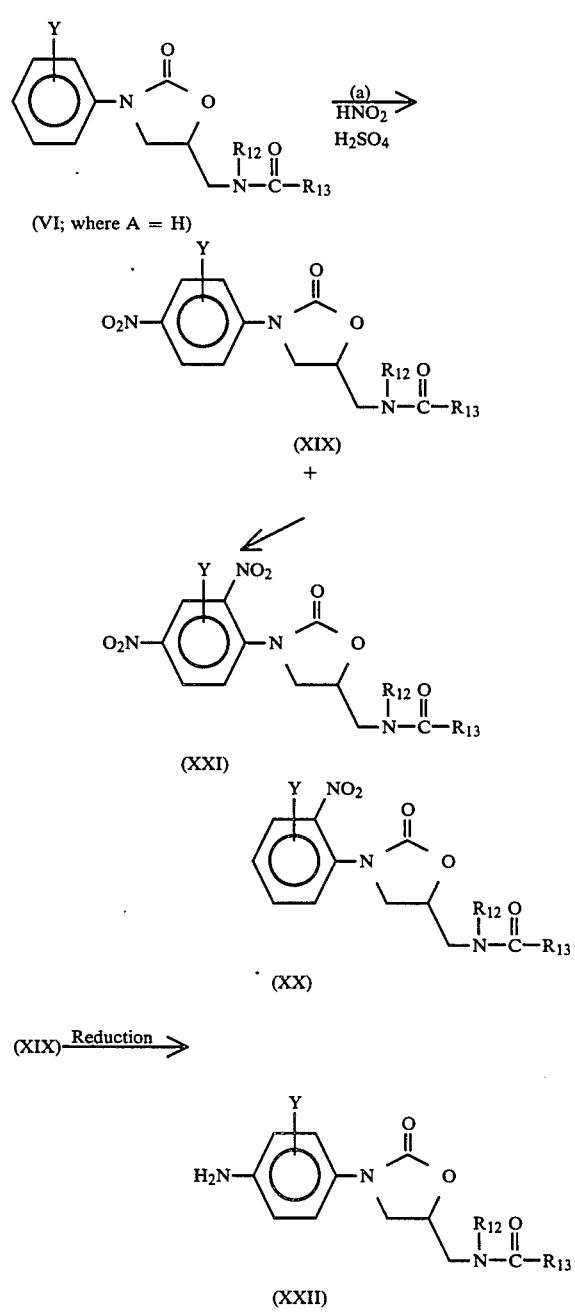

-continued

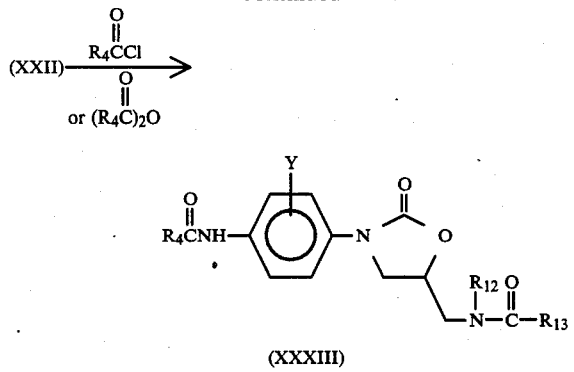

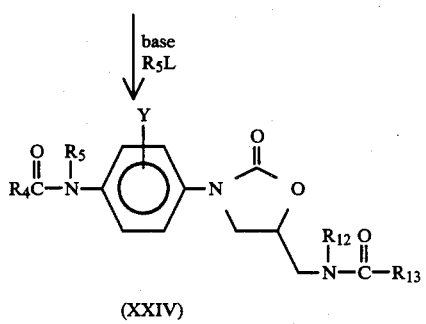

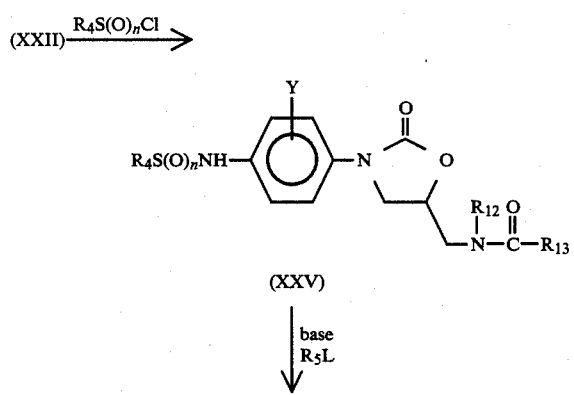

-continued

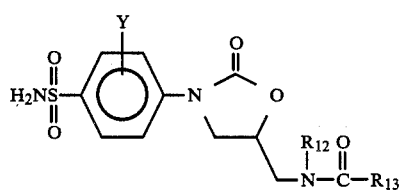

The nitration of Scheme 5, Path a) is carried out by adding the compound of formula (VI) where A=H and Y=H, 3-F, 3-methyl or 3-ethyl to concentrated sulfuric acid containing one equivalent of nitric acid. Nitrate may be added in the form of a salt such as potassium nitrate. The nitration mixture is cooled to about $-5°$ C., kept below $0°$ C. during the addition, and then allowed to warm to room temperature. The nitration may be carried out at temperatures of $-20°$ to $15°$ C., over time periods of 30 to 180 minutes.

In the nitration shown in Scheme 5 it has been found that some ortho nitration occurs as well as the formation of 2,4-dinitro-compound. These products may be isolated by use of preparative chromography, and/or crystallization. The ortho nitro compound may be made in higher amounts by nitration in acetic acid by generating acetyl nitrate. The dinitro-compound can easily be made by using a higher molar ratio of nitrating agent.

The nitro-compounds (XIX, XX, XXI) can be reduced by using Raney nickel catalyst and hydrazine or by catalytic hydrogenation in a Parr shaker under 10–50 lbs. of hydrogen using palladium-on-charcoal as the catalyst. The products are the anilines (XXII). The anilines (XXII) may be acylated using an acyl halide or an acyl anhydride in the presence of an organic base such as pyridine or triethylamine or N-methylmorpholine; or using aqueous sodium hydroxide in an organic solvent such as tetrahydrofuran, 1,2-dimethoxyethane or DMF. A catalyst such as 4-dimethylaminopyridine may be used. In a similar way the anilines may be reacted with a sulfonyl halide to give the sulfonamides. In turn, the amides (XXIII) and sulfonamides (XXV) may be alkylated using base and the appropriate alkyl halide, alkyl sulfonate or sulfate ester.

Compounds where $R_1$ is $-NX_2$, $-NR_4X$, $-NXZ$ or $-N=S(O)_pR_2R_3$ may be made as shown in Scheme 6.

Scheme 6:

(XI; $R_9$, $R_{10}$ = H)

(a) 2 eq. NaOX neutral 1 eq. ZOX (b)

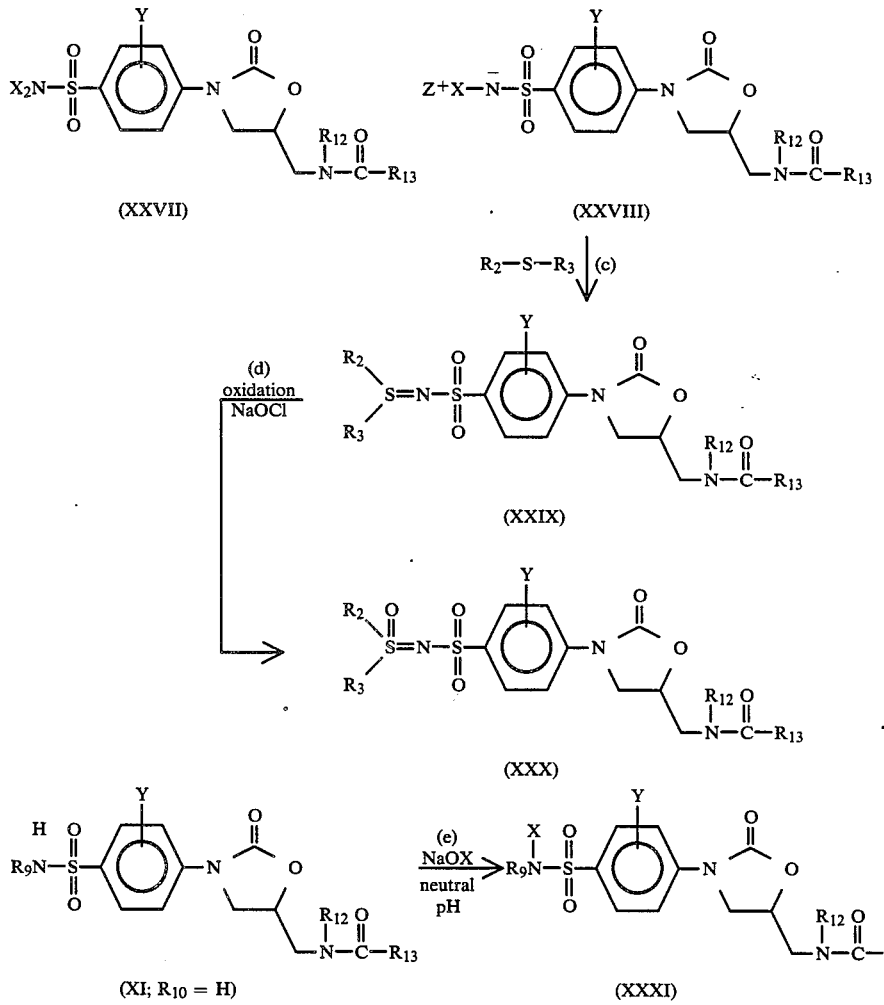

Part a) of Scheme 6 is carried out by adding the sulfonamide (XI; $R_9$, $R_{10}$=H) to 1.3-2N sodium or other hypohalite (2 equivalents) while keeping the pH between 6 and 7 by adding a dilute acid solution or acetic acid. This reaction may be carried out at $-20°$ to $50°$ C.; it goes well at room temperatures of $20°$ to $30°$ C. The reaction is complete in 30 minutes to 2 hours. To make the metal salts of the haloamide (XXVIII), Scheme 6, Path b), one keeps the solution basic and uses approximately an equivalent amount of the hypohalite.

The sulfilimines (XXIX) are made by reacting the haloamide (XXVIII) with the appropriate sulfide in an alcohol-water mixture at $50°$ to $70°$ C. These products may be converted to the sulfoximines by oxidation using an oxidant such as hypochlorite anion in a phase transfer catalyzed system. This oxidation is carried out by stirring (XXIX) in a mixed solvent (ethyl acetate and dichloromethane) with tetra-n-butylammonium bromide while a two-fold excess of aqueous NaOCl are added at room temperature.

The preparation of N-alkyl haloamides (XXXI) (Scheme 6, step e)) is carried out using the procedure of Scheme 6, Path a), except employing one equivalent of hypohalite.

An alternative synthesis of the glycinamides of Formula I where B is

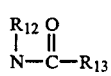

wherein $R_{13}$ is $CH_2NH_2$ as well as compounds where $R_{13}$ is $CH_2N_3$ is shown in Scheme 7.

Scheme 7:

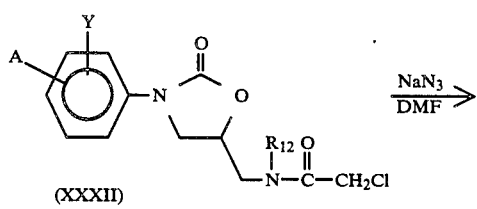

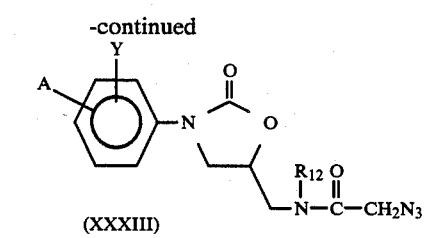

(XXXIII)

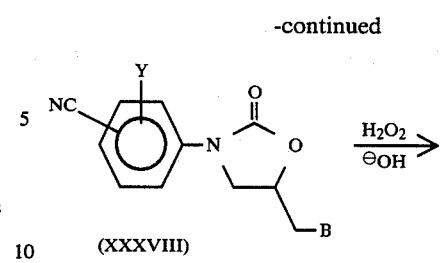

(XXXVIII)

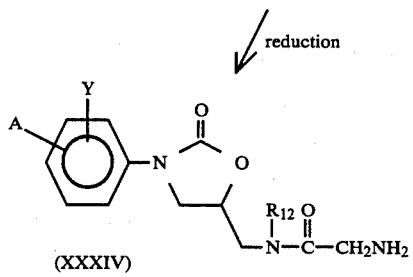

(XXXIV)

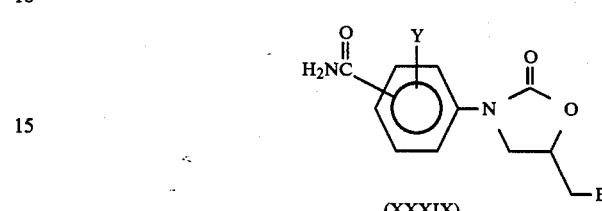

(XXXIX)

Glycine amides (XXXIV) may be prepared by making the chloroacetyl or bromoacetyl or iodoacetyl compounds (XXXII) followed by reacting these with sodium azide in dimethylsulfoxide or other dipolar aprotic solvents to give the azidoacetyl compounds (XXXIII). The azidoacetyl compounds then may be reduced by hydrogen using a palladium catalyst or by any of the other reduction methods such as 1,3-propanedithiol and triethylamine, thioglycolic acid, hydrogen sulfide, or trivalent phosphorous compounds. The products are the glycine amides (XXXIV).

The compounds of Formula I where A is $CR_{23}(OR_{16})OR_{17}$,

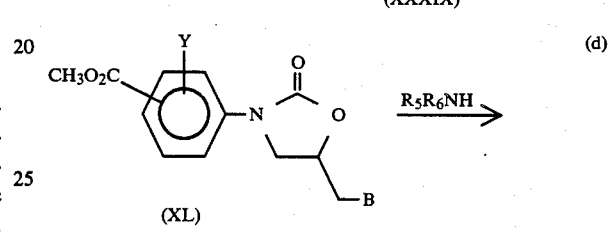

(XL)

$$\overset{NR_7}{\underset{CR_{23}}{\|}}, \text{ or } \overset{O}{\underset{CNR_5R_6}{\|}},$$

are obtained as shown in Scheme 8.

Scheme 8:

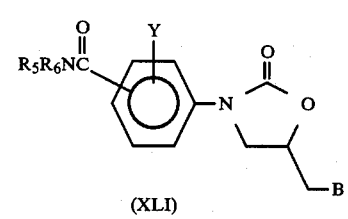

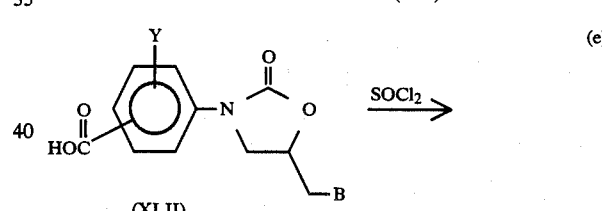

(XLI)

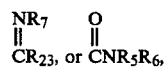

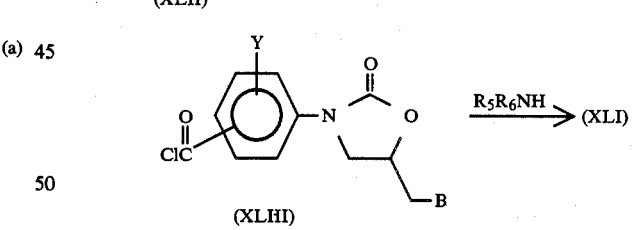

(XLII)

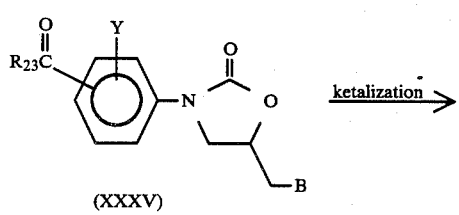

(XXXV)

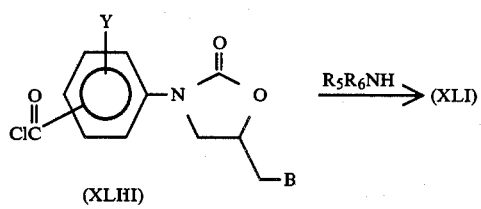

(XLIII)

Ketalization, as shown in Scheme 8, Path a) can be carried out by reacting the ketone derivative (XXXV) with an appropriate ortho ester in an alcohol solvent such as ethanol in the presence of an acid catalyst such as p-toluenesulfonic acid, sulfuric acid, methanesulfonic acid, boron trifluoride etherate or the like to give the corresponding dialkyl acetal. The reaction can be promoted by removing the ester by-product by distillation. Cyclic ketals can be prepared by treatment of the ketone or the corresponding thioacetal with ethylene glycol or 1,3-propanediol in an inert solvent such as benzene, toluene, or tetrahydrofuran in the presence of a catalytic amount of an organic acid such as p-toluenesulfonic acid, oxalic acid, adipic acid, or the like.

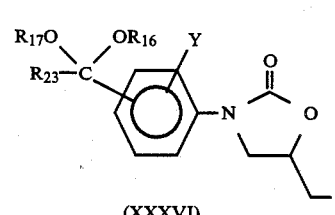

(XXXVI)

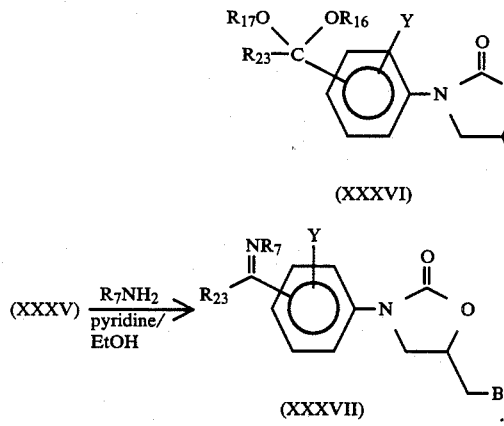

(XXXVII)

The acetals can also be prepared by formation of the requisite thioacetal via reaction with a mercaptan and an acid catalyst such as sulfuric acid, p-toluenesulfonic acid, hydrogen chloride, or boron trifluoride etherate. The mercaptals can be reacted with an appropriate alcohol or glycol to displace the mercaptan and give the desired acetals.

Reaction of the ketones (XXXV) with a hydroxylamine or hydrazine gives the corresponding oxime or hydrazone derivative (XXXVII). The reaction is carried out in a solvent mixture of pyridine in ethanol at a temperature of 50° C. to the reflux temperature of the solvent mixture. The hydrazone (XXXVII) where $R_7$=—$NHR_6$ may be acylated using an acyl halide or an acyl anhydride in the presence of an organic base such as pyridine or triethylamine in an organic solvent such as tetrahydrofuran or DMF. A catalyst such as 4-dimethylaminopyridine may be used.

The amides (XXXIX) can be prepared by hydrolysis of the nitriles (XXXVIII) with basic hydrogen peroxide. The reaction is conducted in aqueous alcoholic solvent at a temperature between 0° and 60° C. The substituted amides (XLI) can be prepared by aminolysis of the esters (XL). Alternatively, the carboxylic acids (XLII) can be treated with thionyl chloride to form an acid chloride of formula (XLIII) which can be treated with an amine ($R_5R_6NH$) to give a substituted amide (XLI). For higher boiling amines, a mixture of the amine and (XL) is stirred optionally in an alcoholic or polar aprotic solvent at a temperature of 50° to 150° C.

The carboxylic acid intermediates (XLII) where Y is hydrogen or halogen may be prepared by several methods. For example, the acetyl compounds of Formula (XVI) where $R_{23}$ is methyl, can be oxidized to the carboxyl functional group by use of sodium hypochlorite or sodium hypobromite followed by cleavage with a base such as sodium hydroxide. The haloform reaction can also be carried out with iodine and a base such as sodium hydroxide or potassium hydroxide. Alternatively, the acids (XLII) can be prepared from compounds of formula (VI) where A is a trifluoromethyl group by treatment with concentrated sulfuric acid at 0° to 35° C. followed by pouring the acid onto ice. The carboxylic acids (XLII) can also be prepared by oxidation of the aldehyde compounds of Formula (XVI) where $R_{23}$ is hydrogen with a mild oxidizing agent such as air, hypohalite, or permanganate.

Scheme 9:

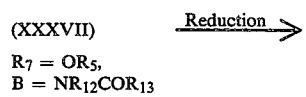

$R_7 = OR_5$,
$B = NR_{12}COR_{13}$

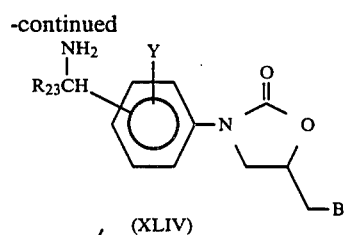

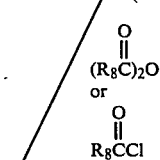

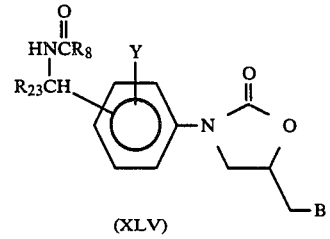

(XVII) $\xrightarrow[\text{or}]{SOCl_2}$ (b)
$\phi_3P/CCl_4$

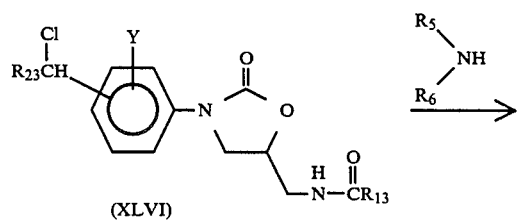

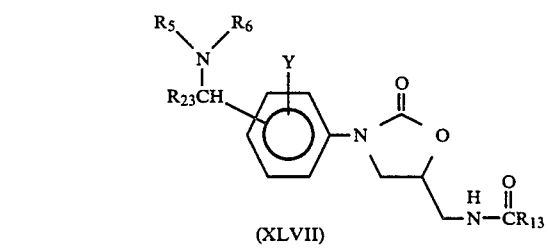

(XXXV; where B is $NR_{12}COR_{13}$)

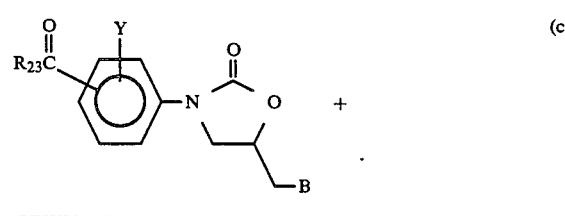

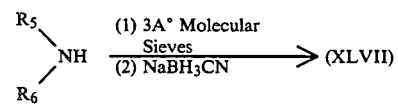

Amines (XLIV) can be prepared by reduction as shown in Scheme 9 from the oxime derivatives (XXXVII) using a reducing agent such as 10% palladium-on-carbon in a solvent such as acetic acid or an alcohol solvent such as ethanol. The amines (XLIV) may be acylated using an acyl anhydride or acyl halide in the presence of an organic base such as triethylamine or pyridine in an organic solvent such as methylene chloride or tetrahydrofuran. A catalyst such as 4-dimethylaminopyridine may be used.

A method for preparing secondary or tertiary amines (XLVII) is shown in Scheme 9, Path b) wherein the halo compound (XLVI) can be prepared from the alcohol by reaction with thionyl chloride. Alternatively, the alcohol can be reacted with triphenylphosphine in carbon tetrachloride or carbon tetrabromide. The halo compound (XLVI) can then be reacted with an amine. For low boiling amines, the reaction can be carried out under pressure. For higher boiling amines, a mixture of (XLVI) is stirred optionally in a polar aprotic solvent or an alcoholic solvent at a temperature of 50°–150° C.

Alternatively, the amines (XLVII) can be prepared by reductive amination as shown in Scheme 9, path c). By this method, the ketones or aldehydes (XXXV) can be reacted with ammonia or ammonium acetate or an amine of the formula $R_5R_6NH$ in the presence of 3A° molecular sieves followed by reduction via reaction with sodium cyanoborohydride. Other reducing agents such as zinc metal in an acid such as hydrochloric acid, hydrogen and a metal catalyst, or selenophenol and formic acid can be used instead of sodium cyanoborohydride.

An alternative synthesis of compounds of structure (V) is shown in Scheme 10.

Scheme 10:

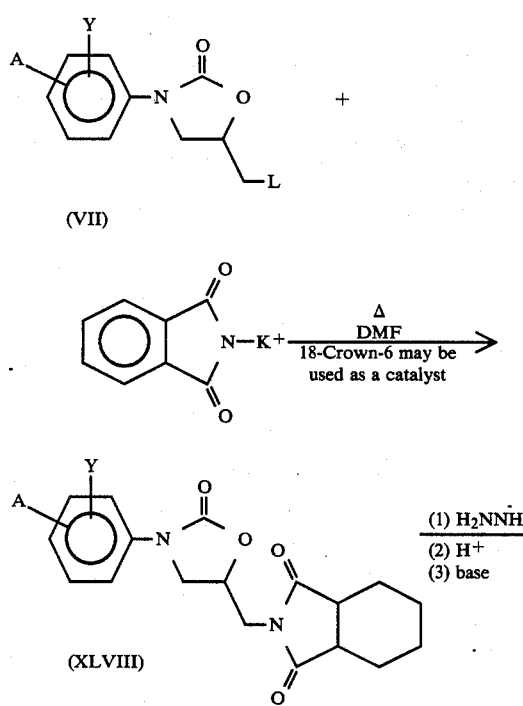

(VII)

(XLVIII)

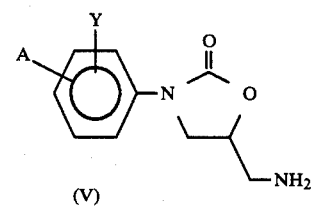

(V)

In Scheme 10, A may be H, or any of the groups previously shown except that when A is $R_1S(O)_n$, $R_1$ cannot be $N_3$, and when $R_1$ is $NR_9R_{10}$, $R_9$, $R_{10}$, $R_{11}$ and $R_{114}$ cannot be H. L may be any suitable leaving group such as I, Br, Cl, benzenesulfonyloxy, 4-toluenesulfonyloxy, methanesulfonyloxy, or trifluoromethanesulfonyloxy. The reaction is carried out by heating at temperatures of 25° to 150° C. in a dipolar aprotic solvent such as DMF, DMAc, N-methylpyrrolidinone, tetramethylenesulfone or HMPA. When L is trifluoromethanesulfonyloxy, the reaction is preferably carried out at low temperatures. The phthalimide group is then removed by treatment with an excess of hydrazine in alcohol at 20° C. to 50° C. for 5–30 hours followed by adjusting to neutral pH with acid. An alternate method is first to react (XLVIII) with sodium sulfide, then to dehydrate with N,N-dicyclohexylcarbodiimide, followed by reaction with hydrazine and then treatment with dilute acid. This last method is very mild.

Compounds where A is $-S(O)R_1$ or $-S(O)_2R_1$ may be made as shown in Scheme 11.

Scheme 11

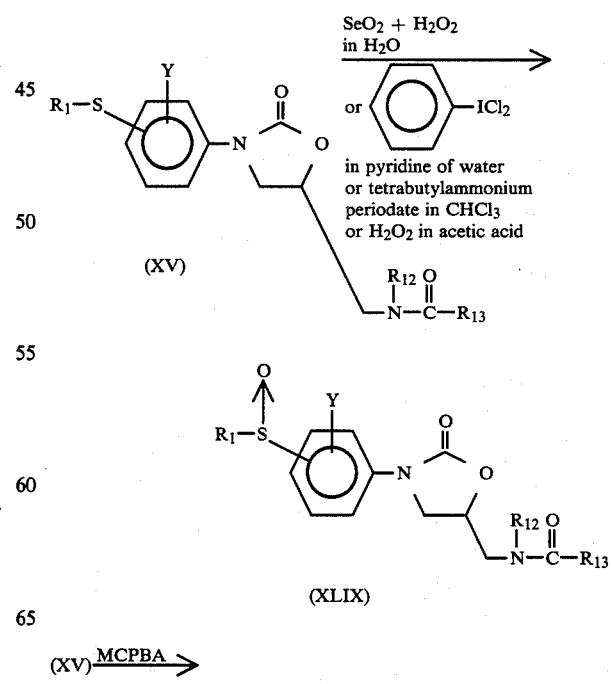

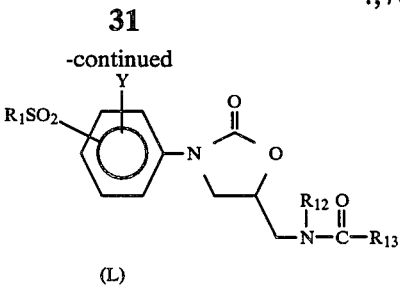

(L)

Sulfides of structure (XV) where $R_{12}$ and $R_{13}$ are as defined above may be oxidized to sulfoxides having the structure (XLIX) by using one equivalent of an oxidant. The preferred oxidation is carried out with hydrogen peroxide in acetic acid. Other oxidants which may be used include a water-solution of selenium dioxide containing hydrogen peroxide, iodobenzene dichloride in a pyridine-water mixture, or tetrabutylammonium periodate in refluxing chloroform. Strong oxidants such as m-chloroperoxybenzoic acid or peracetic acid may be used; the mixtures containing varying amounts of sulfide, sulfoxide and sulfone thus obtained may be separated by conventional techniques such as crystallization or chromatography.

Use of two equivalents of a strong oxidizing agent such as m-chloroperoxybenzoic acid results in the sulfone (L).

The products can be obtained as essentially pure isomers as is depicted in Scheme 12 by using the oxidation procedure described in P. Pitchen, E. Dunach, M. N. Deshanukh and H. B. Kagan, *J. Am. Chem. Soc.*, 106, 8188 (1984).

Scheme 12:

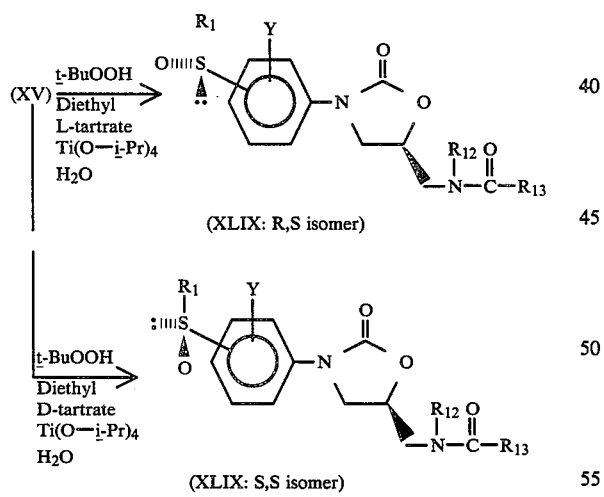

The (R,S) isomer (XLIX) is obtained from the sulfide (XV) by oxidation with 1.1 molar equivalents of tert-butyl hydroperoxide in the presence of a homogeneous solution of one molar equivalent of tetraisopropyl orthotitanate, and two molar equivalents of (+)-diethyl L-tartrate and one molar equivalent of water. The reaction is carried out in an inert solvent in which the sulfide (XV) has some solubility such as dichloromethane, chloroform, 1,2-dichloroethane, or tetrachloroethylene. Temperatures of −30° C. to −20° C. can be employed during the addition of the peroxide, followed by warming to room temperature. The reaction may take from 2–24 hours and if necessary additional tert-butyl hydroperoxide is added.

The (S,S) isomer (XLIX) is prepared in the same fashion using (−)-diethyl-D-tartrate instead of (+)-diethyl-L-tartrate.

Whenever a sulfide sulfur occurs in the product, the above method of oxidation can be employed to give the desired isomer.

Scheme 13:

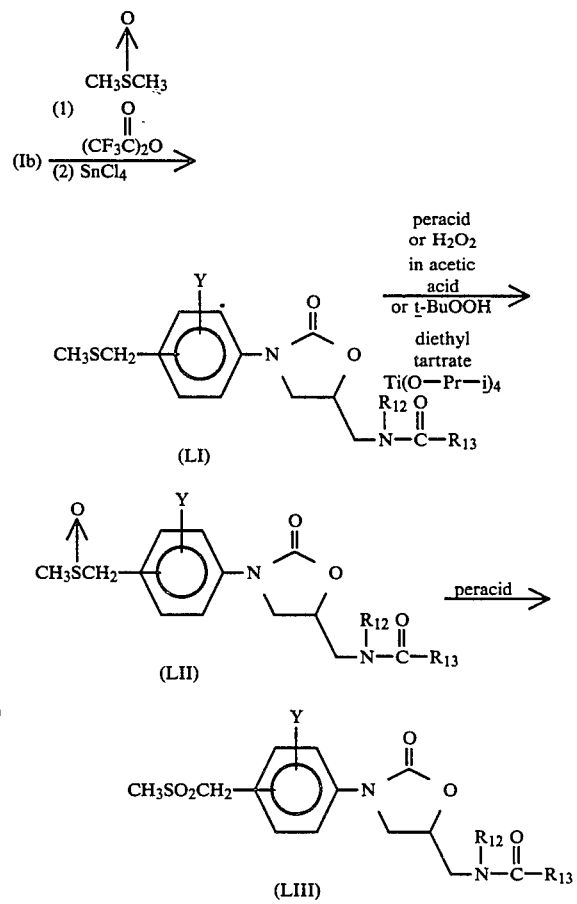

Compounds of Formula (LI) can be prepared as shown in Scheme 13, by the addition of a compound of Formula (Ib) to dimethylsulfoxide and trifluoroacetic anhydride followed by the addition of a Lewis acid such as stannic chloride. The reaction can be carried out at ambient temperatures in a solvent such as methylene chloride, chloroform, 1,2-dichloroethane or other solvents which are inert to the reagents employed.

The sulfides (LI) may then be oxidized to the sulfoxides having the structure (LII) by any of the methods described above in Scheme 11 such as oxidation with hydrogen peroxide in acetic acid, m-chloroperoxybenzoic acid or other peracids to give a mixture of diastereomers. Alternatively, the oxidation can be carried out stereoselectively by the procedure of P. Pitchen, et al., *J. Am. Chem. Soc.*, 106, 8188 (1984) which is described in Scheme 12.

Scheme 14:

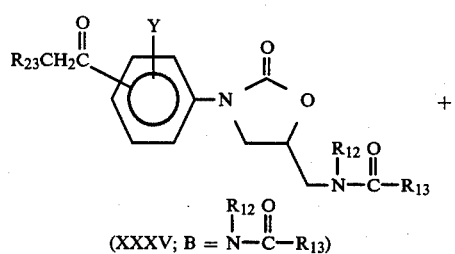

(XXXV; B = N(R$_{12}$)—C(O)—R$_{13}$)

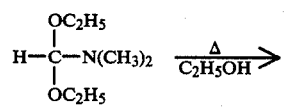

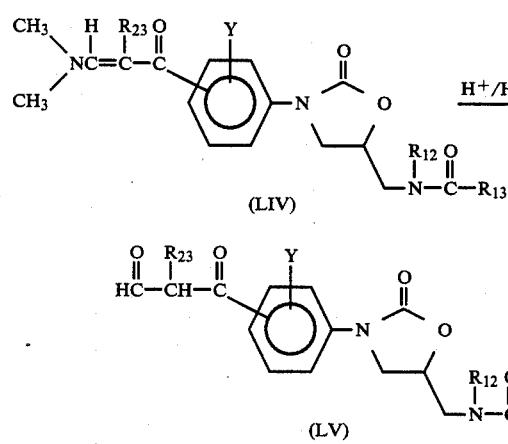

The compounds (LIV) of Scheme 14 where Y is C$_1$–C$_3$ alkyl, and R$_{23}$ is C$_1$–C$_7$ alkyl may be prepared by reaction of a ketone (XXXV) with dimethylformamide diethylacetal (other acetals of DMF can also be used) in a solvent such as ethanol, methanol, tetrahydrofuran or 1,2-dimethoxyethane. The reaction may be carried out at the reflux temperature of the solvent. The reaction time may be 1 hour to several days and is dependent on the reactivity of the ketone and the temperature at which the reaction is run.

Scheme 15:

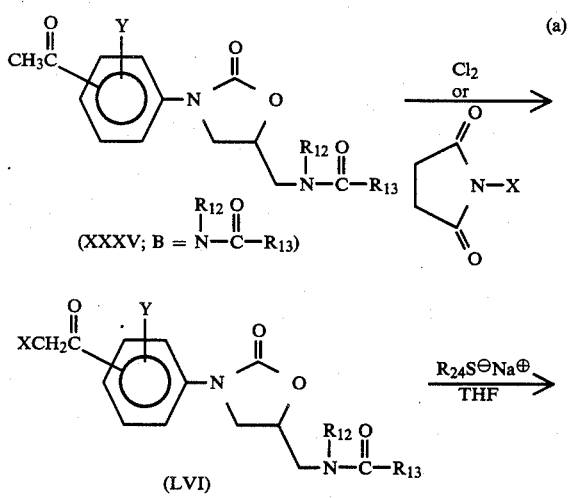

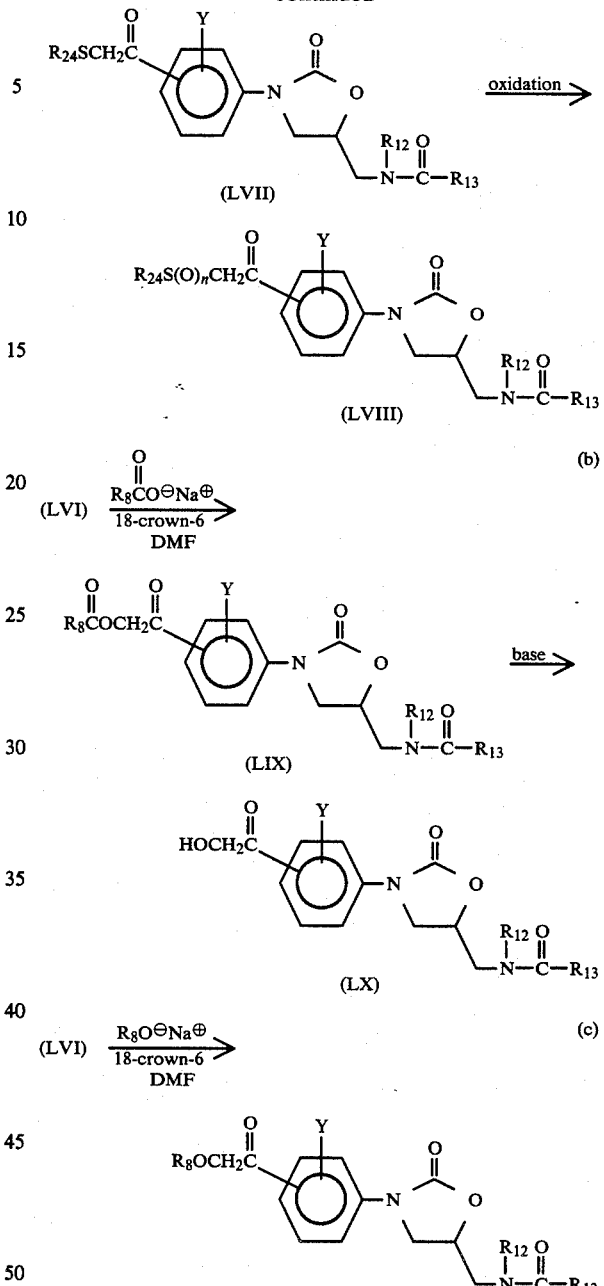

Compounds of formula (I) which may be prepared using the procedures depicted in Scheme 15 are those where A is —COR$_{23}$ wherein R$_{23}$ is an alkyl group substituted with a halogen, and compounds where A is —COR$_{25}$ wherein R$_{25}$ is an alkyl substituted with —S(O)$_n$R$_{24}$, $$-OCR_8,$$

or —OR$_8$. As shown in path (a), the ketones of formula (XXXV) are halogenated by any of the usual methods for halogenation of ketones such as chlorination using gaseous chlorine or bromination with bromine in a solvent such as chloroform, acetic acid, or dichloromethane. Halogenation can also be carried out with sulfuryl chloride, chlorosuccinimide, bromosuccinimide or iodosuccinimide amongst others. The reaction can be catalyzed by light or by a radical initiator such as benzoyl peroxide or azobisisobutyronitrile.

The haloketones (LVI) may then be reacted with a mercaptide salt such as the sodium or potassium salt in a polar solvent such as ethanol, THF, or DMF at a temperature between room temperature and the boiling point of the solvent to give the sulfide (LVII). The sulfides (LVII) may then be oxidized to the corresponding sulfoxides or sulfones (LVIII) by methods previously described.

The esters of structure (LIX) may be prepared by allowing a halide (LVI) to react with the sodium or potassium salt of a carboxylic acid as shown in Scheme 15, path (b), generated using NaH, KH, or KOC$_4$H$_9$-t in an alcohol solvent such as ethanol or methanol or a dipolar aprotic solvent such as dimethylformamide or N-methylpyrrolidinone. The reaction mixture is heated at 30° C. to the reflux point of the solvent, and a catalyst such as 18-crown-6 may be used.

The esters (LIX) may readily be hydrolyzed by reaction with an inorganic base such as sodium hydroxide in an alcohol solvent or by treatment with an organic base such as pyrrolidone, diethylamine, or piperidine to give the hydroxy compounds of the formula (LX).

The alkoxy ketones (LXI) are prepared, as shown in Scheme 15, path (c), by reaction of the halides (LVI) with the appropriate sodium alkoxide in a solvent such as DMF, 1,2-dimethoxyethane, N-methylpyrrolidone, or diglyme ®. A catalyst such as 18-crown-6 may be used.

The alcohols (II) and halides (VII) required as starting materials are readily available by any of a number of standard methods for the preparation of oxazolidones. [M. E. Dyen and D. Swern, *Chem. Rev.*, 67, 197–246 (1967)].

Of these methods, the two which are noteworthy for the variety of compounds prepared are outlined in Scheme 16.

Scheme 16:

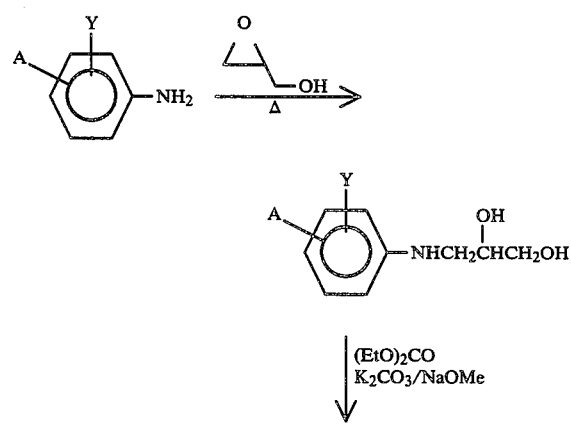

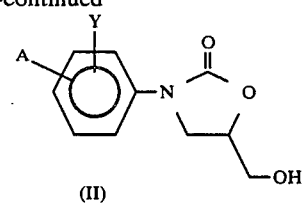

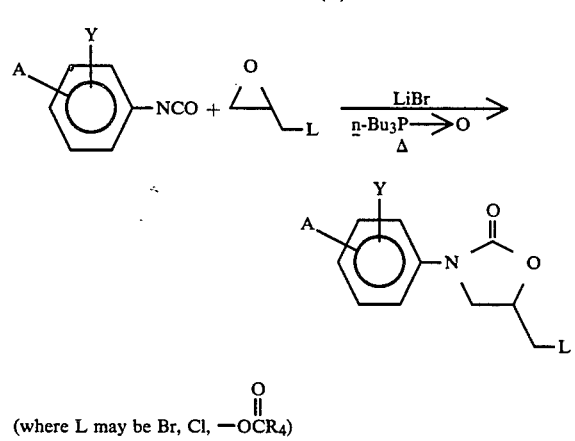

(where L may be Br, Cl, —OCR$_4$)
$$\overset{O}{\underset{\|}{}}$$

Pharmaceutically suitable salts of compounds of formula I can be prepared in a number of ways known in the art. In the definition of R$_1$, cations indicated by Z include alkali and alkaline earth metal ions such as K$^+$, Mg$^{++}$, Ca$^{++}$, Li$^+$, Na$^+$ and tetraalkylammonium. Where B is —NH$_2$ or where R$_{10}$ contains an amino group and A is not S(O)$_n$NXZ, pharmaceutically suitable salts include those resulting from treatment with acetic, hydrochloric, sulfuric, phosphoric, succinic, fumaric, ascorbic, or glutaric acid.

EXAMPLE 1

Preparation of (dl)-5-Azidomethyl-3-[4-(methylsulfonyl)phenyl]-2-oxazolidinone (I; A=4—CH$_3$SO$_2$, B=N$_3$)

Part A

Preparation of (dl)-5-Iodomethyl-3-[4-(methylsulfonyl)phenyl]-2-oxazolidinone

A mixture of 50 g (345 mmole) of (dl)-5-chloromethyl-3-[4-(methylsulfonyl)phenyl]-2-oxazolidinone and 100 g of sodium iodide in 300 ml of 2-butanone was refluxed overnight. This was cooled and poured into 1 liter of ice and water; sodium sulfite was added until all the yellow iodine color was gone; the mixture was filtered and washed with water to provide 61.7 g of iodomethyl compound, m.p. 175.5°–177° C. This material was recrystallized from 370 ml of acetonitrile to give 44.8 g, m.p. 177.5°–179° C.

Part B

A mixture of 7.6 g (20 mmole) of (dl)-5-iodomethyl-3-[4-(methylsulfonyl)phenyl]-2-oxazolidinone and 4 g of sodium azide in 150 ml of (dry) DMAC was heated at 125° C. for three hours. It was then poured into ice and water. The product was extracted with chloroform three times and the extracts dried over sodium sulfate and concentrated to a semi-solid paste. The product was stirred with ether, filtered and dried; yield 4.7 g. This was recrystallized from 14 ml of acetonitrile to give 2.2 g of azidomethyl compound, m.p. 152.5°–153.5° C.

EXAMPLE 2

Preparation of
(l)-5-Azidomethyl-3-[4-(methylsulfonyl)phenyl]-2-oxazolidinone (I; A=4—MeSO$_2$, B=N$_3$)

Part A

Preparation of
(l)-5-Hydroxymethyl-3-[4-(methylsulfonyl)phenyl]-2-oxazolidinone, 4-methylbenzenesulfonate (I; A=4—MeSO$_2$, B=OSO$_2$C$_6$H$_4$Me)

A solution of 5.00 g (l)-5-hydroxymethyl-3-[4-(methylsulfonyl)phenyl]-2-oxazolidinone in 30 ml of pyridine (dry) was stirred at 0°–5° C. and a solution of 3.7 g of p-toluenesulfonyl chloride in 10 ml of pyridine was added slowly. At the end of the addition the mixture was stirred one hour; the mixture crystallized to a semisolid mass. A few drops of water were added to destroy excess sulfonyl chloride. The mixture was poured onto a water-ice mixture, filtered, and washed with water. The product yield was 4.02 g, m.p. 187.1°–188.6° C.

Part B

A mixture of 3.5 g of (l)-5-hydroxymethyl-3-[4-(methylsulfonyl)phenyl]-2-oxazolidinone, 4-methylbenzenesulfonate and 2 g of sodium azide in 20 ml of DMF was heated to 90°–100° C. At the end of one hour, the mixture was cooled and diluted with ice-water, the product crystallized and was filtered and washed well with water; yield 1.25 g; m.p. 146.5°–148.5° C. This product may be crystallized from methanol to give a product melting at 148.9°–149.4° C.

EXAMPLE 3

Preparation of
(l)-4-[5-(Azidomethyl)-2-oxooxazolidin-3-yl]benzenesulfonamide (I; A=4—H$_2$NSO$_2$, B=N$_3$)

Part A

Preparation of
(l)-4-[5-(Hydroxymethyl)-2-oxooxazolidin-3-yl]benzenesulfonamide, 4-methylbenzenesulfonate (I; A=4—H$_2$NSO$_2$, B=OSO$_2$C$_6$H$_4$Me)

A mixture of 13.61 g (50 mmole) of (l)-4-[5-hydroxymethyl)-2-oxooxazolidin-3-yl]benzenesulfonamide in 50 ml of dry pyridine was stirred at −5° to 0° C. as solution of 9.53 g of 4-methylbenzenesulfonyl chloride in 25 ml of pyridine was added dropwise. The reaction was allowed to warm to room temperature and stirred three hours. It was then poured into ice-water, the crystalline product filtered and washed well with water and dried. The yield of product was 19.0 g, m.p. 213.5°–217.5° C.

Part B

A mixture of 18.75 g (44 mmole) of (l)-4-[5-(hydroxymethyl)-2-oxooxazolidin-3-yl]benzenesulfonamide, 4-methylbenzenesulfonate and 3 g of sodium azide in 75 ml of DMF was heated at 50° C. for three hours. The reaction at this stage was only about one-half done, so further sodium azide (2 g) was added and the reaction heated at 50° C. for 6 hours and then at 60° C. for one hour. It was poured into ice and water, filtered, washed well with water and dried; yield 11.24 g, m.p. 139.1°–140.1° C. This was recrystallized from 50 ml of acetonitrile to give 6.1 g of product, m.p. 139.5°–140.1° C.

Using the procedures described in Examples 1–3, the following azides could be prepared.

TABLE 1

| Ex. | A | m.p. (°C.) | isomer |
|---|---|---|---|
| 4 | 4-CH$_3$S | 97.4–98.2° | l |
| 5 | 4-CH$_3$CO | 101–102° | dl |
| 6 | 4-CF$_3$ | | dl |
| 7 | 4-(CH$_3$)$_2$CH | 63–64° | dl |
| 8 | 3-CH$_3$CO | | dl |
| 9 | 4-CH$_3$O | | dl |

EXAMPLE 10

Preparation of
(dl)-5-Aminomethyl-3-[4-(methylsulfonyl)phenyl]-2-oxazolidinone trifluoroacetic Acid Salt
(A=4—CH$_3$SO$_2$, B=NH$_2$·CF$_3$CO$_2$H)

A solution of 1.1 g of (dl)-5-azidomethyl-3-[4-(methylsulfonyl)phenyl]-2-oxazolidinone in 75 ml of trifluoroacetic acid and 0.5 g of 10% palladium-on-charcoal was shaken under hydrogen pressure (approximately 50 psig) for one hour. The mixture was filtered and concentrated to give 0.8 g of product, m.p. 158°–170° C. (dec.).

EXAMPLE 11

Preparation of
(l)-5-Aminomethyl-3-[4-(methylsulfonyl)phenyl]-2-oxazolidinone (I; A=4—MeSO$_2$, B=NH$_2$)

A mixture of 3.48 g (0.0117 mole) of (l)-5-azidomethyl-3-[4-(methylsulfonyl)phenyl]-2-oxazolidinone, 11 ml of 1,3-propanedithiol and 15 ml of triethylamine in 30 ml methanol was warmed to 40°–50° C. as nitrogen evolution occurred at an appreciable rate. After nitrogen evolution ceased, the solution was concentrated under reduced pressure, the residue stirred with ether, and the solid filtered and dried; yield 3.09 g, m.p. 137°–142° C. This was dissolved in about 200 ml of absolute alcohol at reflux (some brown solid did not dissolve) and filtered hot. The product crystallized to yield 2.46 g of product, m.p. 146.6°–147.1° C.

EXAMPLE 12

Preparation of
(l)-4-[5-(Aminomethyl)-2-oxooxazolidin-3-yl]benzenesulfonamide (I; A=4—H$_2$NSO$_2$, B=NH$_2$)

A suspension of 4.5 g (15.1 mmole) of (l)-4-[5-(azidomethyl)-2-oxooxazolidin-3-yl]benzenesulfonamide in 30 ml of methanol and 3 ml of triethylamine was stirred and 3 ml of 1,3-propanedithiol added. Evolution of nitrogen started and the mixture was warmed to reflux. In 15 minutes, all of the solid had dissolved, and heating was continued thirty minutes longer. The methanol was evaporated in a nitrogen stream and ether was added to the residue and a solid crystallized. The filtered solid was dried; yield 5.01 g, m.p. 148°–150° C. This was dissolved in 30 ml water by adding acid, filtered and made strongly basic with concentrated ammonium hydroxide and filtered to give 1.32 g of product, m.p. 151.7°–152.4° C.

Anal. Calcd. for $C_{10}H_{13}N_3O_4S$: C, 44.27; H, 4.83; N, 15.49. Found: C, 44.00, 44.13; H, 5.06, 4.85; N, 15.21, 15.21.

EXAMPLE 13

Preparation of (l)-5-Aminomethyl-3-[4-(methylsulfonyl)phenyl]-2-oxazolidinone (I; A=4—MeSO₂, B=NH₂)

A 2.00 g (6.75 mmole) portion of (l)-5-azidomethyl-3-[4-(methylsulfonyl)phenyl]-2-oxazolidinone in 25 ml of 1,2-dimethoxyethane was stirred under nitrogen as 3.2 ml of trimethylphosphite in 5 ml of 1,2-dimethoxyethane was added. The mixture became warm and a rapid evolution of nitrogen occurred. The mixture was concentrated to leave a brown gum. The gum was stirred with water and solid crystallized. This was dissolved in water by adding dilute acetic acid to pH=4, filtered and the water made basic with concentrated ammonium hydroxide. The yield of product was 0.94 g, m.p. 129°–132.8° C.

EXAMPLE 14

Preparation of (l)-5-Aminomethyl-3-[4-(methylthio)phenyl]-2-oxazolidinone (I; A=4—MeS, B=NH₂)

A mixture of 30.3 g (115 mmole) of (l)-5-azidomethyl-3-[4-(methylthio)phenyl]-2-oxazolidinone, 13.1 ml of 1,3-propanedithiol and 18.2 ml of triethylamine in 150 ml of methanol was stirred at 50° C. for eight hours. It was then concentrated. The residue was stirred with aqueous citric acid, filtered, and the filtrate made basic with concentrated ammonium hydroxide. The product was filtered; yield 16.5 g, m.p. 160°–162° C.

Using the procedures of Examples 10–14, the following amines could be prepared.

TABLE 2

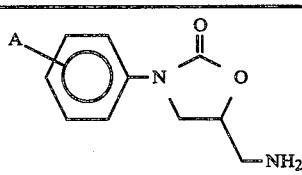

| Ex. | A | m.p. (°C.) | isomer |
|---|---|---|---|
| 15 | 4-CH₃CO | 115–116° | dl |
| 16 | 3-CH₃CO | | dl |
| 17 | 4-(CH₃)₂CH | 104.1–105.1 | dl acetate salt |
| 18 | 4-CF₃ | | dl |
| 19 | 4-CH₃O | | dl |
| 20 | 4-NC | | dl |

EXAMPLE 21

Preparation of (l)-N-[3-[4-(Methylsulfonyl)phenyl]-2-oxooxazolidin-5-ylmethyl]formamide (I; A=4—MeSO₂, B=NHCHO)

A solution of 1.00 g (3.70 mmole) of (l)-5-aminomethyl-3-[4-(methylsulfonyl)phenyl]-2-oxazolidinone, in 10 ml of 2-propanol containing 2.5 ml of ethyl formate was heated at reflux for twenty-four hours. The mixture was cooled and diluted with ether to give 0.96 g of material which was recrystallized from 9.5 ml of acetonitrile to give 0.65 g of product, m.p. 190°–191.6° C.

EXAMPLE 22

Preparation of (l)-2,2-Dichloro-N-[3-[4-(methylsulfonyl)phenyl]-2-oxooxazolidin-5-ylmethyl]acetamide (I; A=–4—MeSO₂, B=NHCOCHCl₂)

A mixture of 2.00 g (7.4 mmole) of (l)-5-aminomethyl-3-[4-(methylsulfonyl)phenyl]-2-oxazolidinone, 2 ml methyl dichloroacetate and 10 ml of ethanol was refluxed under nitrogen for five hours. The mixture was concentrated under reduced pressure then stirred with ether and filtered; yield 2.72 g, m.p. 174.0°–181.9°. This was stirred with water and made acid with acetic acid, filtered and washed with water; yield 2.60 g, m.p. 194.5°–196.1° C. This was dissolved in boiling 70% ethanol:water made acid with acetic acid, cooled and filtered; yield of product 1.65 g, m.p. 203.3°–204.3° C.

Anal. Calcd. for $C_{13}H_{14}Cl_2N_2O_5S$: C, 40.95; H, 3.70; N, 7.35. Found: C, 40.82; H, 3.70; N, 7.10, 7.15.

EXAMPLE 23

Preparation of (l)-N-[3-[4-(Methylsulfonyl)phenyl]-2-oxooxazolidin-5-ylmethyl]acetamide (I; A=4—MeSO₂, B=NHCOCH₃)

A 2.00 g (7.4 mmole) portion of (l)-5-aminomethyl-3-[4-(methylsulfonyl)phenyl]-2-oxazolidinone in 10 ml of pyridine was cooled in a ice-bath as 0.72 ml of acetic anhydride was added. The mixture was stirred for 10 to 20 minutes then diluted with ice-water. The product was filtered and washed with water; m.p. 191.9°–192.9° C. After recrystallization from acetonitrile, there was obtained 1.01 g of product, m.p. 192.7°–193.2° C.

Anal. Calcd. for $C_{13}H_{16}N_2O_5S$: C, 49.99; H, 5.16; N, 8.97. Found: C, 49.48; H, 5.17; N, 8.93, 8.88.

EXAMPLE 24

Preparation of (l)-N-[3-[4-(Aminosulfonyl)phenyl]-2-oxooxazolidin-5-ylmethyl]formamide (I; A=4—H₂NSO₂, B=NHCHO)

A mixture of 2.00 g (7.37 mmole) of (l)-[5-(aminomethyl)-2-oxooxazolidin-3-yl]benzenesulfonamide, 2 ml of n-butyl formate and 0.5 g of 1,4-diazobicyclo[2.2.2]octane (DABCO) in 30 ml of DMF was heated at 90°–100° C. for about 24 hours. It was concentrated under reduced pressure and the residue stirred with 10 ml of water. The product crystallized, 2.60 g, m.p. 184.5°–186.5° C. This was recrystallized from 70% ethanol in water followed by recrystallization from acetonitrile. The product melted at 191°–192° C. (dec.).

EXAMPLE 25

Preparation of
(l)-N-[3-[4-(Methylsulfonyl)phenyl]-2-oxooxazolidin-5-ylmethyl]methanesulfonamide (I; A=4—MeSO2, B=NHSO2Me)

A solution of 1.00 g (3.70 mmole) of (l)-5-aminomethyl-3-[4-(methylsulfonyl)phenyl]-2-oxazolidinone in 50 ml of dry pyridine was stirred in an ice-bath as methanesulfonyl chloride (2.3 ml) was slowly added. After the addition was complete, 3 drops of water were added and the mixture concentrated. The residue was stirred with water and a few drops of concentrated HCl added until the solution was acid. The precipitate was filtered, washed with water and dried. The yield was 0.77 g, m.p. 216.7°–220.7° C. This was recrystallized from acetonitrile, water (4:1) to give 0.51 g of product, m.p. 219.7°–220.7° C.

EXAMPLE 26

Preparation of
(l)-N-[3-[4-(Methylsulfonyl)phenyl]-2-oxooxazolidin-5-ylmethyl]carbamic acid, methyl ester (I; A=4—MeSO2, B=NHCO2Me)

A mixture of 5.41 g (0.02 mole) of (l)-5-aminomethyl-3-[4-(methylsulfonyl)phenyl]-2-oxazolidinone in 50 ml of tetrahydrofuran was stirred in an ice-bath as a solution of 2 ml of methyl chloroformate in 10 ml of tetrahydrofuran was added along with 2N NaOH to keep the pH between 10–11. The mixture was stirred 45 minutes after all of the methyl chloroformate had been added. The organic solvents were removed under reduced pressure and the residue diluted with water and the pH brought to 7, the solid filtered and washed with water; yield 6.5 g, m.p. 210°–211° C. This was recrystallized from acetonitrile to give 3.5 g of product, m.p. 214°–215° C.

A further recrystallized sample melted at 316.9°–217.6° C.

Anal. Calcd. for $C_{13}H_{16}O_6N_2S$: C, 47.55; H, 4.91; N, 8.53. Found: C, 47.55, 47.46; H, 4.88, 4.81; N, 8.73, 8.62.

$[\alpha]_D^{25} = -47.7 \pm 0.4°$ (c=1 in acetonitrile)

In the same manner, by reacting the appropriate acyl halide, isocyanate, chloroformate ester, or ester with an amine of the structure:

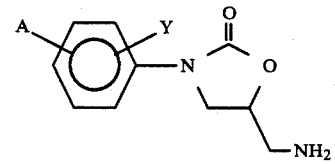

the following compounds could be prepared:

TABLE 3

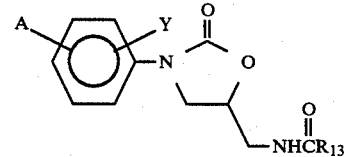

| Ex. | A, Y | R13 | m.p. °C. | Isomer |
|---|---|---|---|---|
| 27 | 4-CH3SO2, H | —CH2CH3 | 195.8–197.1 | l |
| 28 | 4-CH3SO2, H | —CF3 | 239.6–240.3 | l |
| 29 | 4-CH3SO2, H | CH2CH2CH3 | 208.1–208.7 | l |
| 30 | 4-CH3SO2, H | C(CH3)3 | 172.3–172.9 | l |
| 31 | 4-CH3S, H | CH3 | 166.7–167.1 | l |
| 32 | 4-CH3S, H | OCH3 | 140.5–141.5 | l |
| 33 | 4-CH3S, H | OCH2CH3 | 140–142 | l |
| 34 | 4-CH3SO2, H | C6H5 | 221.6–221.9 | l |
| 35 | 4-CH3SO2, H | NHCH3 | 197.8–198.7 | l |
| 36 | 4-CH3C=NNHCOCH3, H | CH3 | 205–207 | dl |
| 37 | 3-CH3CO, H | CH3 | 145–146 | dl |
| 38 | 4-(CH3)2CH, H | CH3 | 142.7–143.3 | dl |
| 39 | 4-(CH3)2CH, H | OCH3 | 107.8–108.3 | dl |
| 40 | 4-CH3S, H | CH=CH2 | 172–174 | dl |
| 41 | 4-CF3, H | CH3 | 179.0–179.8 | dl |
| 42 | 4-CF3, H | OCH3 | 153.3–153.6 | dl |
| 43 | 4-CH3O, H | OCH3 | | |
| 44 | 4-CH3O, H | CH3 | 149.0–149.6 | dl |
| 45 | 4-H2NSO2, H | OCH3 | 229.9–230.5 | l |
| 46 | 4-CH3NHSO2, H | CH3 | 181.5–182 | l |
| 47 | 4-(CH3)2NSO2, H | CHCl2 | | |
| 48 | 4-CH2=CH—CH2NHSO2, H | CH2OCH3 | | |
| 49 | 4-[cyclopropyl]-NHSO2, H | CHBr2 | | |
| 50 | 4-CH3ON(CH3)SO2, H | OC2H5 | | |
| 51 | 4-(CH3)2CH, H | CH3 | 118.9–119.4 | l |
| 52 | 4-(CH3)2CH, H | OCH3 | 129.0–129.3 | l |
| 53 | 4-CH3NHN(CH3)SO2, H | CHCl2 | | |
| 54 | 4-n-C4H9NHSO2, H | CH=CH2 | | |
| 55 | 4-cyclooctyl NHSO2, H | CH2Br | | |
| 56 | 4-H2NNHSO2, H | CH(OCH3)2 | | |
| 57 | 4-CH3SO2, H | CH2OCH3 | 164.6–165.6 | l |
| 58 | 4-CF3S, H | O—C4H9—t | | |

TABLE 3-continued

| Ex. | A, Y | $R_{13}$ | m.p. °C. | Isomer |
|---|---|---|---|---|
| 59 | 4-NC, H | $CH_3$ | 153-154 | dl |
| 60 | 4-$CF_2$HSO, H | $CH=CH_2$ | | |
| 61 | 4-$CH_2=CH-CH_2$S, H | $CH_3$ | | |
| 62 | 3,4-$OCH_2O-$ | $CH_3$ | 156-157 | dl |
| 63 | 4-$Cl_2$CHSO, H | $CH(OCH_3)_2$ | | |
| 64 | 4-$CH_2$FS, H | $SCH_3$ | | |
| 65 | 4-$CCl_3$SO, H | $CH_2-S(O)_2CH_3$ | | |
| 66 | 4-$CH_2BrSO_2$, H | $S-C_4H_9-\underline{n}$ | | |
| 67 | 4-$CH_3SO_2$, H | $CH_2Cl$ | 195.1-195.9 | l |
| 68 | 4-$CH_3$S, H | $NHCOCOCH_3$ | 142.9-143.5 | l |
| 69 | 4-$CH_3SO_2$, H | $CH=CH_2$ | 180-183 | dl |
| 70 | 4-$CH_3SO_2$, H | $OCH_2CH_2CH_3$ | 170-173 | dl |
| 71 | 4-$CH_3$S, H |  | 197-199 | dl |
| 72 | 4-$CH_3SO_2$, H | 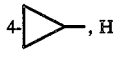 | 210-211 | dl |
| 73 | 4-$CH_3$S, H | $CH(OCH_3)_2$ | 89-90 | dl |
| 74 | 4-$CH_3SO_2$, H | $CH(OCH_3)_2$ | 175-178 | dl |
| 75 | 4-$CH_3$S, H | $CH(OC_2H_5)_2$ | 68-69 | dl |
| 76 | 4-$CH_3SO_2$, H | $CH(OC_2H_5)_2$ | 142-144 | dl |
| 77 | 4-$CH_3SO_2$, H | $NH_2$ | 146-149 | dl |
| 78 | 4-$CH_3SO_2$, H | $CH(NH_2)C_6H_5.HCl$ | 250 | dl |
| 79 | 4-$CH_3$, H | $CH_3$ | 133.8 | dl |
| 80 | 4-$CH_3(CH_2)_3$, H | $OCH_3$ | 104 | dl |
| 81 | 4-$CH_3(CH_2)_3$, H | $CH_3$ | 147.5 | dl |
| 82 | 4-$CH_3CH_2$, H | $CH_3$ | 148 | dl |
| 83 | 4-$CH_3CH_2$, H | $OCH_3$ | 108 | dl |
| 84 | 4-Cl, H | $OCH_3$ | 123-124 | dl |
| 85 | 4-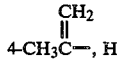, H | $OCH_3$ | | |
| 86 | 4-Br, H | $CH_3$ | 179.8-182.1 | l |
| 87 | 4-Cl, H | $CH_3$ | 155-156 | dl |
| 88 | 4-F, H | $CH_3$ | 135-136 | dl |
| 89 | 4-$CH_3$S, H | H | 142-145.5 | l |
| 90 | 4-$CH_3$SO, H | H | 102.1-112.2 | l |
| 91 | 4-$CH_3$SO, H | $CH=CH_2$ | | dl |
| 92 | 4-$CH_3$S, H | $CH_2CH_2Cl$ | 158-160 | dl |
| 93 | 4-$CH_3$SO, H | $CH_2CH_2Cl$ | 138-140 | dl |
| 94 | 4-$CH_3SO_2$, H | $CH_2CH_2Cl$ | 173-178 | dl |
| 95 | 4-$CH_3$CO, H | $CH_2CH_2Cl$ | 170-172 | dl |
| 96 | 4-$CH_3$CO, H | $CH=CH_2$ | 188-190 | dl |
| 97 | 4-$CH_3\overset{\overset{CH_2}{\|}}{C}-$, H | $CH_3$ | 153-155 | l |
| 98 | 4-$CH_3\overset{\overset{CH_2}{\|}}{C}-$, H | $OCH_3$ | | |
| 99 | 4-$CH_3COCH_2$, H | $CH_3$ | 139.5-142 | dl |
| 100 | 4-$CH_3\overset{\overset{OH}{\|}}{C}HCH_2$, H | $CH_3$ | 141.5-144.0 | dl |
| 101 | 4-$CH_2=CH-$, H | $CH_3$ | 169-171 | l |
| 102 | 4-$HOCH_2\overset{\overset{OH}{\|}}{\underset{\underset{CH_3}{\|}}{C}}$, H | $CH_3$ | 108-114 | dl |
| 103 | 4-$HOCH_2C\equiv C$, H | $CH_3$ | 141-142 | l |

TABLE 3-continued

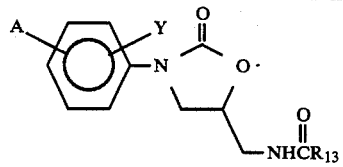

| Ex. | A, Y | $R_{13}$ | m.p. °C. | Isomer |
|---|---|---|---|---|
| 104 | 4-HOCH$_2$—CH(OH), H | CH$_3$ | 99–101 | l |
| 105 | 4-CH$_3$C(CH$_3$)$_2$, H | CH$_3$ | 145.5–146.5 | l |
| 106 | 4-HOCH$_2$, H | CH$_3$ | 122–125 | l |
| 107 | 4-HO(CH$_2$)$_3$, H | CH$_3$ | 109–111 | l |
| 108 | 4-C$_2$F$_5$, H | CH$_3$ | 148–150 | l |

The following sulfonamides may also be made:

TABLE 4

$$R_1S(O)_n-\text{(phenyl)}-N-\text{oxazolidinone}-CH_2-N(R_{12})-S(O)_uR_{14}$$

| Ex. | n | $R_1$ | $R_{12}$ | u | $R_{14}$ | m.p. (°C.) |
|---|---|---|---|---|---|---|
| 109 | 1 | —CF$_3$ | H | 1 | —CH$_3$ | |
| 110 | 0 | —CH$_3$ | H | 2 | —CF$_3$ | |
| 111 | 2 | —CH$_3$ | H | 2 | —C$_3$H$_7$—n | |

EXAMPLE 112

Preparation of
(l)-2,2-Dichloro-N-[3-[4-(aminosulfonyl)phenyl]-2-oxooxazolidin-5-ylmethyl]acetamide (I; A=4—H$_2$NSO$_2$, B=NHCOCHCl$_2$)

Part A

Preparation of
(l)-5-hydroxymethyl-3-phenyl-2-oxazolidinone, 4-methylbenzenesulfonate, (I; A=H, B=OSO$_2$C$_6$H$_4$Me)

A mixture of 51.5 g of (l)-5-hydroxymethyl-3-phenyl-2-oxazolidinone in 250 ml of dry pyridine was stirred under N$_2$ in an ice-bath as a solution of 53 g of p-toluenesulfonyl chloride in 50 ml of pyridine was added. After the addition, cooling was ceased, the mixture allowed to stand for one hour, and then a few drops of water were added (the temperature rose to 39° C. as the water reacted with the excess p-toluenesulfonyl chloride). The reaction mixture was poured into ice water; the white solid was filtered, washed well with water, and dried. The yield of product was 70.0 g, m.p. 146.3°–147.8° C. This product was used without further purification.

Part B

Preparation of
(l)-5-Azidomethyl-3-phenyl-2-oxazolidinone (I; A=H, B=N$_3$)

A mixture of 5.00 g (14.4 mmole) of (l)-5-hydroxymethyl-3-phenyl-2-oxazolidinone, 4-methylbenzenesulfonate, 2.1 g sodium azide and 1 g 18-crown-6 in 35 ml of DMF was heated at 100° C. for three hours. The mixture was poured into ice-water and filtered. The dried yield was 2.47 g, m.p. 71.5°–72.5° C. This was recrystallized from diethyl ether to give 1.44 g of product, m.p. 72.5°–73° C.

Part C

Preparation of
(l)-5-Aminomethyl-3-phenyl-2-oxazolidinone (I; A=H, B=NH$_2$)

A mixture of 37.0 (170 mmole) of (l)-5-azidomethyl-3-phenyl-2-oxazolidinone, 26 ml of triethylamine, 19.5 ml of 1,3-propanedithiol in 150 ml of methanol was warmed to 50° C. Nitrogen was evolved (at the end of 2 hours, 3.9 liters had been measured). The solvent was removed and the residue crystallized on stirring with ether (crude yield, 28.3 g). This material was used without further purification.

Part D

Preparation of
(l)-2,2-Dichloro-N-(3-phenyl-2-oxazolidin-5-ylmethyl)acetamide (I; A=H, B=NHCOCHCl$_2$)

A solution of 12.5 g (64.5 mmole) of (l)-5-aminomethyl-3-phenyl-2-oxazolidinone in 45 ml of methyl dichloroacetate and 45 ml of 1,2-dimethoxyethane containing 1 g of 4-dimethylaminopyridine was refluxed four hours. It was concentrated, the residue stirred with ethyl acetate and the product crystallized and was filtered and dried. The yield was 9.18 g, m.p. 142.3°–144.8° C. This was recrystallized from ethanol, filtered hot, and cooled to give 7.46 g, m.p. 150.3°–151.3° C.

Part E

A 15 ml portion of chlorosulfonic acid was cooled and stirred under nitrogen as 8.77 g (28.9 mmole) of (l)-2,2-dichloro-N-(3-phenyl-2-oxooxazolidin-5-ylmethyl)acetamide was added. Hydrogen chloride bubbled from the acid and the solid dissolved. After one hour the acid solution was poured into ice with good stirring, filtered and dried on the filter under nitrogen for one hour. This solid was added to a mixture of 25 ml of concentrated ammonium hydroxide in 50 ml of tetrahydrofuran. After stirring for four minutes, the resulting mixture was concentrated under reduced pressure; water was added and the product filtered, washed with water, and dried; yield 9.13 g, m.p. 208°–209° C. This was recrystallized from 70% ethanol water to give 6.65 g, m.p. 214.8°–215.4° C. It was then recrystallized from acetonitrile to yield 6.54 g, m.p. 216.5°–217.5° C.

EXAMPLE 113

Preparation of
(l)-N-[3-[4-(Aminosulfonyl)phenyl]-2-oxooxazolidin-5-ylmethyl]acetamide (I; A=4—H$_2$NSO$_2$, B=NHCOCH$_3$)

Part A

Preparation of
(l)-N-(3-Phenyl-2-oxazolidin-5-ylmethyl)acetamide (I; A=H, B=NHCOCH$_3$)

A solution of 12.5 g (65.0 mmole) of (l)-5-aminomethyl-3-phenyl-2-oxazolidinone in 50 ml of dry pyridine was stirred as 7 ml of acetic anhydride was added. The mixture was allowed to stand overnight, then concentrated. The residue was stirred with water and the solid filtered and dried; yield 10.2 g, m.p. 122.4°–124.5° C. This was recrystallized from ethanol to give 5.02 g, m.p. 126:8°–127.3° C. A second crop was obtained and recrystallized from ethanol to give 3.08 g, m.p. 127.3°–127.8° C.

Part B

The chlorosulfonation and amidation procedures of Example 112 were used, starting with 7.91 g (33.8 mmoles) of (l)-N-(3-phenyl-2-oxooxazolidin-5-ylmethyl)acetamide. The yield of product was 6.85 g, m.p. 236.4°–236.6° C.

EXAMPLE 114

Preparation of
(l)-N-[3-(4-Azidosulfonylphenyl)-2-oxooxazolidin-5-ylmethyl]acetamide (I; A=4—N$_3$SO$_2$—, B=NH—COCH$_3$)

A 5.0 g (21.3 mmole) portion of (l)-N-(3-phenyl-2-oxooxazolidin-5-ylmethyl)acetamide was added to 25 ml of chlorosulfonic acid, stirred for 2 hours, poured onto ice, filtered, and washed well. After the product was sucked dry on a filter, it was added to a solution made by dissolving 2.0 g sodium azide in 5 ml of water and diluting this with 50 ml of acetone. The mixture was stirred for 2 hours; the acetone was evaporated under reduced pressure. The residue was diluted with water and filtered to provide 5.81 g of product, m.p. 102°–104° C. (dec.). This was recrystallized from ethanol to give 5.0 g of material, m.p. 122.5°–123.4° C. (dec.).

Using the chlorosulfonation described in Examples 112 through 114, the following compounds could be prepared.

TABLE 5

| Ex. | R$_1$ | R$_{13}$ | m.p. | isomer |
|---|---|---|---|---|
| 115 | H$_2$N | OCH$_3$ | 229.9–230.5 | l |
| 116 | CH$_3$ CH$_3$ON | OCH$_3$ | 128.1–129.1 | l |
| 117 | N$_3$ | OCH$_3$ | 107.0–107.5 | l |
| 118 | CH$_3$ONH | CH$_2$CH$_3$ | | |
| 119 | H$_2$NNH | OCH$_2$CH$_3$ | | |

EXAMPLE 120

Preparation of
(l)-N-[3-[4-(Methylsulfinyl)phenyl]-2-oxooxazolidin-5-ylmethyl]acetamide (I; A=4—MeSO, B=NHCOCH$_3$)

A 5.61 g (20 mmole) portion of (l)-N-[3-[4-(methylthio)phenyl]-2-oxooxazolidin-5-ylmethyl]acetamide in 200 ml of methanol was stirred at 0° C. as a solution of 12.3 g of Oxone ® (2KHSO$_5$·KHSO$_4$·K$_2$SO$_4$) in 50 ml of water was added slowly. At the end of the addition the sulfide had all been consumed as determined by thin layer chromatography, and the product was a mixture of sulfoxide and sulfone. The solution was heated with 12 ml of methyl sulfide to reduce the excess Oxone ®, concentrated under reduced pressure to give 2.0 g of product, m.p. 188.6°–189.9° C. This was recrystallized from 70% ethanol-water to give 1.5 g of the sulfoxide, m.p. 193.7°–197° C.

EXAMPLE 121

Preparation of
(l)-N-[3-[4-(Methylsulfinyl)phenyl]-2-oxooxazolidin-5-ylmethyl]carbamic acid, methyl ester (I; A=4—CH$_3$SO, B=NHCO$_2$CH$_3$)

Using the procedure of Example 120, the title compound could be prepared starting from the compound of Example 32; m.p. 150.5°–159.5° C.

EXAMPLE 122

Preparation of
(dl)-N-Hexyl-N-[3-[4-(methylsulfonyl)phenyl]-2-oxooxazolidin-5-ylmethyl]acetamide (I; A=4—MeSO$_2$, B=N(C$_6$H$_{13}$)COCH$_3$)

Part A

Preparation of
(dl)-5-(Hexylaminomethyl)-3-[4-(methylsulfonyl)phenyl]-2-oxazolidinone (I; A=MeSO$_2$, B=NHC$_6$H$_{13}$)

(dl)-5-Bromomethyl-3-[4-(methylsulfonyl)phenyl]-2-oxazolidinone (21.92 g) was added to a mixture of 50 ml hexylamine and 25 ml N,N-dimethylformamide. This mixture was heated to 80° C. under nitrogen with vigorous stirring overnight, and allowed to cool to room temperature. The mixture was poured into water with vigorous stirring and the product was collected and washed with ethanol and diethyl ether. The dried weight of crude product was 6.25 g which was recrystallized from acetonitrile to give 4.7 g of (dl)-5-(hex-ylaminomethyl)-3-[4-(methylsulfonyl)phenyl]-2-oxazolidinone, m.p. 132°–133° C.

Part B

To a solution of 3.4 g of (dl)-5-(hexylaminomethyl)-3-[4-(methylsulfonyl)phenyl]-2-oxazolidinone in 30 ml of pyridine was added 1.8 ml of acetic anhydride. The mixture was stirred at room temperature overnight. The mixture was evaporated and the residue was triturated with dilute aqueous HCl. The product was collected and washed thoroughly with water to give, after drying, 3.4 g of crude product. This was recrystallized from aqueous ethanol to give 2.6 g of (dl)-N-hexyl-N-[3-[4-(methylsulfonyl)phenyl]-2-oxooxazolidin-5-ylmethyl]acetamide, m.p. 123°–124° C.

EXAMPLE 123

Preparation of (dl)-N-hexyl-N-[3-[4-(methylsulfonyl)phenyl]-2-oxooxazolidin-5-ylmethyl]carbamic acid, methyl ester (I; A=4—MeSO$_2$, B=N(C$_6$H$_{13}$)CO$_2$CH$_3$)

In the same manner as in Example 122, Part B, the product of Example 122, Part A is reacted with methyl chloroformate to provide (dl)-N-hexyl-N-[3-[4-(methylsulfonyl)phenyl]-2-oxooxazolidin-5-ylmethyl]carbamic acid, methyl ester, m.p. 126°–127° C.

EXAMPLE 124

(dl)-N-Cyclohexyl-N-[[3-[4-(methylsulfonyl)phenyl]-2-oxooxazolidin-5-yl]methylacetamide (I; A=4—MeSO$_2$, B=N(C$_6$H$_{11}$)COCH$_3$)

Part A (dl)-5-(Cyclohexylaminomethyl)-3-[4-(methylsulfonyl)phenyl]-2-oxazolidinone (I; A=4—MeSO$_2$, B=NHC$_6$H$_{11}$)

(dl)-5-Hydroxymethyl-3-[4-(methylsulfonyl)phenyl]-2-oxazolidinone, 4-methylbenzenesulfonate (15 g) was added to a mixture of 60 ml cyclohexylamine and 30 ml N,N-dimethylformamide and heated gently to 70° C. under nitrogen with vigorous stirring overnight. The mixture was allowed to cool to room temperature and was then poured onto water. The product precipitated and was collected and dried; yield 7.48 g.

A portion of the solid obtained above (3.75 g) was purified by dissolving in dilute aqueous HCl, washing with ethyl acetate, and precipitated by addition of concentrated ammonium hydroxide. The pure product was washed with water and dried to give 1.1 g of (dl)-5-(cyclohexylaminomethyl)-3-[4-(methylsulfonyl)phenyl]-2-oxazolidinone, m.p. 154°–155° C.

Part B

To a solution of 2.56 g of (dl)-5-(cyclohexylaminomethyl)-3-[4-(methylsulfonyl)phenyl]-2-oxazolidinone in 25 ml pyridine was added 2 ml acetic anhydride and the mixture was stirred at room temperature under nitrogen overnight. The mixture was evaporated and the residue was triturated with dilute aqueous HCl. The gummy residue was dissolved in ethyl acetate and washed with saturated aqueous NaHCO$_3$ and brine, and dried over sodium sulfate. Evaporation gave a solid which was triturated with ethyl acetate-diethyl ether and collected to give 2.28 g of (dl)-N-cyclohexyl-N-[3-[4-(methylsulfonyl)phenyl]-2-oxooxazolidin-5-ylmethyl]acetamide, m.p. 149°–151° C.

Using the procedures described above, the following compounds could be prepared.

TABLE 6

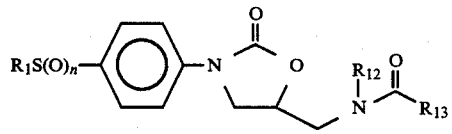

| Ex. | n | R$_1$ | R$_{12}$ | R$_{13}$ | m.p. (°C.) | Isomer |
|---|---|---|---|---|---|---|
| 125 | 1 | —CF$_3$ | n-C$_9$H$_{19}$— | H | | l |
| 126 | 2 | n-C$_4$H$_9$ | —CH$_3$ | H | | l |
| 127 | 1 | —C$_2$H$_5$ | —CH$_3$ | —OCH$_3$ | | l |
| 128 | 2 | —CH$_3$ | —CH$_3$ | —OCH$_3$ | 152–155° | dl |

EXAMPLE 129

Preparation of (l)-N-[3-(4-Acetylphenyl)-2-oxo-5-oxazolidinylmethyl)acetamide (I;

B=NHCOCH$_3$)

A 25 ml portion of methanesulfonic acid was stirred in a dry nitrogen atmosphere as 3.5 g (15 mmole) of (l)-N-(3-phenyl-2-oxazolidin-5-ylmethyl)acetamide was added. To this was added 3 ml of acetic anhydride. The mixture was stirred for 2.5 hours, poured onto ice and the product was extracted with dichloromethane. The combined dichloromethane extracts were dried over sodium sulfate. The evaporation of the extract yielded a crude yellow product (4.6 g) which was recrystallized from acetonitrile to give 2.33 g of the title compound, m.p. 190.5°–191.0° C.

EXAMPLE 130

Preparation of (l)-N-[3-[4-(1-Hydroxyethyl)phenyl]-2-oxo-5-oxazolidinylmethyl]acetamide (I;

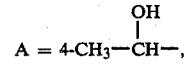

B=—NHCOCH$_3$)

A 2.00 g (7.2 mmole) portion of (l)-N-[3-(4-acetylphenyl)-2-oxooxazolidin-5-ylmethyl]acetamide in 50 ml of ethanol was stirred as a solution of 1.00 g of sodium borohydride in 5 ml of water was added. The solid went into solution and at the end of 15 minutes thin layer chromatography showed the reaction had gone to completion. The solvent was removed by concentration under vacuum, the residue diluted with water and made acidic with dilute HCl and the product extracted into dichloromethane. The extracts were dried over sodium sulfate and concentrated. The residue was recrystallized from acetonitrile to give 0.66 g, m.p. 128.8°–129.8° C.

EXAMPLE 131

Preparation of
(l)-N-[3-[4-(1-Hydrazonoethyl)phenyl]-2-oxo-5-oxazolidinylmethyl]acetamide (I;

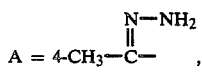

B=—NHCOCH₃)

A mixture of 1.7 g (6.2 mmole) of (l)-N-[3-(4-acetylphenyl)-2-oxooxazolidin-5-ylmethyl]acetamide and 0.25 ml of 98% hydrazine in 25 ml of absolute ethanol was refluxed 1.5 hours and the reaction was about half way complete. An additional 0.125 ml of 98% hydrazine was added and the reaction was refluxed an additional 2 hours. The mixture was concentrated to dryness, the residue diluted with ethanol and the product crystallized. The yield was 1.2 g, m.p. >235° C. The structure of this product was confirmed by NMR.

EXAMPLE 132

Preparation of
(l)-N-[3-[4-[1-(Acetylhydrazono)ethyl]phenyl]-2-oxo-5-oxazolidinylmethyl]acetamide

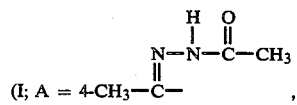

B=—NHCOCH₃)

A solution of 1.00 g (3.62 mmole) of (l)-N-[3-[4-(1-hydrazonoethyl)phenyl]-2-oxo-5-oxazolidinylmethyl]acetamide in 10 ml of tetrahydrofuran and 10 ml of triethylamine was stirred as 0.5 ml of acetic anhydride was added. To this solution 0.1 g of 4-dimethylaminopyridine is added followed by 1 ml of acetic anhydride. After stirring 1 hour the mixture was concentrated and diluted with water and the solid was filtered; yield 1.01 g, m.p. 216.2°–216.8° C.

EXAMPLE 133

Preparation of
(l)-N-[3-(4-Ethylphenyl)-2-oxo-5-oxazolidinylmethyl]acetamide (I; A=4—CH₃CH₂—, B=—NHCOCH₃)

A solution of 500 mg of (l)-N-[3-(4-acetylphenyl)-2-oxooxazolidin-5-ylmethyl]acetamide in 75 ml of ethanol containing 0.5 g of 10% palladium-on-carbon was shaken in a Parr shaker under 43 lbs. of hydrogen overnight. The solution was filtered and concentrated to yield 410 mg of the product. This was recrystallized from ethanol to give 370 mg of the title compound, m.p. 131°–135.2° C.

Using the procedures of Examples 129–133, the following compounds could be prepared.

TABLE 7

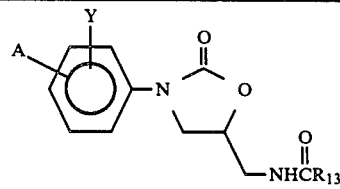

| Ex. | A, Y | R₁₃ | m.p. °C. | Isomer |
|---|---|---|---|---|
| 134 | 4-CH₃CH₂CO, H | CH₃ | 180–181 | l |
| 135 | 4-ClCH₂CO, H | CH₃ | 175.8–178.8 | l |
| 136 | 4-CH₃CH₂CH₂, H | CH₃ | 111.5–112.5 | l |
| 137 | 4-CH₃CH₂CH(OH), H | OCH₃ | | |
| 138 | 4-CH₃(CH₂)₂CO, H | CH₃ | 201.7–202.5 | l |
| 139 | 4-CH₃CH₂C=NNH₂, H | CH₃ | | |
| 140 | 4-Br₃CCO, H | CH₃ | 145–146 | l |
| 141 | 4-C₆H₁₁CO, H | CH₃ | 149–151 | l |
| 142 | 4-CH₃CO, 3-CH₃ | CH₃ | 134–135 | l |
| 143 | 4-CH₃CO, 3-C₂H₅ | CH₃ | 90–91 | l |
| 144 | 4-CH₃CO, 3-CH₃ | OCH₃ | | |

EXAMPLE 145

Preparation of
(l)-N-[3-(4-Iodophenyl)-2-oxo-5-oxazolidinylmethyl]acetamide (I; A=4—I, B=NHCOCH₃)

A solution of 23.5 g (0.10 mole) of (l)-N-(3-phenyl-2-oxazolidin-5-ylmethyl)acetamide and 44.2 g of silver trifluoroacetate in 200 ml of chloroform was stirred at ambient temperature as a solution of 27.9 g (0.11 mole) of iodine in 200 ml of chloroform was added. The solid silver trifluoroacetate became coated with a gum. After 4 hours, 20.0 g of silver trifluoroacetate was added and stirring continued an additional 2 hours. The mixture was filtered and the solid was washed with chloroform and dichloromethane. The chloroform solution was then washed with aqueous solution of sodium carbonate. The dried chloroform solution was concentrated to give 10.0 g of crude product, m.p. 147°–170° C. This was recrystallized from acetonitrile to give 8.0 g of the title compound, m.p. 194°–195° C.

EXAMPLE 146

Preparation of
(l)-N-[3-(4-Nitrophenyl)-2-oxooxazolidin-5-ylmethyl]acetamide (I; A=4—NO₂, B=NHCOCH₃)

A 30 ml portion of concentrated sulfuric acid was stirred under dry nitrogen and cooled to −10° C.; 5 g (21.3 mmole) of (l)-N-(3-phenyl-2-oxazolidin-5-ylmethyl)acetamide was added. When all of the solid dissolved, 2.2 g of potassium nitrate was added at −10° to 0° C. The mixture was then allowed to warm to room temperature over a 2 hour period. The mixture was poured onto ice; the product was filtered, washed well with water, and dried. The yield was 3.47 g. A thin layer chromatogram on silica gel plate eluted with chloroform-methanol (9:1) showed a spot R$_f$=0.37 for the p-nitro- and a spot Rf=0.28 for the o-nitro-compound. The product was recrystallized from acetonitrile to give 2.15 g, m.p. 194.5°–195.0° C. NMR confirmed this as the p-nitro product.

EXAMPLE 147

Preparation of
(l)-N-[3-(2,4-Dinitrophenyl)-2-oxooxazolidin-5-ylmethyl]acetamide (I, A=4—NO$_2$, Y=2—NO$_2$, B=NHCOCH$_3$)

The nitration shown in Example 146 was repeated starting with 15 g of (l)-N-(3-phenyl-2-oxazolidin-5-ylmethyl)acetamide. The mother liquor from the crystallization of the crude product (9.82 g) was concentrated and purified by preparative chromatography using the Waters "Prep 500" and silica gel columns, eluting with 9:1 chloroform-methanol. A fast moving component was the pure p-isomer. The slow moving product 1.02 g, m.p. 142.2°-142.6° C. was the 2,4-dinitro compound.

EXAMPLE 148

Preparation of
(l)-N-[3-(2-Nitrophenyl)-2-oxooxazolidin-5-ylmethyl]acetamide (I; A=2—NO$_2$, B=NHCOCH$_3$)

A 90 ml portion of concentrated sulfuric was stirred under dry nitrogen as 11 g of potassium nitrate was added. The mixture became warm and it was cooled in an ice bath to 0°-10° C. as 23.4 g (0.10 mole) of (l)-N-(3-phenyl-2-oxazolidin-5-ylmethyl)acetamide was added slowly. After stirring one hour a thin layer chromatogram showed that there was starting compound left. A further 3 g of potassium nitrate was added and stirring continued two hours. The reaction was poured into ice-water and the product extracted with chloroform. The extract was concentrated and the residue (20 g) was fractionated by preparative chromatography using the Waters Prep 500. The first fraction amounted to 2.8 g, m.p. 130°-136° C. NMR confirmed this as the ortho-nitro product.

EXAMPLE 149

Preparation of
(l)-N-[3-(4-Aminophenyl)-2-oxooxazolidin-5-ylmethyl]acetamide (I; A=4—H$_2$N, B=NHCOCH$_3$)

A mixture of 5.00 g (17.9 mmole) of (l)-N-[3-(4-nitrophenyl)-2-oxooxazolidin-5-ylmethyl]acetamide, 50 ml absolute ethanol and 3 g of Raney nickel catalyst was stirred and heated to 50° C. as a solution of 5 ml of 95% hydrazine diluted with 20 ml of absolute ethanol was added slowly. The temperature rose to reflux and gas was evolved. After refluxing thirty minutes, the solution was filtered and concentrated to a glass which crystallized. This was stirred with acetonitrile and filtered; yield 3.42 g, m.p. 147.5°-148.3° C.

EXAMPLE 150

Preparation of
(l)-N-[3-[4-(Acetylamino)phenyl]-2-oxooxazolidin-5-ylmethyl]acetamide (I; A=4—CH$_3$CONH, B=NHCOCH$_3$)

A 0.95 g portion of the above aniline (Example 149) in 5 ml of tetrahydrofuran and 5 ml of triethylamine, 2 ml of acetic anhydride, 0.01 g 4-dimethylaminopyridine (DMAP) and 10 ml of dimethylacetamide was warmed, then concentrated under reduced pressure, water added and the white solid filtered and washed with water to yield 0.56 g, m.p. 224.1°-224.9° C. (dec.). This was recrystallized from 50 ml of acetonitrile to yield 0.44 g, m.p. 225.5°-225.8° C. (dec).

EXAMPLE 151

Preparation of
(l)-N-[3-[4-(Methylsulfonylamino)phenyl]-2-oxooxazolidin-5-ylmethyl]acetamide (I; A=CH$_3$SO$_2$NH—, B=—NHCOCH$_3$)

A solution of 1.24 g (5 mmole) of the above aniline (Example 149) in 5 ml of pyridine was stirred in an ice-acetone bath under nitrogen as 0.4 ml of methanesulfonyl chloride was added. An intense red color developed and solid separated. The mixture was stirred one hour, diluted with water and made acidic with hydrochloric acid. This was concentrated under reduced pressure and the residue was stirred with acetonitrile and filtered; yield 0.50 g, m.p. 223.5°-224.4° C. This solid is quite water soluble.

EXAMPLE 152

Preparation of
(l)-N-[3-[4-(Acetylthio)phenyl]-2-oxooxazolidin-5-ylmethyl]acetamide (I;

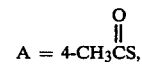

B=NHCOCH$_3$)

A 10.0 g (0.04 mole) portion of (l)-N-(3-phenyl oxooxazolidin-5-ylmethyl)acetamide was chlorosulfonated by adding it to 40 ml of chlorosulfonic acid cooled to 0° C. under nitrogen. The mixture was stirred for 1.5 hours, poured on ice and the white solid filtered and washed well with water and dried. The yield was 13 g, m.p. 134.9°-135.9° C.

The sulfonyl chloride was added to a mixture of 180 ml of acetic acid, 60 ml of acetic anhydride and 30 g of anhydrous sodium acetate, the mixture heated to 75° C., and zinc dust added slowly. The temperature rose to reflux and the zinc was added until it was no longer consumed (16 g). Reflux was then continued for one and one half hours. The cooled mixture was filtered and concentrated. The residue was stirred with tetrahydrofuran, filtered and concentrated, diluted with ether to give 10.1 g, m.p. 130°-180° C. This was dissolved in hot acetonitrile and filtered, concentrated and cooled to yield 5.57 g, m.p. 138.5°-139.1° C.

EXAMPLE 153

Preparation of
(l)-N-[3-(4-Mercaptophenyl)-2-oxooxazolidin-5-ylmethyl]acetamide (I, A=4—HS, B=NHCOCH$_3$)

A 4.1 g of (l)-N-[3-[4-(acetylthio)phenyl]-2-oxooxazolidin-5-ylmethyl]acetamide in 20 ml of absolute ethanol was stirred at 25° C. as 5 ml of pyrrolidine was added. The temperature rose to 40° C., and all of the solid dissolved. Stirring was continued for one hour, the mixture concentrated, diluted with water and filtered to give 3.32 g, m.p. 205°-209° C. (dec.).

EXAMPLE 154

Preparation of
(l)-N-[3-[4-(Cyanomethylthio)phenyl]-2-oxooxazolidin-5-ylmethyl]acetamide (I; A=4—N≡CCH₂S, B=NHCOCH₃)

A suspension of 1.5 g of powdered potassium carbonate in dimethylformamide was stirred under dry nitrogen as 2.5 g (9.4 mmole) of (l)-N-[3-(4-mercaptophenyl)-2-oxooxazolidin-5-ylmethyl]acetamide was added. To this was added 0.65 ml of chloroacetonitrile. After stirring for an hour, the mixture was concentrated. The residue was dissolved in dichloromethane and chromatographed on a 10 inch column of silica gel. The fast moving spot (eluted with 90% dichloromethane, 10% methanol) yield 0.070 g, was recrystallized from ethyl acetate to yield 60 mg, m.p. 90.4° C. using a Metler Melting Point apparatus.

EXAMPLE 155

Preparation of
(l)-N-[3-[4-(Acetylthio)phenyl]-2-oxooxazolidin-5-ylmethyl]carbamic acid (I; A=4—CH₃COS—, B=NHCOOCH₃)

A 12.0 g (48 mmole) of (l)-(3-phenyl-2-oxooxazolidin-5-ylmethyl)carbamic acid methyl ester was added to 60 ml of chlorosulfonic acid cooled to −10° C. under nitrogen. The solid slowly dissolved. The addition required thirty minutes. The mixture was allowed to warm and at 10° C. a very rapid evolution of hydrogen chloride occurred, and all solid dissolved. The stirring was continued two hours at 20°–25° C. and then the reaction was quenched on ice, the solid was filtered and washed well with water and dried in a nitrogen stream. The yield was 14.6 g, m.p. 155.4° C. (Metler apparatus).

The sulfonyl chloride (9 g; 33.7 mmole) was added to a mixture of 145 ml acetic acid, 50 ml acetic anhydride, and 14 g anhydrous sodium acetate and stirred well as 12 g of zinc dust was added. The mixture was refluxed for one hour, cooled, filtered and concentrated. The residue was stirred with water and filtered to give 4.42 g. This was recrystallized from acetonitrile to give 3.22 g, m.p. 156.4°–156.8° C.

EXAMPLE 156

Preparation of
(l)-[3-(4-Mercaptophenyl)-2-oxooxazolidin-5-ylmethyl]carbamic acid, methyl ester (I; A=4—HS, B=NHCOOCH₃)

A mixture of 2.00 g (6.17 mmole) of (l)-[3-[4-(acetylthio)phenyl]-2-oxooxazolidin-5-ylmethyl]carbamic acid, methyl ester in 10 ml of absolute ethanol was stirred under nitrogen as 2 ml of pyrrolidine was added and then refluxed for thirty minutes, concentrated under reduced pressure, diluted with water and made acid with acetic acid. The white solid was filtered, washed with water and dried; yield 1.7 g, m.p. 131.7°–132.6° C.

EXAMPLE 157

Preparation of
(dl)-2-Amino-N-[3-[4-(1-methylethyl)phenyl]-2-oxooxazolidin-5-ylmethyl]acetamide (I; A=4—(CH₃)₂CH, B=NHCOCH₂NH₂)

Part A

A solution of 5 g (16.1 mmole) of (dl)-2-chloro-N-[3-[4-(1-methylethyl)phenyl]-2-oxooxazolidin-5-ylmethyl]acetamide in 50 ml of dry dimethylsulfoxide and 1.5 g sodium azide was stirred and heated to 90° C. under dry nitrogen for five hours. The mixture was concentrated at reduced pressure and the residue stirred with water. A partially crystalline solid separated and solidified on standing, yield 5.8 g. This was recrystallized from ethyl acetate to give 3.4 g, m.p. 122.4–123.4 (dec.). A thin layer chromatogram on silica using 9:1 CHCl₃—methanol indicated that this was a mixture of the starting compound and the desired product. This was used in the next step without further purification.

Part B

A suspension of 3.4 g (dl)-2-Azido-N-[3-[4-(1-methylethyl)phenyl]-2-oxooxazolidin-5-ylmethyl]acetamide in 50 ml of ethanol, 5 ml of water and 5 ml of acetic acid containing 0.5 g 10% palladium-on-charcoal was stirred as hydrogen was passed into the solution through a dispersion tube. The reaction was continued three hours, the solution was filtered and concentrated, the residue with water and made basic with concentrated ammonium hydroxide to give a gummy solid. This was extracted with ethyl acetate, dried over sodium sulfate and concentrated. The residue was stirred with ether and filtered; yield 1.4 g, m.p. 82°–92° C. This was recrystallized from 10 ml of ethyl acetate and a few drops of triethylamine to give 0.84 g, m.p. 105°–107° C.

EXAMPLE 158

Preparation of
1-2-Azido-N-[3-(4-Methylsulfonyl)phenyl]-2-oxooxazolidin-5-ylmethyl]acetamide, (I; A=4—CH₃SO₂, B=NHCOCH₂N₃)

·Substituting 1-2-chloro-N-[3-[4-methylsulfonyl)phenyl]-2-oxooxazolidin-5-ylmethyl]acetamide in the azide displacement of Example 157, Part A gives the title compound, m.p. 188.8°–189.8° C.

EXAMPLE 159

Preparation of
(l)-N-[3-(4-Acetylphenyl)-2-oxooxazolidin-5-ylmethyl]acetamide Oxime

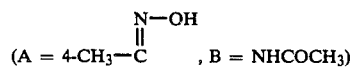
(A = 4-CH₃—C$\overset{\text{N—OH}}{\underset{\|}{}}$ , B = NHCOCH₃)

A mixture of 3.00 g (10.8 mmole) of 1-[3-(4-acetylphenyl)-2-oxooxazolidin-5-ylmethyl]acetamide and 0.85 g of hydroxylamine hydrochloride in 5 ml ethanol and 5 ml of pyridine was refluxed 2.5 hours. After cooling to room temperature, the solvents were concentrated and 5 ml of water was added. The crystalline product was filtered and washed with water; yield 2.44 g. The product was recrystallized from 75 ml nitromethane to give 1.91 g, m.p. 210.0°–212.3° C.

EXAMPLE 160

Preparation of (l)-N-[3-(4-Acetylphenyl)-2-oxooxazolidin-5-ylmethyl]acetamide Oxime, methyl ether

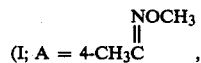

Substitution of methoxyamine hydrochloride for the hydroxylamine hydrochloride in the procedure of Example 159 gave 3.0 g N-[3-(4-acetylphenyl)-2-oxooxazolidin-5-ylmethyl]acetamide oxime methyl ether, m.p. 213.5°–213.7° C.

EXAMPLE 161

Preparation of (l)-N-[3-[4-(Methylthioacetyl)phenyl]-2-oxo-5-oxazolidinylmethyl]acetamide (I; A=4—CH$_3$SCH$_2$CO, B=NHCOCH$_3$)

A mixture of 3.70 g (12 mmole) of l-N-[3-[4-(chloroacetyl)phenyl]-2-oxo-5-oxazolidinylmethyl]acetamide and 1.8 g of potassium methylmercaptide in 25 ml of methanol was stirred. An immediate exotherm occurred and solid separated. The mixture was refluxed two hours, diluted with water and the solid filtered to give 2.0 g of the title compound, m.p. 177.4°–178.2° C.

EXAMPLE 162

Preparation of (l)-N-[3-[4-(Dimethylamino)-1-oxo-2-propenyl]phenyl]-2-oxo-5-oxazolidinylmethyl]acetamide (I; A=4—(CH$_3$)$_2$NCH=CHCO, B=NHCOCH$_3$)

A suspension of 1.50 g of l-N-[3-(4-acetylphenyl)-2-oxo-5-oxazolidinylmethyl]acetamide in 25 ml of absolute ethanol and 3.0 ml of dimethylformamide diethylacetal was refluxed overnight. It was cooled and diluted with ether and filtered to yield 1.2 g of the product as bright yellow crystals, m.p. 189.3°–189.7° C.

EXAMPLE 163

Preparation of (l)-N-[3-[4-(Methylthiomethyl)phenyl]-2-oxo-5-oxazolidinylmethyl]acetamide (I; A=4—CH$_3$SCH$_2$—, B=NHCOCH$_3$)

A solution of 2.34 g (10 mmole) of l-N-[3-[4-phenyl]-2-oxooxazolidin-5-ylmethyl]acetamide in 75 ml of dry dichloromethane was stirred and 1.0 ml of dimethylsulfoxide was added followed by 1.84 ml of trifluoroacetic anhydride. The mixture was stirred one hour under nitrogen then 1.3 ml of stannic chloride was added slowly. A gum separated and the mixture was allowed to stir overnight. A mixture of water, chloroform and isopropanol was added. The resultant tin salts and oxides which separated were dissolved by the addition of 2-aminoethanethiol hydrochloride. The chloroform layer was separated and concentrated to give 1 g of solid. This was purified by dissolving in acetonitrile from which a gum separated and was removed. The clear acetonitrile solution was diluted with ether to give 0.89 g of white crystals, m.p. 127.5°–129.0° C. The NMR showed this to be the desired product.

EXAMPLE 164

Preparation of (l)-N-[3-[4-(Methylsulfinylmethyl)phenyl]-2-oxo-5-oxazolidinylmethyl]acetamide (I; A=4—CH$_3$SOCH$_2$, B=NHCOCH$_3$)

A solution of 1.2 g (4.3 mmole) of l-N-[3-[4-(methylthiomethyl)phenyl]-2-oxo-5-oxazolidinylmethyl]acetamide in 25 ml of acetic acid was stirred at 0° C. as 0.49 g of 30% hydrogen peroxide in 5 ml of acetic acid was added dropwise. The mixture was stirred two hours then concentrated under 1–5 mm pressure and the residue recrystallized from isopropanol to give 900 mg, m.p. 151.5°–152.5° C.

EXAMPLE 165

Preparation of (l)-N-[3-[4-(Methylsulfinyl)acetylphenyl]-2-oxo-5-oxazolidinylmethyl]acetamide dihydrate (I; A=4—CH$_3$SOCH$_2$CO, B=NHCOCH$_3$)

A solution of 1.22 g (3.78 mmole) of l-N-[3-[4-(methylthioacetyl)phenyl]-2-oxo-5-oxazolidinylmethyl]acetamide in 25 ml of acetic acid was stirred at ambient temperature as 0.4 of 30.7% hydrogen peroxide in 2 ml of acetic acid was added. The mixture was stirred two hours and the acetic acid was evaporated in a nitrogen stream. The residue (1.70 g) was recrystallized from 75 ml of acetonitrile to give 830 mg, m.p. 172.6°–172.9° C. The NMR showed that this product was hydrated.

EXAMPLE 166

Preparation of (l)-N-[3-[4-(Bromomethyl)phenyl]-2-oxooxazolidin-5-yl methyl]acetamide (I, A=4—BrCH$_2$—B=NHCOCH$_3$)

A few crystals of azo-bis-isobutyronitrile were added to a warm solution of (l)-N-(3-]4-methylphenyl]-2-oxooxooxazolidin-5-yl-methyl]acetamide (1.77 g) and freshly recrystallized N-bromosuccimmide (0.9 g) in benzene (50 ml). The mixture was stirred and refluxed for 90 minutes and then stirred at room temperature overnight. The yellow crystalline solid that separated was filtered off and washed with benzene. The solid was recrystallized from 2-propanol to yield a pale yellow solid, m.p. 155°–156° (dec.). A second recrystallazation from ethyl acetate using decolorizing charcoal furnished the title compound as colorless crystals, m.p. 162°–164° C. (dec.).

$[\alpha]_D^{26} = -27°$ (c=1 in acetone)

EXAMPLE 167

Preparation of (l)-N-[3-[4-(2-Hydroxyethylthio)phenyl]-2-oxooxazolidin-5-ylmethyl]acetamide (I; A=4—HOCH$_2$CH$_2$S, B=NHCOCH$_3$)

A mixture of 5.5 g (18 mmoles) of (l)-N-[3-[4-(acetylthiophenyl)-2-oxo-oxazolidin-5-ylmethyl]acetamide, 2.47 g of potassium carbonate, and 2.1 ml of 2-iodoethanol was combined in 50 ml of methanol and refluxed with stirring under a nitrogen blanket for two hours.

The reaction mixture was then concentrated to remove most of the methanol, diluted with water, slightly acidified with acetic acid and filtered. The yield was 4.60 g, m.p. 124.5°–125.8° C.

EXAMPLE 168 AND 169

Preparation of the Two Diastereoisomeric Forms of (l)-N-[3-[4-(2-Hydroxyethylsulfinyl)phenyl]-2-oxo-oxazolidin-5-ylmethyl]acetamide (I;

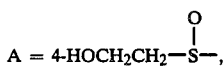

B=NHCOCH$_3$)

A mixture of 3.55 g (11.4 mmole) of (l)-N-[3-[4-(2-hydroxyethylthio)phenyl]-2-oxooxazolidin-5-ylmethyl]acetamide in 25 ml of acetic acid was stirred at ambient temperature then 1.26 g of 30.7% hydrogen peroxide was added slowly. The mixture was stirred two hours, the acetic acid concentrated, the residue diluted with water and filtered. The water was evaporated at reduced pressure to yield 3.61 g, m.p. 127°–130° C. This was crystallized from acetonitrile to give 1.2 g of the title compound enriched in the (R,S) isomer (Example 168), m.p. 166.5°–168.1° C.

$[\alpha]_D^{26} = +19.0° \pm 1.0°$ (c=2 in water)

The mother liquor as concentrated and the residue diluted with 1,2-dimethoxyethane to give 1.9 g of the compound enriched in the (S,S) isomer (Example 169), m.p. 121°–131° C.

$[\alpha]_D^{20} = -76.0° \pm 1.0°$ (c=2 in water)

EXAMPLE 170

Preparation of (l)-3-(4-Acetylphenyl)-5-(aminomethyl)-2-oxazolidinone hydrochloride (I; A=4—CH$_3$CO, B = NH$_3{}^+$Cl$^-$).

Part A

Preparation of (l)-3-(4-Acetylphenyl)-5-(azidomethyl)-2-oxazolidinone (I; A=4—CH$_3$CO, B=N$_3$)

A mixture of 10.0 g (49 mmole) of (l)-5-(azidomethyl)-3-phenyl-2-oxazolidinone in 25 ml of methanesulfonic acid was stirred under nitrogen until the solid dissolved. To this was added 5.2 ml of acetic anhydride slowly. The mixture was stirred three hours at ambient temperature then poured on ice, and extracted with dichloromethane. The dried extract was concentrated to yield 10.9 g of solid. This was purified via chromotograph on silica gel to remove a small amount of starting compound and color. The yield was 6.7 g, m.p. 80.1°–81.1° C.

Part B

A solution of 6.0 g (23 mmole) of (l)-3-(4-acetylphenyl)-5-(azidomethyl)-2-oxazolidinone in 500 ml of 1,2-dimethoxyethane and 3 ml of trimethyl phosphite was warmed to 70° C. for 1.5 hours. At this time a thin layer chromatography showed some starting azide so an additional 1.5 ml of trimethyl phosphite was added, and maintained at 70° C. for of 1.5 hours. A mixture of 2.5 ml of concentrated hydrochloric acid and 2.5 ml of water was added and the mixture was heated at 75° C. overnight. After cooling to 25° C. the solid was filtered and washed with 1,2-dimethoxyethane, and dried to give 5.14 g, m.p. 256°–257° C.

EXAMPLE 171

Preparation of (l)-N-[3-(4-Acetylphenyl)-2-oxo-5-oxazolidinylmethyl]-propanamide (I; A=4—CH$_3$CO—, B=—NHCOCH$_2$CH$_3$)

A solution of 2.35 g (10 mmole) of (l)-3-(4-acetylphenyl)-5-(aminomethyl)-2-oxazolidinone in a mixture of 20 ml of THF, 20 ml of water and 0.8 g of 50% aqueous sodium hydroxide was stirred in an ice bath (0°–10° C.) as a solution of 2 ml of propionic anhydride in 10 ml of THF was added. The pH was maintained between 8–10 during the addition by adding 25% aqueous sodium hydroxide. After the anhydride was all in solution, the mixture was stirred 2 hours, as it warmed to room temperature. The THF was evaporated, the solid filtered off and dried to give 2.33 g, m.p. 209.6°–210.6° C.

Using the proceedure of Examples 171–172, the following compounds have been prepared:

TABLE 8

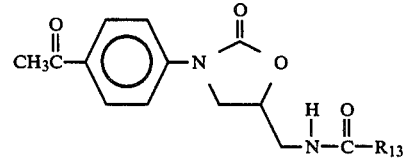

| Ex. | R$_{13}$ | m.p. °C. | Isomer |
|---|---|---|---|
| 172 | CHCl$_2$ | 198.6–199.6 | l |
| 173 | H | 146.9–147.1 | l |
| 174 | CH$_2$Cl | 170.9–171.7 | l |
| 175 | CH$_2$N$_3$ | 143.7–144.1 | l |
| 176 | CH$_2$NH$_2$.HCl | >250 | l |
| 177 | NH$_2$ | 180.5–181.9 | l |
| 178 | CF$_3$ | 170.0–175.0 | l |
| 179 | OCH$_3$ | 167.8–168.1 | l |

EXAMPLE 180

Preparation of (R,S)-N-3-[4-(Methylsulfinyl)phenyl]-2-oxo-5-oxazolidinylmethyl]acetamide (I; A=4—CH$_3$SO—, B=NHCOCH$_3$ A solution containing 100 ml dichloromethane, 3.42 ml of diethyl-L-tartrate (the ester of natural L-tartaric acid) and 3.0 ml of tetraisopropyl orthotitanate was stirred until homogeneous, then 0.15 ml of water was added. The mixture was stirred for fifteen minutes, and then cooled to −20° C. To this was added 2.80 g (10 mmole) of (l)-N-[3-[4-(methylsulfinyl)phenyl]-2-oxazolidin-5-ylmethyl]acetamide and the mixture was stirred while a solution of 1 ml of 90% tert-butyl hydroperoxide in 25 ml of dichloromethane was added slowly. During the addition, the temperature was held at −20° to −30° C. and then allowed to warm to room temperature over one hour. The solution was filtered and concentrated. The residue was taken up into chloroform and chromotographed on a flash column and eluted with 97% chloroform and 3% methanol. A 1.1 g of the desired sulfoxide was obtained, m.p. 173.2°-174° C.;

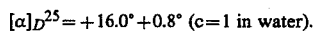

The product was recrystallized from a mixture of acetonitrile and isopropyl acetate to give 800 mg, m.p. 175.5°-175.9° C.

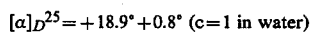

EXAMPLE 181

Preparation of (S,S)-N-[3-[4-(Methylsulfinyl)phenyl]-2-oxo-5-oxazolidinylmethyl]acetamide (I; A=4—CH₃SO—, B=NHCOCH₃)

Using the method of Example 180 above, the oxidation was carried out using diethyl-D-tartrate (the ester of the unnatural D-tartaric acid), to yield the title compound, m.p. 185.1°-185.8° C.

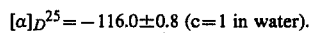

EXAMPLE 182

Preparation of (l)-N-[3-(4-Ethynylphenyl)-2-oxo-5-oxazolidinylmethyl]acetamide (I; A=4—HC≡C, B=NHCOCH₃)

Part A

Preparation of (l)-N-[3-(4-Trimethylsilyl)-ethynyl-phenyl)-2-oxo-5-oxazolidinylmethyl]acetamide (I; A=4—(CH₃)₃SiC≡C, B=NHCOCH₃)

To 5 g of (l)-(3-(4-iodophenyl)-2-oxo-5-oxazolidinylmethyl]acetamide and 1.6 g of trimethylsilylacetylene in 20 ml of dimethylformamide and 20 ml of triethylamine was added 0.193 g of bis(triphenylphosphine)palladium (II) chloride and 0.026 g of copper (I) iodide. After stirring for 4.5 hours at 45° C. the reaction solution was concentrated to a residue. This was dissolved in acetonitrile and ethyl ether and washed with water. The acetonitrile-ethyl ether solution was concentrated to crude solids. The solids were chromatographed on silica gel with an elutant of ethylene glycol dimethyl ether-cyclohexane (1:1). To give 3.4 g of the title compound m.p. 143°-145° C. The mass spectrum of this sample gave a molecular ion peak of 330.

Part B

To a 2 g sample of (l)-N-[3-(4-(trimethylsilyl)ethynylphenyl)-2-oxo-5-oxazolidinylmethyl]acetamide dissolved in approximately 50 ml of methanol was added 10 ml of 1N potassium hydroxide at ambient temperature. After stirring for 90 minutes the reaction solution was acidified to pH of 3 with dilute aqueous hydrochloric acid. After adding water, the acidified solution it was extracted with dichloromethane and concentrated to crude solids. The solids were chromatographed on silica gel (elutant: ethylene glycol dimethyl ether-hexane [1:1]) and then recrystallized from dichloromethane and hexane to yield 0.98 g of the title compound, m.p. 169.5°-171.5° C. The mass spectrum of a sample prepared in a similar fashion gave a molecular ion peak of 258.

EXAMPLE 183

Preparation of (l)-N-[3-[4-(Acetyloxyacetyl)phenyl]-2-oxo-5-oxazolidinylmethyl]acetamide (I; A=4—CH₃OCOCH₂CO, B=NHCOCH₃)

A solution of 2.0 g of (l)-N-[3-[4-(chloroacetyl)-phenyl]-2-oxo-5-oxazolidinylmethyl]acetamide in 50 ml of DMF, 1.0 g of sodium acetate and 200 mg of 18-crown-6 was heated at 50° C. for three hours under nitrogen. The solution was concentrated, and the residue diluted with a 90% chloroform/10% methanol mixture and purified via flash chromatograph on silica gel eluting with the above mentioned solvent system. Recrystallization from acetonitrile gave 700 mg of the title compound, m.p. 182.5°-184° C.

EXAMPLE 184

Preparation of (l)-4-[(5-Acetylaminomethyl)-2-oxo-3-oxazolidinyl]benzoic acid methyl ester (I;

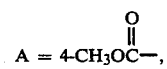

A solution of 2.0 g (5 mmole) of (dl)-N-[3-(4-iodophenyl)-2-oxo-5-oxazolidinylmethyl]acetamide in 30 ml of methanol and 0.86 ml of triethylamine was heated to 45° C. and stirred as carbon monoxide was bubbled into the solution. To this was added 0.022 g of palladium acetate. The mixture was stirred under the carbon monoxide atmosphere for 18 hours at 45° C. The mixture was diluted with chloroform and then washed with saturated ammonium chloride in water. The organic layer was dried over sodium sulfate and concentrated to give 1.34 g of the crude product. This was crystallized from dichloromethane/hexane mixture to give 750 mg, m.p. 177.6°-178.5° C.

EXAMPLE 185

Preparation of (l)-N-[3-(4-Formylphenyl)-2-oxo-5-oxazolidinylmethyl]acetamide (I; A=4—HCO—, B=NHCOCH₃)

A solution of 4.0 g (1.1 mmole) of l-N-[3-(4-iodophenyl)-2-oxo-5-oxazolidinylmethyl]acetamide in 35 ml of THF was warmed to 50° C. under a carbon monoxide atmosphere as 1.2 g of tetrakis (triphenylphosphine) palladium (0) was added. A solution of 3.2 ml (1.1 mmole) of tributyl tin hydride dissolved in 20 ml of toluene was then added over 1.5 hours with a syringe pump. After an additional 0.5 hours ether was added and the white precipitate which formed was filtered and washed well with ether, yield 1.8 g. This solid was recrystallized from ethylacetate to give 750 mg, m.p. 169°-170° C. A mass spectroscopy determination gave a molecular ion of 262.096, calcd. 262.095.

DOSAGE FORMS

The antibacterial agents of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms; kind of concurrent treatment; frequency of treatment; and the effect desired. Usually a daily dosage of active ingredient can be about 5 to 20 milligrams per kilogram of body weight. Ordinarily, when the more potent compounds of this invention are used, 5 to 15, and preferably 5 to 7.5 milligrams per kilogram per day, given in divided doses 2 to 4 times a day or in sustained release form, is effective to obtain desired results. These drugs may also be administered parenterally.

Projected therapeutic levels in humans should be attained by the oral administration of 5–20 mg/kg of body weight given in divided doses two to four times daily. The dosages may be increased in severe or life-threatening infections.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidants such as sodium bisulfate, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 75 milligrams of the active ingredient. The capsules are washed and dried.

TABLETS

A large number of tablets are prepared by conventional procedures so that the dosage unit is 75 milligrams of active ingredient, 0.2 milligrams of colloidal silicon dioxide, 5 milligrams of magnesium stearate, 250 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 75 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Utility

Test results indicate that the novel compounds of this invention are biologically active against gram negative and gram positive bacteria including betalactamase producing *Staphylococcus aureus* isolates. These agents are potentially useful for the treatment of both human and animal bacterial infections including diseases of the respiratory, gastrointestinal, genito-urinary and central nervous systems; blood; interstitial fluids; soft tissue; and bone.

As shown in Table 9, compounds of formula I exert an in vitro antibacterial effect. A standard microdilution method (Conrath, Theodore B., 1972 *Handbook of Microtiter Procedures,* Dynatech Corporation, Cambridge, Mass.) with Mueller-Hinton broth is used to determine the 24-hour minimal inhibitory concentrations (MIC's) for test strains of *Staphylococcus epidermidis* and *Escherichia coli.*

In vitro tests conducted with the compound of Example 123 using the same procedures as described above, resulted in no control of *Staphylococcus aureus* or *Escherichia coli.* It is believed that the compound of Example 123 would provide control at higher concentrations or under different conditions. It was found to exhibit an antibacterial effect in vivo (see Tables 10 and 11).

The in vivo potency of these compounds is exemplified by the data summarized in Tables 10 and 11. Determinations of in vivo efficacy are performed by inoculating mice intraperitoneally with cultures of the infecting organism diluted to produce 90-100% mortality in control animals within twenty-four hours. The diluents used were trypticase soy broth for E. coli and 5% aqueous hog gastric mucin for *Staphylococcus aureus* infections. The compounds are dissolved or suspended in 0.25% aqueous Methocel® (Methocel®: Hydroxypropyl Methylcellulose E15 Premium, Dow Chemical Company) for oral administration or sterile distilled water containing 5% dimethylsulfoxide (Fisher Scientific Company, Fairlawn, N.J.) for subcutaneous administration. The mice are dosed at the time of infection and again at four hours post-infection. Mortality is recorded daily until test termination seven days post infection and the 50 percent effective dose, $ED_{50}$, is calculated by the Reed-Muench method (Reed, L. G. and Muench, H., "A simple method of estimating fifty percent end points," *American Journal of Hygiene,* 27, 493-497 (1938).

TABLE 9

IN VITRO BROTH DILUTION
MINIMAL INHIBITORY CONCENTRATIONS

| Ex. No. | Microdilution Broth MIC in μg/ml | |
|---|---|---|
| | *Staphylococcus epidermidis* | *Escherichia coli* |
| 2 | 6.3 | >100.0 |
| 3 | 25.0 | >100.0 |
| 4 | >200.0 | >200.0 |
| 5 | 200.0 | >200.0 |
| 7 | 100.0 | >200.0 |
| 10 | 50.0 | >100.0 |
| 11 | >100.0 | >100.0 |
| 12 | >100.0 | >100.0 |
| 15 | >200.0 | >200.0 |
| 17 | >200.0 | >200.0 |
| 21 | 6.3 | 100.0 |
| 22 | 2.4 | 9.4 |
| 23 | 3.2 | 25.0 |
| 24 | >100.0 | >100.0 |
| 25 | 100.0 | >100.0 |
| 26 | 6.3 | 100.0 |
| 27 | 6.3 | 50.0 |
| 28 | 12.5 | 50.0 |
| 29 | 12.5 | 100.0 |
| 30 | 200.0 | >200.0 |
| 31 | 3.9 | >200.0 |
| 32 | 12.5 | >200.0 |
| 33 | 50.0 | >200.0 |

TABLE 9-continued

IN VITRO BROTH DILUTION
MINIMAL INHIBITORY CONCENTRATIONS

| Ex. No. | Microdilution Broth MIC in μg/ml | |
|---|---|---|
| | *Staphylococcus epidermidis* | *Escherichia coli* |
| 34 | 25.0 | >200.0 |
| 35 | 25.0 | 200.0 |
| 36 | 25.0 | >200.0 |
| 37 | 200.0 | >200.0 |
| 38 | 9.4 | >200.0 |
| 39 | 12.5 | >200.0 |
| 40 | 12.5 | >200.0 |
| 41 | 12.5 | >200.0 |
| 42 | 100.0 | >200.0 |
| 44 | 100.0 | >200.0 |
| 45 | 37.5 | >200.0 |
| 46 | 12.5 | >200.0 |
| 51 | 3.1 | >200.0 |
| 52 | 6.3 | >200.0 |
| 57 | 12.5 | 100.0 |
| 59 | 100.0 | >200.0 |
| 62 | 50.0 | >200.0 |
| 67 | 3.2 | 2.5 |
| 68 | 100.0 | >200.0 |
| 69 | 9.4 | 150.0 |
| 70 | 50.0 | >200.0 |
| 71 | 50.0 | >200.0 |
| 72 | 25.0 | 200.0 |
| 73 | >200.0 | >200.0 |
| 74 | 100.0 | >200.0 |
| 75 | >200.0 | >200.0 |
| 76 | >200.0 | >200.0 |
| 77 | 200.0 | >200.0 |
| 78 | >200.0 | >200.0 |
| 79 | 200.0 | >200.0 |
| 80 | 25.0 | >200.0 |
| 81 | 6.2 | >200.0 |
| 82 | 3.1 | >200.0 |
| 83 | 12.5 | >200.0 |
| 84 | >128.0 | >128.0 |
| 86 | 6.25 | >200.0 |
| 87 | 100.0 | >200.0 |
| 88 | >200.0 | >200.0 |
| 89 | 25.0 | >200.0 |
| 90 | 25.0 | >200.0 |
| 91 | 25.0 | >200.0 |
| 92 | 50.0 | >200.0 |
| 93 | 50.0 | >200.0 |
| 94 | 18.8 | 200.0 |
| 95 | 12.5 | >200.0 |
| 96 | 12.5 | >50.0 |
| 97 | 3.1 | >200.0 |
| 99 | 25.0 | >200.0 |
| 100 | 12.5 | >200.0 |
| 101 | 4.0 | 128.0 |
| 102 | 16.0 | >128.0 |
| 103 | 12.5 | >50.0 |
| 104 | 32.0 | >128.0 |
| 105 | 1.0 | >128.0 |
| 106 | 64.0 | >128.0 |
| 107 | 2.0 | >128.0 |
| 108 | 2.0 | >128.0 |
| 112 | 12.5 | 50.0 |
| 113 | 25.0 | 100.0 |
| 114 | 200.0 | 200.0 |
| 115 | 37.5 | >200.0 |
| 116 | 12.5 | >200.0 |
| 117 | 200.0 | >200.0 |
| 120 | 10.0 | >200.0 |
| 121 | 18.8 | >200.0 |
| 122 | >200.0 | >200.0 |
| 123 | >200.0 | >200.0 |
| 124 | >200.0 | >200.0 |
| 128 | >200.0 | >200.0 |
| 129 | 0.4 | 12.5 |
| 130 | 3.1 | 50.0 |
| 131 | 3.1 | 100.0 |
| 132 | 6.2 | >200.0 |
| 133 | 1.6 | >200.0 |
| 134 | 0.4 | 25.0 |
| 135 | 0.15 | 100.0 |

TABLE 9-continued

IN VITRO BROTH DILUTION
MINIMAL INHIBITORY CONCENTRATIONS

Microdilution Broth MIC in μg/ml

| Ex. No. | Staphylococcus epidermidis | Escherichia coli |
|---|---|---|
| 136 | 6.25 | >200.0 |
| 138 | 1.0 | >128.0 |
| 140 | 4.0 | 128.0 |
| 141 | 8.0 | >128.0 |
| 142 | 1.0 | >128.0 |
| 143 | 16.0 | >128.0 |
| 145 | 12.5 | >200.0 |
| 146 | 2.4 | 200.0 |
| 147 | 200.0 | >200.0 |
| 148 | 200.0 | >200.0 |
| 149 | 100.0 | >200.0 |
| 150 | 200.0 | >200.0 |
| 151 | 200.0 | >200.0 |
| 152 | >200.0 | >200.0 |
| 153 | >50.0 | >50.0 |
| 154 | 3.2 | >200.0 |
| 155 | >200.0 | >200.0 |
| 156 | >200.0 | >200.0 |
| 157 | 50.0 | >200.0 |
| 158 | 6.3 | 50.0 |
| 159 | 4.0 | >128.0 |
| 160 | 12.5 | >200.0 |
| 161 | 1.6 | >200.0 |
| 162 | 32.0 | >128.0 |
| 163 | 2.0 | >128.0 |
| 164 | 16.0 | >128.0 |
| 165 | 12.5 | >200.0 |
| 166 | 64.0 | >128.0 |
| 167 | 3.1 | >200.0 |
| 168 | 25.0 | >200.0 |
| 169 | 50.0 | 200.0 |
| 170 | >128.0 | >128.0 |
| 171 | 4.0 | >128.0 |
| 172 | 4.0 | >128.0 |
| 173 | 4.0 | >128.0 |
| 174 | 1.0 | 32.0 |
| 175 | 4.0 | 128.0 |
| 176 | 32.0 | >128.0 |
| 177 | 4.0 | >128.0 |
| 178 | 16.0 | >128.0 |
| 179 | 4.0 | 128.0 |
| 180 | 4.0 | 128.0 |
| 181 | 16.0 | >128.0 |
| 182 | 16.0 | >128.0 |
| 183 | 0.5 | 64.0 |
| 184 | 4.0 | >128.0 |
| 185 | >128.0 | >128.0 |

TABLE 10

IN VIVO EFFICACY OF ORALLY ADMINISTERED
COMPOUNDS IN MOUSE INTRAPERITONEAL
INFECTIONS

| | Infecting Bacterial Organism | |
|---|---|---|
| Ex. No. | Staphylococcus aureus $ED_{50}$ (mg/kg) | Escherichia coli $ED_{50}$ (mg/kg) |
| 2 | 7.3 | 52.6 |
| 3 | 29.3 | >120.0 |
| 4 | 43.3 | N.T. |
| 5 | 172.0 | N.T. |
| 7 | 24.2 | N.T. |
| 11 | 29.9 | 47.4 |
| 12 | 179.0 | N.T. |
| 15 | 40.0 | N.T. |
| 17 | >120.0 | N.T. |
| 21 | 7.3 | 30.3 |
| 22 | 14.2 | 71.1 |
| 23 | 3.3 | 14.0 |
| 24 | 74.3 | N.T. |
| 25 | >360.0 | N.T. |
| 26 | 1.7 | 56.2 |
| 27 | 8.0 | 37.0 |
| 28 | 71.3 | N.T. |
| 29 | 88.7 | N.T. |
| 30 | >120.0 | N.T. |
| 31 | 3.5 | 19.6 |
| 32 | 3.5 | 70.9 |
| 33 | 12.2 | >120.0 |
| 34 | >120.0 | N.T. |
| 35 | 35.8 | N.T. |
| 36 | 4.7 | 47.2 |
| 37 | 62.9 | N.T. |
| 38 | 9.1 | >120.0 |
| 39 | 6.1 | >120.0 |
| 40 | 53.1 | N.T. |
| 41 | 5.3 | >120.0 |
| 42 | 45.5 | N.T. |
| 44 | 30.3 | N.T. |
| 45 | >120.0 | N.T. |
| 46 | 15.8 | 62.5 |
| 51 | 6.4 | 62.9 |
| 52 | 4.9 | >120.0 |
| 57 | 10.8 | 39.0 |
| 59 | 4.3 | 88.0 |
| 62 | 19.1 | >120.0 |
| 67 | 42.5 | >120.0 |
| 68 | 48.0 | N.T. |
| 69 | 11.9 | 65.7 |
| 70 | 51.7 | N.T. |
| 71 | >120.0 | N.T. |
| 72 | >120.0 | N.T. |
| 73 | 59.5 | N.T. |
| 74 | 96.6 | N.T. |
| 75 | 130.0 | N.T. |
| 76 | 58.0 | N.T. |
| 79 | 99.8 | N.T. |
| 80 | 64.0 | N.T. |
| 81 | 47.9 | >120.0 |
| 82 | 2.7 | 65.9 |
| 83 | 9.6 | >120.0 |
| 84 | 79.2 | >120.0 |
| 86 | 6.9 | >40.0 |
| 87 | 42.0 | >120.0 |
| 88 | 23.6 | >120.0 |
| 89 | 11.0 | >138.0 |
| 90 | 11.3 | 98.4 |
| 91 | 50.7 | N.T. |
| 92 | 31.0 | N.T. |
| 93 | >120.0 | N.T. |
| 94 | 30.2 | 76.8 |
| 95 | 10.9 | >120.0 |
| 96 | 7.9 | 83.2 |
| 97 | 4.9 | N.T. |
| 99 | 77.4 | N.T. |
| 100 | 19.5 | N.T. |
| 101 | 10.6 | N.T. |
| 102 | 24.0 | N.T. |
| 105 | 10.8 | N.T. |
| 107 | >60.0 | N.T. |
| 108 | 8.4 | N.T. |
| 112 | >360.0 | >360.0 |
| 113 | 17.2 | 29.7 |
| 114 | 15.3 | 10.5 |
| 115 | >120.0 | N.T. |
| 116 | 25.9 | N.T. |
| 117 | 16.1 | >120.0 |
| 120 | 3.3 | 11.1 |
| 121 | 2.5 | 55.9 |
| 122 | 48.4 | >120.0 |
| 123 | 27.6 | N.T. |
| 124 | 48.4 | >120.0 |
| 128 | 62.0 | N.T. |
| 129 | 0.7 | 13.6 |
| 130 | 2.1 | 17.4 |
| 131 | <4.4 | N.T. |
| 132 | <4.4 | 24.7 |
| 133 | 3.0 | 17.9 |

TABLE 10-continued

IN VIVO EFFICACY OF ORALLY ADMINISTERED COMPOUNDS IN MOUSE INTRAPERITONEAL INFECTIONS

| | Infecting Bacterial Organism | |
|---|---|---|
| Ex. No. | Staphylococcus aureus $ED_{50}$ (mg/kg) | Escherichia coli $ED_{50}$ (mg/kg) |
| 134 | <4.4 | 46.9 |
| 135 | <4.4 | 100.0 |
| 136 | N.T. | 100.0 |
| 138 | 9.6 | >120.0 |
| 140 | 6.6 | N.T. |
| 141 | 40.2 | N.T. |
| 142 | 1.8 | 52.1 |
| 143 | 20.8 | N.T. |
| 145 | 50.0 | N.T. |
| 146 | 2.0 | 29.8 |
| 147 | 44.4 | N.T. |
| 148 | 21.0 | >120.0 |
| 149 | 20.2 | >120.0 |
| 150 | 56.9 | N.T. |
| 151 | 62.9 | N.T. |
| 152 | 4.4 | 24.8 |
| 153 | 5.7 | 17.0 |
| 155 | 3.0 | 82.2 |
| 156 | 4.5 | >120.0 |
| 157 | 58.9 | N.T. |
| 158 | 11.4 | 56.5 |
| 159 | 2.6 | N.T. |
| 160 | <4.4 | N.T. |
| 161 | 10.4 | >120.0 |
| 162 | .11.3 | N.T. |
| 163 | 5.4 | N.T. |
| 164 | 14.0 | N.T. |
| 165 | 16.4 | N.T. |
| 167 | 68.2 | N.T. |
| 168 | 49.8 | N.T. |
| 169 | 99.1 | N.T. |
| 170 | 32.3 | N.T. |
| 171 | 3.3 | N.T. |
| 172 | 10.2 | >120.0 |
| 173 | 6.9 | N.T. |
| 174 | 8.1 | N.T. |
| 175 | 6.6 | N.T. |
| 176 | 30.9 | N.T. |
| 177 | 3.7 | N.T. |
| 178 | 31.6 | N.T. |
| 179 | 2.0 | N.T. |
| 180 | 2.5 | N.T. |
| 181 | 2.8 | N.T. |
| 182 | 16.0 | N.T. |
| 183 | 9.1 | N.T. |
| 184 | >60.0 | N.T. |

[1] $ED_{50}$ = 50 Percent effective dose in mg/kg
[2] N.T. = Not tested.

TABLE 11

IN VIVO EFFICACY OF COMPOUNDS ADMINISTERED SUBCUTANEOUSLY IN MOUSE INTRAPERITONEAL INFECTIONS

| | Infecting Bacterial Organism | |
|---|---|---|
| Ex. No. | Staphylococcus aureus $ED_{50}$ (mg/kg) | Escherichia coli $ED_{50}$ (mg/kg) |
| 5 | 41.2 | N.T. |
| 7 | 33.7 | N.T. |
| 11 | 16.4 | N.T. |
| 12 | 89.8 | N.T. |
| 15 | 24.9 | N.T. |
| 17 | 24.9 | N.T. |
| 22 | N.T. | 11.8 |
| 25 | 83.6 | >100.0 |
| 26 | N.T. | 40.7 |
| 30 | 57.4 | >120.0 |
| 31 | <4.4 | N.T. |
| 32 | <4.4 | N.T. |
| 33 | 8.6 | N.T. |
| 34 | 49.6 | N.T. |
| 36 | 7.4 | >120.0 |
| 38 | 4.8 | 60.4 |
| 39 | 5.5 | >120.0 |
| 41 | 6.1 | N.T. |
| 42 | 20.9 | N.T |
| 45 | 9.6 | N.T. |
| 46 | >13.0 | 91.0 |
| 57 | N.T. | 12.9 |
| 67 | 18.6 | 99.0 |
| 71 | 69.3 | N.T. |
| 72 | 15.2 | N.T. |
| 77 | 70.9 | N.T. |
| 78 | 67.1 | N.T. |
| 79 | 85.1 | N.T. |
| 80 | 42.3 | N.T. |
| 81 | 27.9 | >120.0 |
| 82 | 2.0 | 95.1 |
| 83 | 6.6 | >12.0 |
| 84 | 80.5 | N.T. |
| 86 | 4.7 | >40.0 |
| 87 | 10.5 | >120.0 |
| 88 | 21.9 | >120.0 |
| 94 | 18.7 | 46.7 |
| 95 | 7.7 | 60.7 |
| 97 | 9.5 | >120.0 |
| 99 | 20.1 | N.T. |
| 100 | 10.5 | N.T. |
| 101 | 4.8 | N.T. |
| 102 | 9.0 | N.T. |
| 105 | 13.8 | N.T. |
| 107 | 18.6 | N.T. |
| 108 | 20.4 | N.T. |
| 112 | 14.4 | 62.7 |
| 113 | 9.6 | 11.7 |
| 114 | N.T. | 12.5 |
| 115 | 9.6 | N.T. |
| 116 | 14.9 | N.T. |
| 117 | 7.2 | >120.0 |
| 120 | 2.8 | 6.1 |
| 122 | 16.3 | >120.0 |
| 123 | 46.6 | N.T. |
| 124 | 16.3 | >120.0 |
| 128 | 33.6 | N.T. |
| 129 | 0.5 | 14.0 |
| 130 | <1.3 | 26.3 |
| 131 | <4.4 | N.T. |
| 132 | 6.9 | >120.0 |
| 133 | 2.2 | 15.2 |
| 134 | <4.4 | 42.1 |
| 135 | <4.4 | 100.0 |
| 136 | <4.4 | 100.0 |
| 138 | 5.1 | >120.0 |
| 140 | 13.2 | N.T. |
| 141 | 20.8 | N.T. |
| 142 | 1.8 | 52.1 |
| 143 | 11.9 | N.T. |
| 145 | 12.2 | >120.0 |
| 146 | >13.0 | 40.0 |
| 148 | 21.5 | N.T. |
| 149 | 10.3 | N.T. |
| 150 | 12.5 | N.T. |
| 151 | 9.7 | N.T. |
| 152 | <2.5 | N.T. |
| 153 | <13.0 | 57.2 |
| 155 | <4.4 | N.T. |
| 156 | <4.4 | N.T. |
| 157 | 19.6 | N.T. |
| 158 | <13.0 | 25.0 |
| 159 | 1.1 | 71.9 |
| 160 | <4.4 | N.T. |
| 161 | 5.4 | >120.0 |
| 162 | 20.9 | N.T. |
| 163 | 3.2 | 33.3 |
| 164 | 9.4 | >120.0 |

TABLE 11-continued

IN VIVO EFFICACY OF COMPOUNDS ADMINISTERED SUBCUTANEOUSLY IN MOUSE INTRAPERITONEAL INFECTIONS

| | Infecting Bacterial Organism | |
|---|---|---|
| Ex. No. | *Staphylococcus aureus* $ED_{50}$ (mg/kg) | *Escherichia coli* $ED_{50}$ (mg/kg) |
| 165 | 8.4 | >120.0 |
| 167 | 10.8 | N.T. |
| 168 | 24.3 | N.T. |
| 169 | 12.1 | N.T. |
| 170 | 25.3 | N.T. |
| 171 | 1.6 | 21.6 |
| 172 | 13.6 | >120.0 |
| 173 | 4.5 | 79.0 |
| 174 | 12.2 | >120.0 |
| 175 | 8.2 | 73.5 |
| 176 | 11.2 | N.T. |
| 177 | 2.8 | 34.0 |
| 178 | 31.6 | N.T. |
| 179 | 1.7 | 83.1 |
| 180 | 0.8 | N.T. |
| 181 | 1.0 | N.T. |
| 182 | 7.0 | >120.0 |
| 183 | 3.4 | N.T. |
| 184 | 37.5 | N.T. |
| 185 | 35.9 | N.T. |

[1] $ED_{50}$ = 50 percent effective dose in mg/kg
[2] N.T. = Not tested.

What is claimed is:

1. A compound of the formula

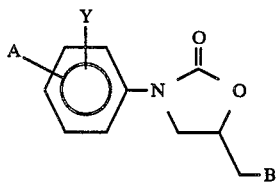 (I)

wherein, for the l, and mixtures of the d and l stereoisomers of the compound,

A is $-NO_2$, $-S(O)_nR_1$, $-S(O)_2-N=S(O)_pR_2R_3$, $-SH$,

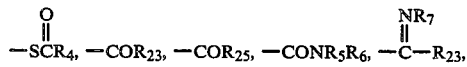

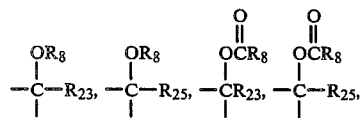

$-CN$, $-OR_5$, halogen, $-NR_5R_6$, 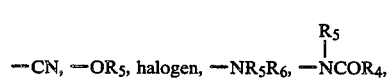

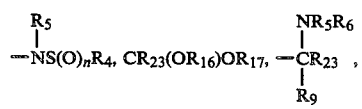

alkyl of 1 to 8 carbons, optionally substituted with one or more halogen atoms, OH, =O other than at alpha position, $S(O)_nR_{24}$, $NR_5R_6$, alkenyl of 2-5 carbons, alkynyl of 2-5 carbons or cycloalkyl of 3-8 carbons;

$R_1$ is $C_1-C_4$ alkyl, optionally substituted with one or more halogen atoms, OH, CN, $NR_5R_6$ or $CO_2R_8$; $C_2-C_4$ alkenyl; $-NR_9R_{10}$; $-N_3$;

$-NX_2$; $NR_9X$ $--NXZ^+$;

$R_2$ and $R_3$ are independently $C_1-C_2$ alkyl or, taken together are $-(CH_2)_q-$;

$R_4$ is alkyl of 1-4 carbons, optionally substituted with one or more halogens;

$R_5$ and $R_6$ are independently H, alkyl of 1-4 carbons or cycloalkyl of 3-8 carbons;

$R_7$ is $-NR_5R_6$, $-OR_5$ or

$R_8$ is H or alkyl of 1-4 carbons;
$R_9$ is H, $C_1-C_4$ alkyl or $C_3-C_8$ cycloalkyl;
$R_{10}$ is H, $C_1-C_4$ alkyl, $C_2-C_4$ alkenyl, $C_3-C_4$ cycloalkyl, $-OR_8$ or $-NR_{11}R_{11A}$;
$R_{11}$ and $R_{11A}$ are independently H or $C_1-C_4$ alkyl, or taken together, are $-(CH_2)_r-$;
X is Cl, Br or I;
Y is H, F, Cl, Br, alkyl of 1-3 carbons, or $NO_2$, or A and Y taken together can be $-O-(CH_2)_t O-$;
Z is a physiologically acceptable cation;
n is 0, 1 or 2;
p is 0 or 1;
q is 3, 4 or 5;
r is 4 or 5;
t is 1, 2 or 3;
B is $-NH_2$,

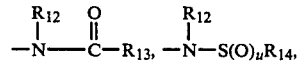

or $N_3$;

$R_{12}$ is H, $C_1-C_{10}$ alkyl or $C_3-C_8$ cycloalkyl;
$R_{13}$ is H; $C_1-C_4$ alkyl optionally substituted with one or more halogen atoms; $C_2-C_4$ alkenyl; $C_3-C_4$ cycloalkyl; phenyl; $-CH_2OR_{15}$; $-CH(OR_{16})OR_{17}$; $-CH_2S(O)_vR_{14}$;

$-OR_{18}$; $-SR_{14}$; $-CH_2N_3$; the aminoalkyl groups derived from α-amino acids such as glycine, L-alanine, L-cysteine, L-proline, and D-alanine; $-NR_{19}R_{20}$; or $C(NH_2)R_{21}R_{22}$;

$R_{14}$ is $C_1-C_4$ alkyl, optionally substituted with one or more halogen atoms;

$R_{15}$ is H or $C_1-C_4$ alkyl, optionally substituted with one or more halogen atoms;

$R_{16}$ and $R_{17}$ are independently $C_1-C_4$ alkyl or, taken together, are $-(CH_2)_m-$;

$R_{18}$ is $C_1-C_4$ alkyl or $C_7-C_{11}$ aralkyl;
$R_{19}$ and $R_{20}$ are independently H or $C_1-C_2$ alkyl;
$R_{21}$ and $R_{22}$ are independently H, $C_1-C_4$ alkyl, $C_3-C_6$ cycloalkyl, phenyl or, taken together, are $-(CH_2)_s-$;

u is 1 or 2;
v is 0, 1 or 2;

m is 2 or 3;
s is 2, 3, 4 or 5; and
$R_{23}$ is H, alkyl of 1-8 carbons optionally substituted with one or more halogens, or cycloalkyl of 3-8 carbons;
$R_{24}$ is alkyl of 1-4 carbons or cycloalkyl of 3-8 carbons;
$R_{25}$ is alkyl of 1-4 carbons substituted with one or more of $-S(O)_nR_{24}$, $-OR_8$,

$-NR_5R_6$, or alkenyl of 2-5 carbons optionally substituted with CHO; or a pharmaceutically suitable salt thereof; provided that:

(1) when A is $CH_3S-$, then B is not

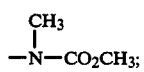

(2) when A is $CH_3SO_2-$, then B is not

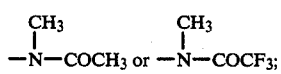

(3) when A is $H_2NSO_2-$ and B is

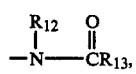

then $R_{12}$ is H;
(4) when A is $-CN$, B is not $-N_3$;
(5) when A is $(CH_3)_2CH$, B is not $NHCOCH_2Cl$;
(6) when A is $OR_5$, then B is not $NH_2$;
(7) when A is F, then B is not $NHCO_2CH_3$.

2. A compound of the formula

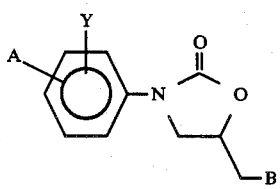

(I)

wherein, for the l, and mixtures of the d and l stereoisomers of the compound,

A is $-NO_2$, $-S(O)_nR_1$, $-S(O)_2-N=S(O)_pR_2R_3$, $-SH$,

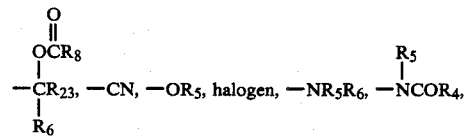

-continued

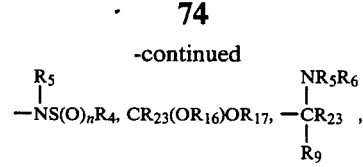

alkyl of 1 to 5 carbons, optionally substituted with one or more halogen atoms, alkenyl of 2-5 carbons, alkynyl of 2-5 carbons or cycloalkyl of 3-8 carbons;
$R_1$ is $C_1-C_4$ alkyl, optionally substituted with one or more halogen atoms, CN, $NR_5R_6$ or $CO_2R_8$; $C_2-C_4$ alkenyl; $-NR_9R_{10}$; $-N_3$;

$-NX_2$; $NR_9X$ $-NXZ+$;
$R_2$ and $R_3$ are independently $C_1-C_2$ alkyl or, taken together are $-(CH_2)_q-$;
$R_4$ is alkyl of 1-4 carbons, optionally substituted with one or more halogens;
$R_5$ and $R_6$ are independently H, alkyl of 1-4 carbons or cycloalkyl of 3-8 carbons;
$R_7$ is $-NR_5R_6$, $-OR_5$ or

$R_8$ is H or alkyl of 1-4 carbons;
$R_9$ is H, $C_1-C_4$ alkyl or $C_3-C_8$ cycloalkyl;
$R_{10}$ is H, $C_1-C_4$ alkyl, $C_2-C_4$ alkenyl, $C_3-C_4$ cycloalkyl, $-OR_8$ or $-NR_{11}R_{11A}$;
$R_{11}$ and $R_{11A}$ are independently H or $C_1-C_4$ alkyl, or taken together, are $-(CH_2)_r-$;
X is Cl, Br or I;
Y is H, F, Cl, Br or $NO_2$, or A and Y taken together can be $-O-(CH_2)_tO-$;
Z is a physiologically acceptable cation;
n is 0, 1 or 2;
p is 0 or 1;
q is 3, 4, or 5;
r is 4 or 5;
t is 1, 2 or 3;
B is $-NH_2$,

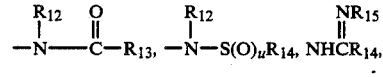

or $N_3$;
$R_{12}$ is H, $C_1-C_{10}$ alkyl or $C_3-C_8$ cycloalkyl;
$R_{13}$ is H; $C_1-C_4$ alkyl optionally substituted with one or more halogen atoms; $C_2-C_4$ alkenyl; $C_3-C_4$ cycloalkyl; phenyl; $-CH_2OR_{15}$; $-CH(OR_{16})OR_{17}$; $-CH_2S(O)_vR_{14}$;

$-OR_{18}$; $-SR_{14}$; $-CH_2N_3$; the aminoalkyl groups derived from α-amino acids such as glycine, L-alanine, L-cysteine, L-proline, and D-alanine; $-NR_{19}R_{20}$; or $C(NH_2)R_{21}R_{22}$;
$R_{14}$ is $C_1-C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —$(CH_2)_m$—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —$(CH_2)_s$;

u is 1 or 2;

v is 0, 1 or 2;

m is 2 or 3;

s is 2, 3, 4 or 5; and $R_{23}$ is H, alkyl of 1-4 carbons optionally substituted with one or more halogens, or cycloalkyl of 3-8 carbons; or a pharmaceutically suitable salt thereof; provided that:

(1) when A is $CH_3S$—, then B is not

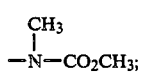

(2) when A is $CH_3SO_2$—, then B is not

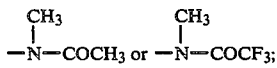

(3) when A is $H_2NSO_2$— and B is

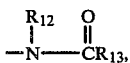

when $R_{12}$ is H;

(4) when A is —CN, B is not —$N_3$;

(5) when A is $(CH_3)_2CH$, B is not $NHCOCH_2Cl$;

(6) when A is $OR_5$, then B is not $NH_2$;

(7) when A is F, then B is not $NHCO_2CH_3$.

3. A compound of the formula

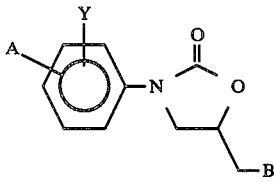

wherein, for the l, and mixtures of the d and l stereoisomers of the compound,

A is —$NO_2$, —$S(O)_nR_1$, —$S(O)_2$—$N=S(O)_pR_2R_3$, —SH,

alkyl of 1 to 5 carbons, optionally substituted with one or more halogen atoms, alkenyl of 2-5 carbons or cycloalkyl of 3-8 carbons;

$R_1$ is $C_1$-$C_4$ alkyl, optionally substituted with one or more halogen atoms, CN, $NR_5R_6$ or $CO_2R_8$; $C_2$-$C_4$ alkenyl; —$NR_9R_{10}$; —$N_3$;

—$NX_2$; $NR_9X$ —$NXZ^+$;

$R_2$ and $R_3$ are independently $C_1$-$C_2$ alkyl or, taken together are —$(CH_2)_q$—;

$R_4$ is alkyl of 1-4 carbons, optionally substituted with one or more halogens;

$R_5$ and $R_6$ are independently H, alkyl of 1-4 carbons or cycloalkyl of 3-8 carbons;

$R_7$ is —$NR_5R_6$ or —$OR_5$;

$R_8$ is H or alkyl of 1-4 carbons;

$R_9$ is H, $C_1$-$C_4$ alkyl or $C_3$-$C_8$ cycloalkyl;

$R_{10}$ is H, $C_1$-$C_4$ alkyl, $C_2$-$C_4$ alkenyl, $C_3$-$C_4$ cycloalkyl, —$OR_8$ or —$NR_{11}R_{114}$;

$R_{11}$ and $R_{114}$ are independently H or $C_1$-$C_4$ alkyl, or taken together, are —$(CH_2)_r$—;

X is Cl, Br or I;

Y is H, F, Cl, Br or $NO_2$, or A and Y taken together can be —$O(CH_2)_tO$—;

Z is a physiologically acceptable cation;

n is 0, 1 or 2;

p is 0 or 1;

q is 3, 4 or 5;

r is 4 or 5;

t is 1, 2 or 3;

B is —$NH_2$,

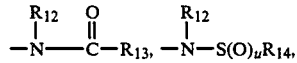

or $N_3$;

$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; —$CH_2OR_{15}$; —$CH(OR_{16})OR_{17}$; —$CH_2S(O)_vR_{14}$;

—$OR_{18}$; —$SR_{14}$; —$CH_2N_3$; the aminoalkyl groups derived from α-amino acids such as glycine, L-alanine, L-cysteine, L-proline, and D-alanine; —$NR_{19}R_{20}$; or $C(NH_2)R_{21}R_{22}$;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are —$(CH_2)_m$—;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl, phenyl or, taken together, are —$(CH_2)_s$—;

u is 1 or 2;

v is 0, 1 or 2;

m is 2 or 3;

s is 2, 3, 4 or 5; and $R_{23}$ is independently H, alkyl of 1-4 carbons or cycloalkyl of 3-8 carbons; or a pharmaceutically suitable salt thereof; provided that:

(1) when A is $CH_3S$—, then B is not

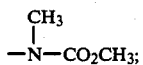

(2) when A is CH$_3$SO$_2$—, then B is not

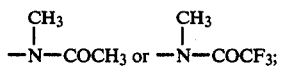

(3) when A is H$_2$NSO$_2$— and B is

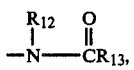

then R$_{12}$ is H;
(4) when A is —CN, B is not —N$_3$;
(5) when A is (CH$_3$)$_2$CH, B is not NHCOCH$_2$Cl;
(6) when A is OR$_5$, then B is not NH$_2$.

4. A compound of the formula

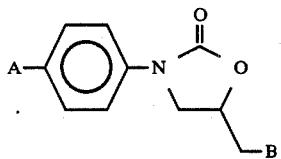

(I)

wherein, for the l, and mixtures of the d and l stereoisomers of the compound,

A is —NO$_2$, —S(O)$_n$R$_1$, or —S(O)$_2$—N=S(O)$_p$R$_2$R$_3$;
R$_1$ is C$_1$-C$_4$ alkyl optionally substituted with one or more halogen atoms, C$_2$-C$_4$ alkenyl, —NR$_9$R$_{10}$, —N$_3$, —NX$_2$, —NR$_9$X or —NXZ$^+$;
R$_2$ and R$_3$ are independently C$_1$-C$_2$ alkyl or, taken together, are —(CH$_2$)$_q$—;
R$_9$ is H, C$_1$-C$_4$ alkyl or C$_3$-C$_8$ cycloalkyl;
R$_{10}$ is H, C$_1$-C$_4$ alkyl, C$_2$-C$_4$ alkenyl, C$_3$-C$_4$ cycloalkyl, —OR$_8$ or —NR$_{11}$R$_{11A}$;
X is Cl, Br or I; Z is a physiologically acceptable cation;
R$_8$ is H or C$_1$-C$_4$ alkyl;
R$_{11}$ and R$_{11A}$ are independently H or C$_1$-C$_4$ alkyl, or, taken together, are —(CH$_2$)$_r$—;
n is 0, 1 or 2;
p is 0 or 1;
q is 3, 4 or 5;
r is 4 or 5;
B is —NH$_2$,

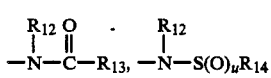

or N$_3$;
R$_{12}$ is H, C$_1$-C$_{10}$ alkyl or C$_3$-C$_8$ cycloalkyl;
R$_{13}$ is H; C$_1$-C$_4$ alkyl optionally substituted with one or more halogen atoms; C$_2$-C$_4$ alkenyl; C$_3$-C$_4$ cycloalkyl; phenyl; —CH$_2$OR$_{15}$; —CH(OR$_{16}$)OR$_{17}$; —CH$_2$S(O)$_v$R$_{14}$; —OR$_{18}$; —SR$_{14}$; the aminoalkyl groups derived from α-amino acids such as glycine, L-alanine, L-cysteine, L-proline, and D-alanine; or —NR$_{19}$R$_{20}$;
R$_{14}$ is C$_1$-C$_4$ alkyl, optionally substituted with one or more halogen atoms;

R$_{15}$ is C$_1$-C$_4$ alkyl optionally substituted with one or more halogen atoms;
R$_{16}$ and R$_{17}$ are independently C$_1$-C$_4$ alkyl or, taken together are —(CH$_2$)$_m$—;
R$_{18}$ is C$_1$-C$_4$ alkyl or C$_7$-C$_{11}$ aralkyl;
R$_{19}$ and R$_{20}$ are independently H or C$_1$-C$_2$ alkyl;
u is 1 or 2;
v is 0, 1 or 2; and
m is 2 or 3; or a pharmaceutically suitable salt thereof; provided that:
(1) when A is CH$_3$S—, then B is not

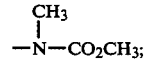

(2) when A is CH$_3$SO$_2$—, then B is not

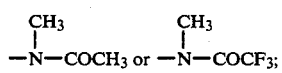

(3) when A is H$_2$NSO$_2$— and B is

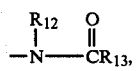

then R$_{12}$ is H.

5. A compound of claim 1 wherein Y is H.
6. A compound of claim 2 wherein Y is H.
7. A compound of claim 5 wherein, for the l, and mixtures of the d and l stereoisomers of the compound, A, substituted in the para position is —NO$_2$, —COR$_{23}$, —COR$_{25}$, —S(O)$_n$R$_1$ or —S(O)$_2$—N=S(O)$_p$R$_2$R$_3$;
R$_1$ is C$_1$-C$_4$ alkyl optionally substituted with one or more halogen atoms, C$_2$-C$_4$ alkenyl, —NR$_9$R$_{10}$, —N$_3$, —NX$_2$, —NR$_9$X or —NXZ$^+$;
R$_2$ and R$_3$ are independently C$_1$-C$_2$ alkyl or, taken together, are —(CH$_2$)$_q$—;
R$_9$ is H, C$_1$-C$_4$ alkyl or C$_3$-C$_8$ cycloalkyl;
R$_{10}$ is H, C$_1$-C$_4$ alkyl, C$_2$-C$_4$ alkenyl, C$_3$-C$_4$ cycloalkyl, —OR$_8$ or —NR$_{11}$R$_{11A}$;
X is Cl, Br or I;
Z is a physiologically acceptable cation;
R$_8$ is H or C$_1$-C$_4$ alkyl;
R$_{11}$ and R$_{11A}$ are independently H or C$_1$-C$_4$ alkyl, or, taken together, are —(CH$_2$)$_r$—;
n is 0, 1 or 2;
p is 0 or 1;
q is 3, 4 or 5;
r is 4 or 5;
B is —NH$_2$,

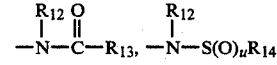

or N$_3$;
R$_{12}$ is H, C$_1$-C$_{10}$ alkyl or C$_3$-C$_8$ cycloalkyl;
R$_{13}$ is H; C$_1$-C$_4$ alkyl optionally substituted with one or more halogen atoms; C$_2$-C$_4$ alkenyl; C$_3$-C$_4$ cycloalkyl; phenyl; —CH$_2$OR$_{15}$; —CH(OR$_{13}$)OR$_{14}$; —CH$_2$S(O)$_v$R$_{14}$; —OR$_{18}$; —SR$_{14}$; the aminoalkyl groups derived from α-amino acids such as glycine, L-alanine, L-cysteine, L-proline, and D-alanine; or —NR$_{19}$R$_{20}$;

$R_{14}$ is $C_1$–$C_4$ alkyl, optionally substituted with one or more halogen atoms;

$R_{15}$ is H or $C_1$–$C_4$ alkyl optionally substituted with one or more halogen atoms;

$R_{16}$ and $R_{17}$ are independently $C_1$–$C_4$ alkyl or, taken together, are —$(CH_2)_m$—;

$R_{18}$ is $C_1$–$C_4$ alkyl or $C_7$–$C_{11}$ aralkyl;

$R_{19}$ is H or $C_1$–$C_4$ alkyl;

$R_{20}$ is H or $C_1$–$C_2$ alkyl;

$R_{23}$ is H, alkyl of 1–4 carbons optionally substituted with one or more halogens, or cycloalkyl of 3–8 carbons;

u is 1 or 2;

v is 0, 1 or 2; and m is 2 or 3; or a pharmaceutically suitable salt thereof; provided that:

(1) when A is $CH_3S$—, then B is not

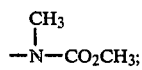

(2) when A is $CH_3SO_2$—, then B is not

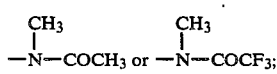

(3) when A is $H_2NSO_2$— and B is

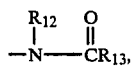

then $R_{12}$ is H.

8. A compound of claim 6 wherein, for the 1, and mixtures of the d and l stereoisomers of the compound, A, substituted in the para position is —$NO_2$, —$COR_{23}$, —$S(O)_nR_1$ or —$S(O)_2$—$N=S(O)_pR_2R_3$;

$R_1$ is $C_1$–$C_4$ alkyl optionally substituted with one or more halogen atoms, $C_2$–$C_4$ alkenyl, —$NR_9R_{10}$, —$N_3$, —$NX_2$, —$NR_9X$ or —$NXZ^+$;

$R_2$ and $R_3$ are independently $C_1$–$C_2$ alkyl or, taken together, are —$(CH_2)_q$—;

$R_9$ is H, $C_1$–$C_4$ alkyl or $C_3$–$C_8$ cycloalkyl;

$R_{10}$ is H, $C_1$–$C_4$ alkyl, $C_2$–$C_4$ alkenyl, $C_3$–$C_4$ cycloalkyl, —$OR_8$ or —$NR_{11}R_{11A}$;

X is Cl, Br or I;

Z is a physiologically acceptable cation;

$R_8$ is H or $C_1$–$C_4$ alkyl;

$R_{11}$ and $R_{11A}$ are independently H or $C_1$–$C_4$ alkyl, or, taken together, are —$(CH_2)_r$—;

n is 0, 1 or 2;

p is 0 or 1;

q is 3, 4 or 5;

r is 4 or 5;

B is —$NH_2$,

or $N_3$;

$R_{12}$ is H, $C_1$–$C_{10}$ alkyl or $C_3$–$C_8$ cycloalkyl;

$R_{13}$ is H; $C_1$–$C_4$ alkyl optionally substituted with one or more halogen atoms; $C_2$–$C_4$ alkenyl; $C_3$–$C_4$ cycloalkyl; phenyl; —$CH_2OR_{15}$; —$CH(OR_{13})OR_{14}$; —$CH_2S(O)_vR_{14}$; —$OR_{18}$; —$SR_{14}$; the aminoalkyl groups derived from α-amino acids such as glycine, L-alanine, L-cysteine, L-proline, and D-alanine; or —$NR_{19}R_{20}$;

$R_{14}$ is $C_1$–$C_4$ alkyl, optionally substituted with one or more halogen atoms;

$R_{15}$ is H or $C_1$–$C_4$ alkyl optionally substituted with one or more halogen atoms;

$R_{16}$ and $R_{17}$ are independently $C_1$–$C_4$ alkyl or, taken together, are —$(CH_2)_m$—;

$R_{18}$ is $C_1$–$C_4$ alkyl or $C_7$–$C_{11}$ aralkyl;

$R_{19}$ is H or $C_1$–$C_4$ alkyl;

$R_{20}$ is H or $C_1$–$C_2$ alkyl;

$R_{23}$ is H, alkyl of 1–4 carbons optionally substituted with one or more halogens, or cycloalkyl of 3–8 carbons;

u is 1 or 2;

v is 0, 1 or 2; and m is 2 or 3; or a pharmaceutically suitable salt thereof; provided that:

(1) when A is $CH_3S$—, then B is not

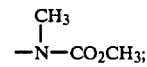

(2) when A is $CH_3SO_2$—, then B is not

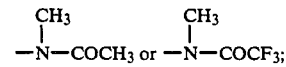

(3) when A is $H_2NSO_2$— and B is

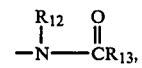

then $R_{12}$ is H.

9. A compound of claim 1 wherein Y is H;

A, substituted in the para position, is —$S(O)_nR_1$, $NO_2$,

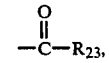

—$COCH_2OCOCH_3$, —$CH(CH_3)_2$, —$CH_2CH_3$, or $CH_3CH(OH)$—;

$R_1$ is $C_1$–$C_2$ alkyl optionally substituted with one or more halogen atoms or $NR_5R_6$;

$R_5$ is H or $CH_3$;

$R_6$ is H or $CH_3$;

$R_{23}$ is alkyl of 1–3 carbons; and n is 0, 1 or 2 when $R_1$ is alkyl or substituted alkyl; n is 2 when $R_1$ is $NR_5R_6$.

10. A compound of claim 2 wherein Y is H;

A, substituted in the para position, is —$S(O)_nR_1$, $NO_2$,

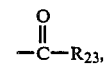

—$CH(CH_3)_2$, —$CH_2CH_3$, or $CH_3CH(OH)$—;

$R_1$ is $C_1$–$C_2$ alkyl optionally substituted with one or more halogen atoms or $NR_5R_6$;

$R_5$ is H or $CH_3$;

$R_6$ is H or $CH_3$;

4,705,799

$R_{23}$ is alkyl of 1-3 carbons; and n is 0, 1 or 2 when $R_1$ is alkyl or substituted alkyl; n is 2 when $R_1$ is $NR_5R_6$.

11. A compound of claim 2 wherein B is $$-NH-\overset{O}{\underset{\|}{C}}-R_{13};$$

$R_{13}$ is H, $CH_3$, $OR_{18}$, $CHCl_2$, $CH_2Cl$ or $CH_2OR_{15}$;
$R_{15}$ is H or $C_1$-$C_4$ alkyl; and
$R_{18}$ is $C_1$-$C_4$ alkyl.

12. A compound of claim 2 with the stereo-chemical configuration

[structure with A-phenyl-N-oxazolidinone-B, H shown]

wherein
A is $-S(O)CH_3$, $-S-CH_3$, $-S(O)_2CH_3$, $SO_2NH_2$, $-COR_{23}$ where $R_{23}$ is alkyl of 1-3 carbons, $-CH(CH_3)_2$, $-CH_2CH_3$, or $CH_3CH(OH)-$.

13. A compound of claim 12 wherein $R_{23}$ is $CH_3$.

14. A compound of claim 2 with the stereo-chemical formula

[structure with A-phenyl-N-oxazolidinone-B, H shown]

wherein
B is $$-\overset{H}{\underset{|}{N}}-\overset{O}{\underset{\|}{C}}-CH_3, \quad -\overset{H}{\underset{|}{N}}-\overset{O}{\underset{\|}{C}}-OCH_3 \text{ or } -\overset{H}{\underset{|}{N}}-\overset{O}{\underset{\|}{C}}-CHCl_2.$$

15. A compound of claim 12 wherein B is $$-\overset{H}{\underset{|}{N}}-\overset{O}{\underset{\|}{C}}-CH_3, \quad -\overset{H}{\underset{|}{N}}-\overset{O}{\underset{\|}{C}}-OCH_3 \text{ or } -\overset{H}{\underset{|}{N}}-\overset{O}{\underset{\|}{C}}-CHCl_2.$$

16. A compound of claim 15 wherein $R_{23}$ is $CH_3$.

17. The compound of claim 2 which is (l)-N-[3-[4-(methylsulfonyl)phenyl]-2-oxooxazolidin-5-ylmethyl]-carbamic acid, methyl ester.

18. The compound of claim 2 which is (l)-N-[3-[4-(methylthio)phenyl]-2-oxooxazolidin-5-ylmethyl]carbamic acid, methyl ester.

19. The compound of claim 2 which is (l)-N-[3-[4-(methylsulfonyl)phenyl]-2-oxooxazolidin-5-ylmethyl]-formaide.

20. The compound of claim 2 which is (l)-N-[3-[4-(methylsulfonyl)phenyl]-2-oxooxazolidin-5-ylmethyl]acetamide.

21. The compound of claim 2 which is (l)-N-[3-[4-(methylthio)phenyl]-2-oxooxazolidin-5-ylmethyl]acetamide.

22. The compound of claim 2 which is (l)-N-[3-[4-(aminosulfonyl)phenyl]-2-oxooxazolidin-5-ylmethyl]-acetamide.

23. The compound of claim 2 which is (l)-N-[3-[4-(methylsulfinyl)phenyl]-2-oxooxazolidin-5-ylmethyl-]acetamide.

24. The compound of claim 2 which is (l)-2,2-dichloro-N-[3-[4-(methylsulfonyl)phenyl]-2-oxooxazolidin-5-ylmethyl]acetamide.

25. The compound of claim 2 which is (l)-N-[3-[4-(isopropylphenyl)-2-oxooxazolidin-5-ylmethyl]acetamide.

26. The compound of claim 2 which is (l)-N-[3-[4-acetylphenyl)-2-oxooxazolidin-5-ylmethyl]acetamide.

27. The compound of claim 2 which is (l)-N-[3-[4-(1-hydroxyethyl)phenyl]-2-oxo-5-oxazolidinylmethyl-]acetamide.

28. The compound of claim 19 which is its R,S isomer, its S,S isomer, or a mixture thereof.

29. The compound of claim 2 which is l-N-[3-(4-ethylphenyl)-2-oxooxazolidin-5-ylmethyl]acetamide.

30. The compound of claim 1 which is l-N-[3-[3-(4-acetyloxyacetyl)phenyl]-2-oxooxazolidinyl-5-ylmethyl-]acetamide.

31. The compound of claim 2 which is l-N-[2-oxo-3-[4-(1-oxobutyl)phenyl]-5-oxazolidinylmethyl]acetamide.

32. The compound of claim 2 which is l-N-[2-oxo-3-[4-(1-oxopropyl)phenyl]-5-oxazolidinylmethyl]acetamide.

33. A compound having the formula:

(Ia)
[structure showing Y-phenyl-N-oxazolidinone-NHR$_{12}$]

wherein, for the l, and mixtures of the d and l stereoisomers of the compound,
$R_{12}$ is H, $C_1$-$C_{10}$ alkyl or $C_3$-$C_8$ cycloalkyl; and
Y is H, F, Cl, Br, or $No_2$.

34. A compound of claim 33 wherein Y is H.

35. A compound of the formula (Ib)
[structure showing Y-phenyl-N-oxazolidinone with N($R_{12}$)-C(O)-$R_{13}$ side chain]

wherein, for the l, and mixtures of the d and l stereoisomers of the compound,
Y is H, F, Cl, Br or $NO_2$;
$R_{12}$ is H, $C_1$-$C_{10}$ alkyl or $C_3$-$C_8$ cycloalkyl;

$R_{13}$ is H; $C_1$-$C_4$ alkyl optionally substituted with one or more halogen atoms; $C_2$-$C_4$ alkenyl; $C_3$-$C_4$ cycloalkyl; phenyl; $-CH_2OR_{15}$; $-CH(OR_{16})OR_{17}$; $-CH_2S(O)_vR_{14}$;

$-OR_{18}$; $-SR_{14}$; the aminoalkyl groups derived from α-amino acids such as glycine, L-alanine, L-cysteine, L-proline, and D-alanine; $-NR_{19}R_{20}$; or $C(NH_2)R_{21}R_{22}$;

$R_{14}$ is $C_1$-$C_4$ alkyl, optionally substituted with one or more halogen atoms;

$R_{15}$ is H or $C_1$-$C_4$ alkyl, optionally substituted with one or more halogen atoms;

$R_{16}$ and $R_{17}$ are independently $C_1$-$C_4$ alkyl or, taken together, are $-(CH_2)_m-$;

$R_{18}$ is $C_1$-$C_4$ alkyl or $C_7$-$C_{11}$ aralkyl;

$R_{19}$ and $R_{20}$ are independently H or $C_1$-$C_2$ alkyl;

$R_{21}$ and $R_{22}$ are independently H, $C_1$-$C_4$ alkyl, $C_3$-$C_6$ cycloalkyl phenyl or, taken together, are $-(CH_2)_s-$;

m is 2 or 3;

v is 0, 1 or 2; and s is 2, 3, 4 or 5.

36. A compound of claim 35 wherein Y is H.

37. A pharmaceutical composition comprising a suitable pharmaceutical carrier and an antibacterially effective amount of a compound of claim 1.

38. A pharmaceutical composition comprising a suitable pharmaceutical carrier and an antibacterially effective amount of a compound of claim 2.

39. A pharmaceutical composition comprising a suitable pharmaceutical carrier and an antibacterially effective amount of a compound of claim 3.

40. A pharmaceutical composition comprising a suitable pharmaceutical carrier and an antibacterially effective amount of a compound of claim 4.

41. A pharmaceutical composition comprising a suitable pharmaceutical carrier and an antibacterially effective amount of a compound of claim 5.

42. A pharmaceutical composition comprising a suitable pharmaceutical carrier and an antibacterially effective amount of a compound of claim 6.

43. A pharmaceutical composition comprising a suitable pharmaceutical carrier and an antibacterially effective amount of a compound of claim 7.

44. A pharmaceutical composition comprising a suitable pharmaceutical carrier and an antibacterially effective amount of a compound of claim 8.

45. A pharmaceutical composition comprising a suitable pharmaceutical carrier and an antibacterially effective amount of a compound of claim 9.

46. A pharmaceutical composition comprising a suitable pharmaceutical carrier and an antibacterially effective amount of a compound of claim 10.

47. A pharmaceutical composition comprising a suitable pharmaceutical carrier and an antibacterially effective amount of a compound of claim 11.

48. A pharmaceutical composition comprising a suitable pharmaceutical carrier and an antibacterially effective amount of a compound of claim 12.

49. A pharmaceutical composition comprising a suitable pharmaceutical carrier and an antibacterially effective amount of a compound of claim 13.

50. A pharmaceutical composition comprising a suitable pharmaceutical carrier and an antibacterially effective amount of a compound of claim 14.

51. A pharmaceutical composition comprising a suitable pharmaceutical carrier and an antibacterially effective amount of a compound of claim 15.

52. A pharmaceutical composition comprising a suitable pharmaceutical carrier and an antibacterially effective amount of a compound of claim 16.

53. A pharmaceutical composition comprising a suitable pharmaceutical carrier and an antibacterially effective amount of the compound of claim 17.

54. A pharmaceutical composition comprising a suitable pharmaceutical carrier and an antibacterially effective amount of the compound of claim 18.

55. A pharmaceutical composition comprising a suitable pharmaceutical carrier and an antibacterially effective amount of the compound of claim 19.

56. A pharmaceutical composition comprising a suitable pharmaceutical carrier and an antibacterially effective amount of the compound of claim 20.

57. A pharmaceutical composition comprising a suitable pharmaceutical carrier and an antibacterially effective amount of the compound of claim 21.

58. A pharmaceutical composition comprising a suitable pharmaceutical carrier and an antibacterially effective amount of the compound of claim 22.

59. A pharmaceutical composition comprising a suitable pharmaceutical carrier and an antibacterially effective amount of the compound of claim 23.

60. A pharmaceutical composition comprising a suitable pharmaceutical carrier and an antibacterially effective amount of the compound of claim 24.

61. A pharmaceutical composition comprising a suitable pharmaceutical carrier and an antibacterially effective amount of the compound of claim 25.

62. A pharmaceutical composition comprising a suitable pharmaceutical carrier and an antibacterially effective amount of the compound of claim 26.

63. A pharmaceutical composition comprising a suitable pharmaceutical carrier and an antibacterially effective amount of the compound of claim 27.

64. A pharmaceutical composition comprising a suitable pharmaceutical carrier and an antibacterially effective amount of the compound of claim 28.

65. A pharmaceutical composition comprising a suitable pharmaceutical carrier and an antibacterially effective amount of the compound of claim 29.

66. A pharmaceutical composition comprising a suitable pharmaceutical carrier and an antibacterially effective amount of the compound of claim 30.

67. A pharmaceutical composition comprising a suitable pharmaceutical carrier and an antibacterially effective amount of the compound of claim 31.

68. A pharmaceutical composition comprising a suitable pharmaceutical carrier and an antibacterially effective amount of the compound of claim 32.

69. A method for alleviating bacterial infection in a mammal which comprises administering to the mammal an antibacterially effective amount of at least one compound having the formula:

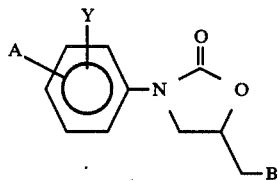

(I)

wherein, for the l, and mixtures of the d and l stereoisomers of the compound,

A is —NO$_2$, —S(O)$_n$R$_1$, —S(O)$_2$—N=S(O)$_p$R$_2$R$_3$, —SH,

A is —NO$_2$, —S(O)$_n$R$_1$, —S(O)$_2$—N=S(O)$_p$R$_2$R$_3$, —SH,

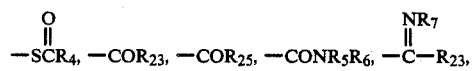

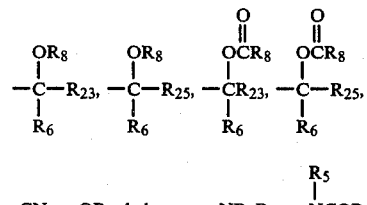

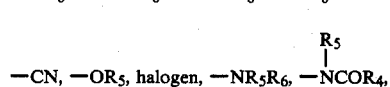

—CN, —OR$_5$, halogen, —NR$_5$R$_6$, —NCOR$_4$,

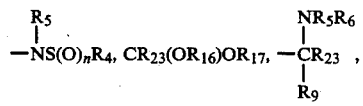

alkyl of 1 to 8 carbons, optionally substituted with one or more halogen atoms, OH, =O other than at alpha position, S(O)$_n$R$_{24}$, NR$_5$R$_6$, alkenyl of 2-5 carbons, alkynyl of 2-5 carbons or cycloalkyl of 3-8 carbons;

R$_1$ is C$_1$-C$_4$ alkyl, optionally substituted with one or more halogen atoms, OH, CN, NR$_5$R$_6$ or CO$_2$R$_8$; C$_2$-C$_4$ alkenyl; —NR$_9$R$_{10}$; —N$_3$;

—NX$_2$; NR$_9$X—NXZ+;

R$_2$ and R$_3$ are independently C$_1$-C$_2$ alkyl or, taken together are —(CH$_2$)$_q$—;

R$_4$ is alkyl of 1–4 carbons, optionally substituted with one or more halogens;

R$_5$ and R$_6$ are independently H, alkyl of 1–4 carbons or cycloalkyl of 3–8 carbons;

R$_7$ is —NR$_5$R$_6$, —OR$_5$ or

R$_8$ is H or alkyl of 1–4 carbons;
R$_9$ is H, C$_1$-C$_4$ alkyl or C$_3$-C$_8$ cycloalkyl;
R$_{10}$ is H, C$_1$-C$_4$ alkyl, C$_2$-C$_4$ alkenyl, C$_3$-C$_4$ cycloalkyl, —OR$_8$ or —NR$_{11}$R$_{11A}$;

R$_{11}$ and R$_{11A}$ are independently H or C$_1$-C$_4$ alkyl, or taken together, are —(CH$_2$)$_r$—;

X is Cl, Br or I;

Y is H, F, Cl, Br, alkyl of 1-3 carbons, or NO$_2$, or A and Y taken together can be —O—(CH$_2$)$_t$O—;

Z is a physiologically acceptable cation;
n is 0, 1 or 2;
p is 0 or 1;
q is 3, 4 or 5;
r is 4 or 5;
t is 1, 2 or 3;
B is —NH$_2$,

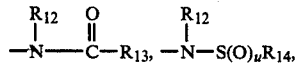

or N$_3$;

R$_{12}$ is H, C$_1$-C$_{10}$ alkyl or C$_3$-C$_8$ cycloalkyl;
R$_{13}$ is H; C$_1$-C$_4$ alkyl optionally subsituted with one or more halogen atoms; C$_2$-C$_4$ alkenyl; C$_3$-C$_4$ cycloalkyl; phenyl; —CH$_2$OR$_{15}$; —CH(OR$_{16}$)OR$_{17}$; —CH$_2$S(O)$_v$R$_{14}$;

—OR$_{18}$; —SR$_{14}$; —CH$_2$N$_3$; the aminoalkyl groups derived from α-amino acids such as glycine, L-alanine, L-cysteine, L-proline, and D-alanine; —NR$_{19}$R$_{20}$; or C(NH$_2$)R$_{21}$R$_{22}$;

R$_{14}$ is C$_1$-C$_4$ alkyl, optionally substituted with one or more halogen atoms;

R$_{15}$ is H or C$_1$-C$_4$ alkyl, optionally substituted with one or more halogen atoms;

R$_{16}$ and R$_{17}$ are independently C$_1$-C$_4$ alkyl or, taken together, are —(CH$_2$)$_m$—;

R$_{18}$ is C$_1$-C$_4$ alkyl or C$_7$-C$_{11}$ aralkyl;
R$_{19}$ and R$_{20}$ are independently H or C$_1$-C$_2$ alkyl;
R$_{21}$ and R$_{22}$ are independently H, C$_1$-C$_4$ alkyl, C$_3$-C$_6$ cycloalkyl, phenyl or, taken together, are —(CH$_2$)$_s$—;

u is 1 or 2;
v is 0, 1 or 2;
m is 2 or 3;
s is 2, 3, 4 or 5; and
R$_{23}$ is H, alkyl of 1-8 carbons optionally substituted with one or more halogens, or cycloalkyl of 3-8 carbons;

R$_{24}$ is alkyl of 1-4 carbons or cycloalkyl of 3-8 carbons;

R$_{25}$ is alkyl of 1-4 carbons substituted with one or more of —S(O)$_n$R$_{24}$, —OR$_8$,

—NR$_5$R$_6$, or alkenyl of 2-5 carbons optionally substituted with CHO; or a pharmaceutically suitable salt thereof; provided that:

(1) when A is CH$_3$S—, then B is not

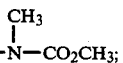

(2) when A is CH$_3$SO$_2$—, then B is not

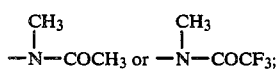

(3) when A is H$_2$NSO$_2$— and B is

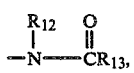

then R$_{12}$ is H;
(4) when A is —CN, B is not —N$_3$;
(5) when A is (CH$_3$)$_2$CH, B is not NHCOCH$_2$Cl;
(6) when A is F, then B is not NHCO$_2$CH$_3$.

70. A method for alleviating bacterial infection in a mammal which comprises administering to the mammal an antibacterially effective amount of at least one compound having the formula

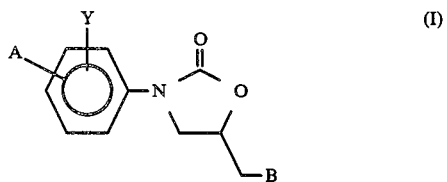

(I)

wherein, for the l, and mixtures of the d and l stereoisomers of the compound,

A is —NO$_2$, —S(O)$_n$R$_1$, —S(O)$_2$—N=S(O)$_p$R$_2$R$_3$, —SH,

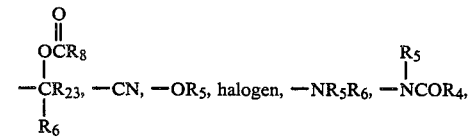

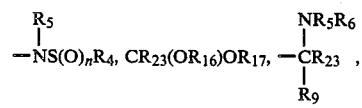

alkyl of 1 to 5 carbons, optionally substituted with one or more halogen atoms, alkenyl of 2-5 carbons, alkynyl of 2-5 carbons or cycloalkyl of 3-8 carbons;

R$_1$ is C$_1$-C$_4$ alkyl, optionally substituted with one or more halogen atoms, CN, NR$_5$R$_6$ or CO$_2$R$_8$; C$_2$-C$_4$ alkenyl; —NR$_9$R$_{10}$; —N$_3$;

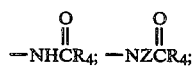

—NX$_2$; NR$_9$X —-NXZ+;

R$_2$ and R$_3$ are independently C$_1$-C$_2$ alkyl or, taken together are —(CH$_2$)$_q$—;

R$_4$ is alkyl of 1-4 carbons, optionally substituted with one or more halogens;

R$_5$ and R$_6$ are independently H, alkyl of 1-4 carbons or cycloalkyl of 3-8 carbons;

R$_7$ is —NR$_5$R$_6$, —OR$_5$ or

R$_8$ is H or alkyl of 1-4 carbons;
R$_9$ is H, C$_1$-C$_4$ alkyl or C$_3$-C$_8$ cycloalkyl;
R$_{10}$ is H, C$_1$-C$_4$ alkyl, C$_2$-C$_4$ alkenyl, C$_3$-C$_4$ cycloalkyl, —OR$_8$ or —NR$_{11}$R$_{114}$;
R$_{11}$ and R$_{114}$ are independently H or C$_1$-C$_4$ alkyl, or taken together, are —(CH$_2$)$_r$—;
X is Cl, Br or I;
Y is H, F, Cl, Br or NO$_2$, or A and Y taken together can be —O—(CH$_2$)$_t$O—;
Z is a physiologically acceptable cation;
n is 0, 1 or 2;
p is 0 or 1;
q is 3, 4 or 5;
r is 4 or 5;
t is 1, 2 or 3;
B is —NH$_2$,

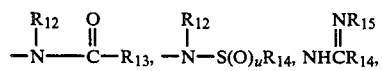

or N$_3$;
R$_{12}$ is H, C$_1$-C$_{10}$ alkyl or C$_3$-C$_8$ cycloalkyl;
R$_{13}$ is H; C$_1$-C$_4$ alkyl optionally substituted with one or more halogen atoms; C$_2$-C$_4$ alkenyl; C$_3$-C$_4$ cycloalkyl; phenyl; —CH$_2$OR$_{15}$; —CH(OR$_{16}$)OR$_{17}$; —CH$_2$S(O)$_v$R$_{14}$;

—OR$_{18}$; —SR$_{14}$; —CH$_2$N$_3$; the aminoalkyl groups derived from α-amino acids such as glycine, L-alanine, L-cysteine, L-proline, and D-alanine; —NR$_{19}$R$_{20}$; or C(NH$_2$)R$_{21}$R$_{22}$;
R$_{14}$ is C$_1$-C$_4$ alkyl, optionally substituted with one or more halogen atoms;
R$_{15}$ is H or C$_1$-C$_4$ alkyl, optionally substituted with one or more halogen atoms;
R$_{16}$ and R$_{17}$ are independently C$_1$-C$_4$ alkyl or, taken together, are —(CH$_2$)$_m$—;
R$_{18}$ is C$_1$-C$_4$ alkyl or C$_7$-C$_{11}$ aralkyl;
R$_{19}$ and R$_{20}$ are independently H or C$_1$-C$_2$ alkyl;
R$_{21}$ and R$_{22}$ are independently H, C$_1$-C$_4$ alkyl, C$_3$-C$_6$ cycloalkyl, phenyl or, taken together, are —(CH$_2$)$_s$;
u is 1 or 2;
v is 0, 1 or 2;
m is 2 or 3;
s is 2, 3, 4 or 5; and
R$_{23}$ is H, alkyl of 1-4 carbons optionally substituted with one or more halogens, or cycloalkyl of 3-8 carbons; or a pharmaceutically suitable salt thereof; provided that:
(1) when A is CH$_3$S—, then B is not

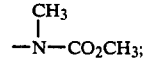

(2) when A is CH₃SO₂—, then B is not

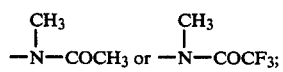

(3) when A is H₂NSO₂— and B is

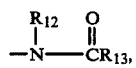

then $R_{12}$ is H;
(4) when A is —CN, B is not —N₃;
(5) when A is (CH₃)₂CH, B is not NHCOCH₂Cl;
(6) when A is F, then B is not NHCO₂CH₃.

71. A method for alleviating bacterial infection in a mammal which comprises administering to the mammal an antibacterially effective amount of at least one compound having the formula:

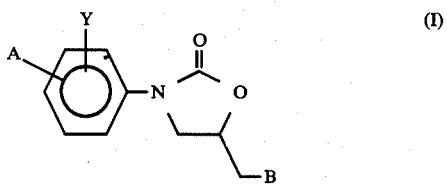

(I)

wherein, for the l, and mixtures of the d and l stereoisomers of the compound,
A is —NO₂, —S(O)$_n$R₁, —S(O)₂—N=S(O)$_p$R₂R₃, —SH, $$-\overset{O}{\underset{\|}{S}}CR_4, -COR_{23}, -CONR_5R_6, -\overset{NR_7}{\underset{\|}{C}}-R_{23}, -CN, -OR_5,$$

$$-NR_5R_6, -\overset{R_5}{\underset{|}{N}}COR_4, -\overset{R_5}{\underset{|}{N}}S(O)_nR_4,$$

alkyl of 1 to 5 carbons, optionally substituted with one or more halogen atoms, alkenyl of 2–5 carbons or cycloalkyl of 3–8 carbons;
$R_1$ is $C_1$-$C_4$ alkyl, optionally substituted with one or more halogen atoms, CN, NR₅R₆ or CO₂R₈; $C_2$-$C_4$ alkenyl; —NR₉R₁₀; —N₃;

$$-\overset{O}{\underset{\|}{N}}HCR_4; -\overset{O}{\underset{\|}{N}}ZCR_4;$$

—NX₂; NR₉X—⁻NXZ⁺;
$R_2$ and $R_3$ are independently $C_1$-$C_2$ alkyl or, taken together are —(CH₂)$_q$—;
$R_4$ is alkyl of 1–4 carbons, optionally substituted with one or more halogens;
$R_5$ and $R_6$ are independently H, alkyl of 1–4 carbons or cycloalkyl of 3–8 carbons;
$R_7$ is —NR₅R₆ or —OR₅;
$R_8$ is H or alkyl of 1–4 carbons;
$R_9$ is H, $C_1$-$C_4$ alkyl or $C_3$-$C_8$ cycloalkyl;
$R_{10}$ is H, $C_1$-$C_4$ alkyl, $C_2$-$C_4$ alkenyl, $C_3$-$C_4$ cycloalkyl, —OR₈ or —NR₁₁R₁₁ₐ;
$R_{11}$ and $R_{11A}$ are independently H or $C_1$-$C_4$ alkyl, or taken together, are —(CH₂)$_r$—;
X is Cl, Br or I;

Y is H, F, Cl, Br or NO₂, or A and Y taken together can be —O(CH₂)$_t$O—;
Z is a physiologically acceptable cation;
n is 0, 1 or 2;
p is 0 or 1;
q is 3, 4 or 5;
r is 4 or 5;
t is 1, 2 or 3;
B is —NH₂,

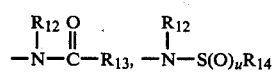

or N₃;
$R_{12}$ is H, $C_1$-$C_{10}$ alkyl or $C_3$-$C_8$ cycloalkyl;
$R_{13}$ is H; $C_1$-$C_4$ alkyl optionally substituted with one or more halogen atoms; $C_2$-$C_4$ alkenyl; $C_3$-$C_4$ cycloalkyl; phenyl; —CH₂OR₁₅; —CH(OR₁₆)OR₁₇; —CN₂S(O)$_v$R₁₄;

—OR₁₈; —SR₁₄; —CH₂N₃; the aminoalkyl groups derived from α-amino acids such as glycine, L-alanine, L-cysteine, L-proline, and D-alanine; —NR₁₉R₂₀; or C(NH₂)R₂₁R₂₂;
$R_{14}$ is $C_1$-$C_4$ alkyl, optionally substituted with one or more halogen atoms;
$R_{15}$ is H or $C_1$-$C_4$ alkyl, optionally substituted with one or more halogen atoms;
$R_{16}$ and $R_{17}$ are independently $C_1$-$C_4$ alkyl or, taken together, are —(CH₂)$_m$—;
$R_{18}$ is $C_1$-$C_4$ alkyl or $C_7$-$C_{11}$ aralkyl;
$R_{19}$ and $R_{20}$ are independently H or $C_1$-$C_2$ alkyl;
$R_{21}$ and $R_{22}$ are independently H, $C_1$-$C_4$ alkyl, $C_3$-$C_6$ cycloalkyl, phenyl or, taken together, are —(CH₂)$_s$—;
u is 1 or 2;
v is 0, 1 or 2;
m is 2 or 3;
s is 2, 3, 4 or 5; and
$R_{23}$ is independently H, alkyl of 1–4 carbons or cycloalkyl of 3–8 carbons; or a pharmaceutically suitable salt thereof; provided that:
(1) when A is CH₃S—, then B is not

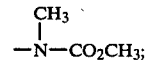

(2) when A is CH₃SO₂—, then B is not

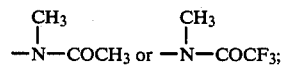

(3) when A is H₂NSO₂— and B is

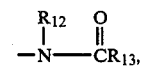

then $R_{12}$ is H;
(4) when A is —CN, B is not —N₃;
(5) when A is (CH₃)₂CH, B is not NHCOCH₂Cl.

72. A method for alleviating bacterial infection in a mammal which comprises administering to the mammal an antibacterially effective amount of a compound of claim 4.

73. A method for alleviating bacterial infection in a mammal which comprises administering to the mammal an antibacterially effective amount of a compound of claim 5.

74. A method for alleviating bacterial infection in a mammal which comprises administering to the mammal an antibacterially effective amount of a compound of claim 6.

75. A method for alleviating bacterial infection in a mammal which comprises administering to the mammal an antibacterially effective amount of a compound of claim 7.

76. A method for alleviating bacterial infection in a mammal which comprises administering to the mammal an antibacterially effective amount of a compound of claim 8.

77. A method for alleviating bacterial infection in a mammal which comprises administering to the mammal an antibacterially effective amount of a compound of claim 9.

78. A method for alleviating bacterial infection in a mammal which comprises administering to the mammal an antibacterially effective amount of a compound of claim 10.

79. A method for alleviating bacterial infection in a mammal which comprises administering to the mammal an antibacterially effective amount of a compound of claim 11.

80. A method for alleviating bacterial infection in a mammal which comprises administering to the mammal an antibacterially effective amount of a compound of claim 12.

81. A method for alleviating bacterial infection in a mammal which comprises administering to the mammal an antibacterially effective amount of a compound of claim 13.

82. A method for alleviating bacterial infection in a mammal which comprises administering to the mammal an antibacterially effective amount of a compound of claim 14.

83. A method for alleviating bacterial infection in a mammal which comprises administering to the mammal an antibacterially effective amount of a compound of claim 15.

84. A method for alleviating bacterial infection in a mammal which comprises administering to the mammal an antibacterially effective amount of a compound of claim 16.

85. A method for alleviating bacterial infection in a mammal which comprises administering to the mammal an antibacterially effective amount of the compound of claim 17.

86. A method for alleviating bacterial infection in a mammal which comprises administering to the mammal an antibacterially effective amount of the compound of claim 18.

87. A method for alleviating bacterial infection in a mammal which comprises administering to the mammal an antibacterially effective amount of the compound of claim 19.

88. A method for alleviating bacterial infection in a mammal which comprises administering to the mammal an antibacterially effective amount of the compound of claim 20.

89. A method for alleviating bacterial infection in a mammal which comprises administering to the mammal an antibacterially effective amount of the compound of claim 21.

90. A method for alleviating bacterial infection in a mammal which comprises administering to the mammal an antibacterially effective amount of the compound of claim 22.

91. A method for alleviating bacterial infection in a mammal which comprises administering to the mammal an antibacterially effective amount of the compound of claim 23.

92. A method for alleviating bacterial infection in a mammal which comprises administering to the mammal an antibacterially effective amount of the compound of claim 24.

93. A method for alleviating bacterial infection in a mammal which comprises administering to the mammal an antibacterially effective amount of the compound of claim 25.

94. A method for alleviating bacterial infection in a mammal which comprises administering to the mammal an antibacterially effective amount of the compound of claim 26.

95. A method for alleviating bacterial infection in a mammal which comprises administering to the mammal an antibacterially effective amount of the compound of claim 27.

96. A method for alleviating bacterial infection in a mammal which comprises administering to the mammal an antibacterially effective amount of the compound of claim 28.

97. A method for alleviating bacterial infection in a mammal which comprises administering to the mammal an antibacterially effective amount of the compound of claim 29.

98. A method for alleviating bacterial infection in a mammal which comprises adinistering to the mammal an antibacterially effective amount of the compound of claim 30.

99. A method for alleviating bacterial infection in a mammal which comprises administering to the mammal an antibacterially effective amount of the compound of claim 31.

100. A method for alleviating bacterial infection in a mammal which comprises administering to the mammal an antibacterially effective amount of the compound of claim 32.

* * * * *

UNITED STATES PATENT AND TRADEMARK OFFICE
CERTIFICATE OF CORRECTION

PATENT NO. : 4,705,799
DATED : NOV. 10, 1987
INVENTOR(S) : GREGORY

It is certified that error appears in the above-identified patent and that said Letters Patent is hereby corrected as shown below:

Column 6, lines 57-64, the formula set out below (on the left) should be corrected as set out below (on the right):

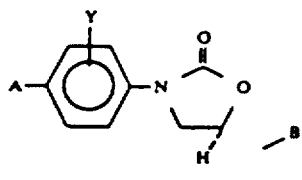 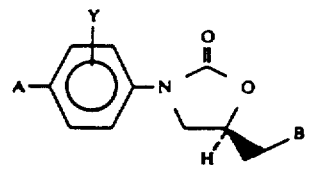

Column 7, lines 1-9, the formula set out below (on the left) should be corrected as set out below (on the right):

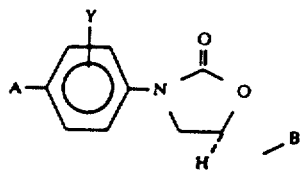 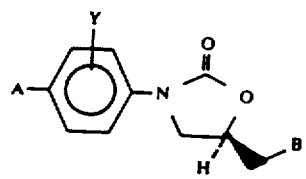

Claim 12 in Column 81, lines 16-21, the formula set out below (on the left) should be corrected as set out below (on the right):

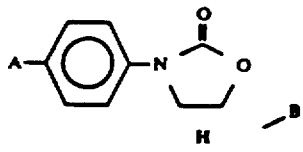 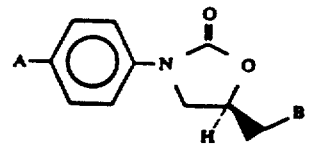

UNITED STATES PATENT AND TRADEMARK OFFICE
CERTIFICATE OF CORRECTION

PATENT NO. : 4,705,799

DATED : NOV. 10, 1987

INVENTOR(S) : GREGORY

It is certified that error appears in the above-identified patent and that said Letters Patent is hereby corrected as shown below:

Claim 14 in Column 81, lines 31-39, the formula set out below (on the left) should be corrected as set out below (on the right)

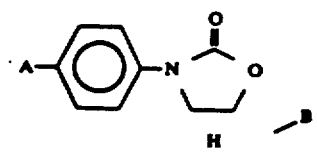 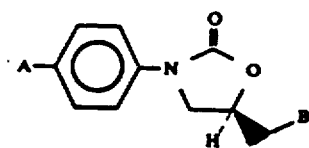

Signed and Sealed this

Seventeenth Day of May, 1988

Attest:

DONALD J. QUIGG

Attesting Officer

Commissioner of Patents and Trademarks